United States Patent
da Costa e Silva et al.

(10) Patent No.: US 7,186,561 B2
(45) Date of Patent: Mar. 6, 2007

(54) PLANT POLYNUCLEOTIDES ENCODING NOVEL NA⁺/H⁺ ANTIPORTERS

(75) Inventors: Oswaldo da Costa e Silva, Rheinland-Pfalz (DE); Manabu Ishitani, Cali (CO)

(73) Assignee: BASF Plant Science GmbH, Ludwigshafen (DE)

( * ) Notice: Subject to any disclaimer, the term of this patent is extended or adjusted under 35 U.S.C. 154(b) by 406 days.

(21) Appl. No.: 10/362,962

(22) PCT Filed: Aug. 24, 2001

(86) PCT No.: PCT/US01/26550

§ 371 (c)(1),
(2), (4) Date: Jun. 26, 2003

(87) PCT Pub. No.: WO02/16423

PCT Pub. Date: Feb. 28, 2002

(65) Prior Publication Data

US 2004/0040054 A1    Feb. 26, 2004

(51) Int. Cl.
*A01H 5/00* (2006.01)
*C12N 15/82* (2006.01)
*C12N 15/87* (2006.01)
*C12N 5/14* (2006.01)
*C07H 21/00* (2006.01)

(52) U.S. Cl. ................... 435/468; 435/320.1; 435/419; 800/287; 800/289; 536/23.6

(58) Field of Classification Search ...................... None
See application file for complete search history.

(56) References Cited

FOREIGN PATENT DOCUMENTS

| EP | 1 123 977 | 8/2000 |
|---|---|---|
| EP | 1 143 002 A1 | 10/2001 |
| JP | 2000157287 | 6/2000 |
| JP | 19990261606 | 6/2000 |
| WO | WO 91/06651 | 5/1991 |
| WO | WO 99/47679 | 9/1999 |
| WO | WO 00/37644 | 6/2000 |
| WO | WO 01/14560 | 3/2001 |
| WO | WO 01/33945 | 5/2001 |

OTHER PUBLICATIONS

Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Shi et al (PNAS, 97:6896-6901, Jun. 2000).*
Lee et al. (PNAS, 88:6389-6393, 1991).*
Apse et al., "Salt Tolerance Conferred by Overexpression of a Vacuolar Na⁺/H⁺ Antiport in *Arabidopsis*", 1999, *Science*, 285:1256-1258.
Barkla et al., "The Plant Vacuolar Na⁺/H⁺ Antiport", 1994 *Symp. Soc. Exp. Biol.*, 48:141-53.
Bohnert et al., 1996, "Metabolic Engineering for Increased Salt Tolerance—The Next Step", 1996, *Aust. J. Plant. Physiol.*, 23:661-667.
Blumwald et al., "Salt Tolerance in Suspension Cultures of Sugar Beet Induction of Sodium-Proton Antiport Activity at the Tonoplast by Growth in Salt", 1987, *Plant Physiol.*, 83:884-87.
Fischer et al., "The Mechanism of Protein Folding Implications of in Vitro Refolding Models for de Novo Protein Folding and Translocation of the Cell", 1990, *Biochemistry*, 29:2205-2212.
Flowers et al., "Breeding for Salinity Resistance in Crop Plants: Where Next?", 1995, *Aust. J. Plant. Physiol.*, 22:875-884.
Fukuda et al., "Molecular cloning and expression of the Na+/H+ exchanger gene in *Oryza sativa*", 1999, *Biochimica et Biophysica Acta*, 1446(1-2):149-155.
Fukuda et al., "Na+/H+ antiporter in tonoplast vesicles from rice roots", 1998, *Plant and Cell Physiology*, 39(2): 196-201.
Gaxiola et al., "Arabidopsis thaliana Sodium Proton Exchanger, Nhx1 mRNA, partial cds", Accession No. AF 106324, Mar. 11, 1999, pp. 1-2.
Gaxiola et al., "The *Arabidopsis thaliana* Proton Transporters, AtNhx1 and Avp1, can function in cation detoxification in yeast", 1999, *Proc. Natl. Acad. Sci. USA*, 96(4):1480-1485.
Jia, et al., 1992, "Gene amplification at a locus encoding a putative Na+/H+ antiporter confers sodium and lithium tolerance in fission yeast", *EMBO J.*, 11:1631-1640.
Machuka et al., "Sequence Analysis of Expressed Sequence Tags from an ABA-Treated cDNA Library Identifies Stress Response Genes in the Moss Physcomitrella patens", 1999, *Plant Cell Physiol.*, 40(4):378-87.
Niu et al., "Ion Homeostasis in NaCl Stress Environments", 1995, *Plant Physiol.*, 109:735-742.
Norlyn, JD, "Breeding Salt-Tolerant Crop Plants", In: *Genetic Engineering of Osmoregulation* (Eds. DW Rains, RC Valentine and A Hollaender), pp. 293-309, Plenum Press: New York.
Numata et al., "Identification of a mitochondorial Na⁺/H⁺ exchanger", 1998, *J. Biol. Chem.*, 273:6951-6959.
Orlowski et al., "Molecular cloning of putative members of the Na/H exchanger gene family, cDNA cloning, deduced amino acid sequence, and mRNA tissue expression of the rat Na/H exchanger NHE-1 and two structurally related proteins", 1992, *J. Biol. Chem.*, 267(13):9331-9339.

(Continued)

*Primary Examiner*—Ashwin Mehta
*Assistant Examiner*—Vinod Kumar
(74) *Attorney, Agent, or Firm*—Ruoying Chen; Mark Westhafer; Elaine Sale

(57) ABSTRACT

The present invention provides novel polynucleotides encoding plant Na⁺/H⁺ antiporter polypeptides, fragments and homologs thereof. Also provided are vectors, host cells, antibodies, and recombinant methods for producing said polypeptides. The invention further relates to methods of applying these novel plants polypeptides to the identification, prevention, and/or conferment of resistance to various plant diseases and/or disorders, particularly those associated with modulating environmental stress responses, such as drought and salt tolerance.

32 Claims, 11 Drawing Sheets

OTHER PUBLICATIONS

Figure 1:
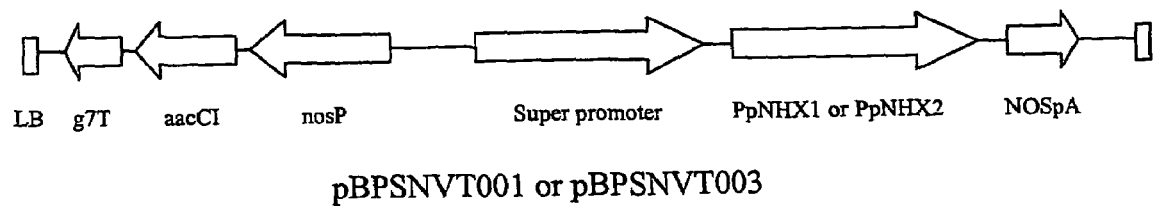

Rausch et al., 1996, "Salt Stress Responses of Higher Plants: The Role of Proton Pumps and $Na^+/H^+$-Antiporters", *J. Plant Physiol.*, 148:425-33.

Rush et al., "Breeding and Selection for Salt Tolerance by the Incorporation of Wild Germplasm into a Domestic Tomato", 1981, *J. Amer. Soc. Hort. Sci.*, 106:699-704.

Shi et al., "The *Arabidopsis thaliana* salt tolerance gene SOS1 encodes a putative Na+/H+ antiporter", 2000, *Proc. Natl. Aca. Sci. USA*, 97:6896-6901.

Siekierka et al., "The Cystolic-binding Protein for the Immunosuppressant FK-506 Is Both a Ubiquitous and Highly Conserved Peptidyl-Prolyl Cis-Trans Isomerase", 1990, *J. Biol. Chem.*, 265:21011-21015.

Stein, RL, "Exploring the catalytic activity of immunophilins," 1991, *Curr. Biol.*, 1:234-236.

Tal, M., "Genetics of salt tolerance in higher plants: theoretical and practical considerations", 1985, *Plant and Soil*, 89:199-226.

Tropschug et al., "Isolation and sequence of an FK506-binding protein from from N. crassa which catalyses protein folding", 1990, *Nature*, 346:674-677.

Tse et al., "Cloning and sequencing of a rabbit cDNA encoding an intestinal and kidney-specific Na(+)/H(+) exchanger isoform (NHE-3)", 1992, *J. Biol. Chem.*, 267:9340-9346.

Grotz et al., "Identification of a Family of Zinc Transporter Genes from Arabidopsis that Respond to Zinc Deficiency," 1998, Proc. Natl. Acad. Sci, 195:7220-7224.

Rubio et al., "Sodium-driven Potassium Uptake by the Plant Transporter HKT1 and Mutations Conferring Salt Tolerance," 1995, Science, 270:1660-1663.

Su et al., "The Expression of HAK-Type K+ Transporters Is Regulated in Response to Salinity Stress in Common Ice Plant," 2002, Plant Physiology, 129:1482-1493.

\* cited by examiner pBPSNVT001 or pBPSNVT003

Figure 2A
Nucleotide sequence of full length PpNHX1 SEQ ID NO: 1

```
   1 ATGGCGACCA ATGATGTCGT GAGCGTTTCG CATTCTATGC TACTAAAAGC
  51 TACAGATCTC AAAGATGACC GAATCGATGT AATTTCAATC TGTCTCTTTG
 101 TATTTTTACT CTGTGCGTGC ATTGTGCTGG GGCACCTTCT GGAGGAAAAT
 151 CGGTGGATGA ATGAGTCTAT TACTGCTCTT CTTCTGGGAC TCTTTACTGG
 201 ATCTATAGTG TTGATTTCAA GCAAAGGTCA AGGTTCTCAT ATTCTGGAGT
 251 TTGATGAAGA GCTTTTCTTC ATATACCTTC TTCCACCTAT AATCTTCAAT
 301 GCTGGGTTCC AGGTTAAGAA GAAGGAATTC TTTCGGAATT TCATAACAAT
 351 CATGTTTTTT GGAGTTATAG GAGTCTTTAT TTCTTTCGGA ATTATCTCAA
 401 CAGGAAGTTG GTATTTCTTC TCCAAGTTCG GACTTAAGAA CCTGCCTATT
 451 CGAGATATCC TAGCTATTGG AGTCATCTTT TCTGCTACCG ATTCCGTCTG
 501 CACGTTGCAG GTGCTGAACC AAGATGAAAC CCCTCTACTT TACAGTTTGG
 551 TCTTTGGGGA AGGAGTCGTA AATGATGCTA CTTCTGTGGT TCTGTCTCGA
 601 GCTGTTCAAA CATACAACTT TGACAATTTT ACATCCTTAG AAGGCTTACA
 651 AATTGGAGGC AGTTTCTTGT ACTTATTCTT CTCGAGTTGC ATCCTGGGAA
 701 TCGCGTCGGG CTTAATAAGC GCATATATCA TCAAGACAAT GTACTTTGGC
 751 AGGCATTCCA CGGATCGTGA AATAGCAATC ATGACATTGA TGGCGTATTT
 801 ATCTTACGTC TTTGCAGAGC TTTTCTACTT GAGTGGAATT CTCTCAGTGT
 851 TCTTTTGCGG CATTGTAATG TCTCATTACA CTTGGCATAA CGTCACGGAG
 901 AATTCTCGAA TCACAAGCAA GCATTCCTTT GCAACGATGT CATTCATTGC
 951 AGAGACGTTC ATATTTCTAT ATGTTGGAAT GGATGCTCTG GATTTCGAAA
1001 AATGGAAGAT GATGCAATCC AGTTTCACGG AATCTGCGGG CTATTTGGT
1051 AGCTTGTTGT TTCTGGTCCT GTTAGGGAGG GCCGCATTTG TGTTCCCACT
1101 CTCTGCTTTG TCCAACTACA GCACAAAGTC TCCAGACGCG AAGATTAATT
1151 TACGCCAAAT GGTTATTATC TGGTGGGCTG GACTAATGCG AGGTGCTGTC
```

Figure 2B

1201 TCAATAGCAC TGGCGTTCAA CCAGGGTGGT GATGCAAAGG CTCAAACCA

1251 AGCCACGCTA ATGGTCATTA CTATCATCAT TGTCCTCTTC AGCACTATTG

1301 TGTTCGGCAC TGCAACCAAG CCTCTTATTA GCTGGCTACT TCCACCTCAT

1351 TTCAGATCAA ATTACAGTGA TTCAGCCAGT CTCTCCCCAA AAGCGTCTCT

1401 TGATGCTGAC TTTCATATAC CACTCCTTAT GGATACAGAG CGTGAAGAAT

1451 TAGAAGCAAA TGATCGATCT ACGATAAATC AAATCCTAAA TGGTCTTCCT

1501 TGTCCTCAGT CAATAGGCAT GCTGCTGACT GCACCAAGAT CAACCATCCA

1551 CCATGTATGG AGAAAATTTG ATGATTCTTA CATGCGGCCC ACGTTTGGTG

1601 GGAGAGGATA TGTTAGGTTG GTGTCACGGC GTGATATGGA ATACAAGAA

1651 GATGAAATCC TTGAAGATCA CAGTTGA

Nucleotid sequence of partial PpNHX2 SEQ ID NO: 3
CGGCACGAGAACCTTTGCAGCTGCTAAGGCATGCAGGGTGGATGCCCGCA
AAGCTTTAACTCTCGGCATCCTGATGAATACCAAAGGATTGGTGGAGCTT
ATTGTTCTGAACATCGGTTTAGATCGTGGAGTTCTGAATTCGGAGACTTT
TGCAATCATGGTGCTGATGGCTCTCTTCACAACGTTCATGACAACACCTC
TGGTAATGGCTATATATAAACCAGCCACGAATCCCACTCCTTACACTCGT
AGGACTTTGGAAATGGAGGACTCGAAGGATGACTTGCGAATATTGTCATG
CGTGCACGGAATGAAGAACGTGGCTGCCATGATCAATCTTACAGAAGCGA
CCAGGGGCATGCGCAAACGTACTCTGCGCCTGTATATTTTGCATTTGATG
GAACTATCCGAACGTACTTCTGCCATTATGATTGTCCAGCGGGCACGTCG
GAATGGGCGCCCTTTTTTCAATCAGAGCAAACATTCGGACAACAAAGATC
AAATTGTTGCGGCCTTCGAGACATATGAACAACTAAGCAAGGTGACTGTG
AGGCCTATGACTGCAATTTCCGGGTTCGACGACATGCACGAAGACATATG
TGCGACTGCTGCTGACAAGCGGACTGCCTTGATCATGCTTCCTTTCCACA
AATCACCCAAACTGGACGGGCACTTCGATTCTACTCCAGGTTTNCGAACA
GTTAATCACAAGGTCCTCAAGCATGCACCGTGCTCTGTTGCTATTCTAAT
CGATCGTGGAGTCGGTGGATCAACCCAAGTGNCTT

Nucleotide sequnce of full length PpNHX2 SEQ ID NO: 4
TGGCACCAGCAAGATGGCGGACGCTGTGGCGTGCAAAACTATGTCGGCTACATCCAATGG
AGTGTGGCAGGGAGATGTGCCCGTTCATTTTGCTCTTCCTCTGCTCATCGTTCAAATTGTCC
TCGTTTTGGCAATCACTCGGGCGTTAGCTTTTGTCCTGAAGCCTTTGAAACAGCCCCGCGT

Figure 2C

```
CGTCGCCGAGATTATAGGCGGAATATTGCTTGGTCCATCTGCTTTTGGACGCAATAAGGAC
TACCTGCATACGATTTTTCCACATGAAAGTGTTATCATTCTGGAGGTCTTTGCAGACATGG
GACTTTTATTCTTTTTGTTCATGGTGGGGTTAGAGCTCGATATGACCCAGATTCGGAAAAC
CGGAAAGCAAGCTATGTCCATTGCTGCAGCTGGAATCACTCTGCCTTTCGTTGCAGGTGTC
GGTGTTTCCTTCGTCCTGCATCTTACAATTGCACCAGAGGGAGCTTTTGGTCCGTTTCTCGT
GTTCATGGGAGTTGCTATGTCCATCACTGCTTTCCCTGTTCTGGCACGTATTTTGGCGGAG
AGGAAGCTTTTGACTACCGAAGTAGGGCAATTGGCGATGTCAGCAGCTGCAGTTAATGAC
GTGGTTGCTTGGGTTCTTTTAGCGTTGGCGGTCGCTTTGTCGGGCTCCGGAAGGAGCCCAG
CAATTGTTGCATGGGTTCTGTTGTGTGGAATCGCATTTTGTCTGGCCATCTTCCTTGTGGTT
CAACCATGCATGCAATGGGTTGCTCATCGATCGCCCGACAATGAGCCTGTCAAAGAATAC
ATTGTAGCATTGACTTTACTTTGTGTTCTCGTTGCTGGATTCTGTACTGATGCGATAGGAGT
TCATTCCATTTTTGGCGCGTTTCTGTTTGGACTTGTTATACCTAAAGAGGGTCCTTTCGCAG
CGGCTTTGGTTGAGAAATTAGAAGATTTTGTATCTATCCTCTTGCTGCCTCTCTACTTTGCA
TCGAGTGGACTGAAGACCAACATTGGAGCTATTCACAGCGCGCAATCTTTTGGCCTTTTGG
TCTTGGTTATCAGCGTTGCTTGTCTGGGTAAAATTCTCGGAACCTTTGCAGCTGCTAAGGC
ATGCAGGGTGGATGCCCGCAAAGCTTTAACTCTCGGCATCCTGATGAATACCAAAGGATT
GGTGGAGCTTATTGTTCTGAACATCGGTTTAGATCGTGGAGTTCTGAATTCGGAGACTTTT
GCAATCATGGTGCTGATGGCTCTCTTCACAACGTTCATGACAACACCTCTGGTAATGGCTA
TATATAAACCAGCCAGGAATCCCACTCCTTACACTCGTAGGACTTTGGAAATGGAGGACT
CGAAGGATGACTTGCGAATATTGTCATGCGTGCACGGAATGAAGAACGTGGCTGCCATGA
TCAATCTTACAGAAGCGACCAGGGGCATGCGCAAACGTACTCTGCGCCTGTATATTTTGCA
TTTGATGGAACTATCCGAACGTACTTCTGCCATTATGATTGTCCAGCGGGCACGTCGGAAT
GGGCGCCCTTTTTTCAATCAGAGCAAACATTCGGACAACAAAGATCAAATTGTTGCGGCC
TTCGAGACATATGAACAACTAAGCAAGGTGACTGTGAGGCCTATGACTGCAATTTCCGGG
TTCGACGACATGCACGAAGACATATGTGCGACTGCTGCTGACAAGCGGACTGCCTTGATC
ATGCTTCCTTTCCACAAATCACCCAGACTGGACGGGCACTTCGATTCTACTCCAGGTTTCC
GAACAGTTAATCAGAAGGTCCTCAAGCATGCACCGTGCTCTGTTGCTATTCTAATCGATCG
TGGAGTCGGTGGATCAGCCCAAGTGCCTTCCAGCAACGTTGATCACAATGTTGTCGTGTAC
TTCTTTGGTGGTCCTGACGACAGGGAAGCTCTGGCATATGGTTTCCGTATGGCTGAGCATC
CGGGAGTTAAGCTTCATGTTATCCGTTTCCTTTCTCACAGCGTCGTCATGGACGACGGCCA
TGGAGGATTAGCTTCCGTCGGATCAGAGGTATCTGAGATTGGCAAGACGGAGGTGAGCGA
TACTCGTTTCCAGTTCGCGATGCATGGTCTGGACCAAAACAGGCAAAGGGAGTTGGATGA
AGAAGCCTTGGGCCATGTGCGTAGGAGGCAAGCTTCTGAAGATGGAAGAGTCACATACGT
AGAAATGCAGGTATCTGAGCCTCTTGAAGAGGTGGTGAGATTGAGTAGCTCTCGTGAACA
CGATATTATTTTGGTTGGCCGATCGAGAAGGCCAACGCCATTTTAGAGCGATTCCGTCGT
AAGCACGCAGAATATGCAGAGCTTGGCCCTATTGGAGATGCTCTGATGGCCCCACAGGTA
CGAGCATCTGTCTTAGTATTTCAGCAGCACGATCATGTGCTTGCCGATCCACTTCCTAATA
CCTCTGAAACGGAGGCCGTCAAAGAGTTGCAGACCTTCCCATCATCCAAGGAATTGGTGG
```

Figure 2D

ATCGTAAAGGTGATGTACAGAAGATCGACTTGTCTTCTCCTGACCACCGCGTGTATATGAC
CCGGGTCTAGAGCGGCCGCCACCGCGGTGGAGCTCCAGCTTTTGTTCCCTTTAGTGAGGGT
TAATTGCGCG

Figure 3

Amino acid sequence PpNHX1 SEQ ID NO: 2

1   MATNDVVSVS HSMLLKATDL KDDRIDVISI CLFVFLLCAC IVLGHLLEEN

51  RWMNESITAL LLGLFTGSIV LISSKGQGSH ILEFDEELFF IYLLPPIIFN

101 AGFQVKKKEF FRNFITIMFF GVIGVFISFG IISTGSWYFF SKFGLKNLPI

151 RDILAIGVIF SATDSVCTLQ VLNQDETPLL YSLVFGEGVVNDATSVVLSR

201 AVQTYNFDNF TSLEGLQIGG SFLYLFFSSC ILGIASGLIS AYIIKTMYFG

251 RHSTDREIAI MTLMAYLSYV FAELFYLSGI LSVFFCGIVMSHYTWHNVTE

301 NSRITSKHSF ATMSFIAETF IFLYVGMDAL DFEKWKMMQSFTESAGLFG

351 SLLFLVLLGR AAFVFPLSAL SNYSTKSPDA KINLRQMVIIWWAGLMRGAV

401 SIALAFNQGG DAKDSNQATL MVITIIIVLF STIVFGTATK PLISWLLPPH

451 FRSNYSDSAS LSPKASLDAD FHIPLLMDTE REELEANDRS TINQILNGLP

501 CPQSIGMLLT APRSTIHHVWKFDDSYMRPTFGGRGYVRLVSRRDMDIQE

551    DEILEDHS*

Amino acid sequence PpNHX2 SEQ ID NO: 5

MADAVACKTMSATSNGVWQGDVPVHFALPLLIVQIVLVLAITRALAFVLKPLKQPRVVAEIIG
GILLGPSAFGRNKDYLHTIFPHESVIILEVFADMGLLFFLFMVGLELDMTQIRKTGKQAMSIAA
AGITLPFVAGVGVSFVLHLTIAPEGAFGPFLVFMGVAMSITAFPVLARILAERKLLTTEVGQLA
MSAAAVNDVVAWVLLALAVALSGSGRSPAIVAWVLLCGIAFCLAIFLVVQPCMQWVAHRSP
DNEPVKEYIVALTLLCVLVAGFCTDAIGVHSIFGAFLFGLVIPKEGPFAAALVEKLEDFVSILLL
PLYFASSGLKTNIGAIHSAQSFGLLVLVISVACLGKILGTFAAAKACRVDARKALTLGILMNTK
GLVELIVLNIGLDRGVLNSETFAIMVLMALFTTFMTTPLVMAIYKPARNPTPYTRRTLEMEDSK
DDLRILSCVHGMKNVAAMINLTEATRGMRKRTLRLYILHLMELSERTSAIMIVQRARRNGRPF
FNQSKHSDNKDQIVAAFETYEQLSKVTVRPMTAISGFDDMHEDICATAADKRTALIMLPFHKS
PRLDGHFDSTPGFRTVNQKVLKHAPCSVAILDRGVGGSAQVPSSNVDHNVVVYFFGGPDDRE
ALAYGFRMAEHPGVKLHVIRFLSHSVVMDDGHGGLASVGSEVSEIGKTEVSDTRFQFAMHGL
DQNRQRELDEEALGHVRRRQASEDGRVTYVEMQVSEPLEEVVRLSSSREHDIILVGRSRRPTP
FLERFRRKHAEYAELGPIGDALMAPQVRASVLVFQQHDHVLADPLPNTSETEAVKELQTFPSS
            KELVDRKGDVQKIDLSSPDHRVYMTRV

Figure 4A

```
                              1                                         40
O. sativa Q9SXJ8         (1)  ----------------------------------------
Aribodopsis AtNhx1       (1)  ----------------------------------------
SEQ ID #2                (1)  ----------------------------------------
D.melanogaster Q9VP1     (1)  -------------------------------MRVWVAYSA
C. elegans Q9X1H         (1)  MMLSVEEQVLRNNIELMFTFNSLKILANGVTWQLWESTLN 41                                        80
O. sativa Q9SXJ8         (1)  ----------------------------------------
Aribodopsis AtNhx1       (1)  ----------------------------------------
SEQ ID #2                (1)  ----------------------------------------
D.melanogaster Q9VP1    (10)  AALLLLVHAGPESISGQEVPQSKTSSNTTTTDNSSSIHTV
C. elegans Q9X1H        (41)  QGTATSGIMRFALKTALSICIFLLIFQTVDSDSSDSSASA 81                                       120
O. sativa Q9SXJ8         (1)  ------------------------------MGMEVAAARL
Aribodopsis AtNhx1       (1)  --------------------------------MLDSLVSK
SEQ ID #2                (1)  -----------------------------MATNDVVSVSHSMLL
D.melanogaster Q9VP1    (50)  SDVFVNSPLGNVTPSISASGNASTTKRGNASTLVTDPPLI
C. elegans Q9X1H        (81)  SVVSGAVKSEDTVVAVNKTDVLGEAIDANATSLEQHGAAI 121                                      160
O. sativa Q9SXJ8        (11)  GALYTTSDYASVVSINLFVALLCACIVLGHLLEEN--RWV
Aribodopsis AtNhx1       (9)  LPSLSTSDHASVVALNLFVALLCACIVLGHLLEEN--RWM
SEQ ID #2               (16)  KATDLKDDRIDVISICLFVFLLCACIVLGHLLEEN--RWM
D.melanogaster Q9VP1    (90)  DSHAVEQEHNSSLSLFFVICVIMLGILLIHSMLQTGFQYL
C. elegans Q9X1H       (121)  VGNVSE-EKKRSLAIFFILFVIMLATLVVHMLIVSKIHWM 161                                      200
O. sativa Q9SXJ8        (49)  NESITALIIGLCTGVVILLMT--KGKSSHLFVFSEDLFFI
Aribodopsis AtNhx1      (47)  NESITALLIGLGTGVTILLIS--KGKSSHLLVFSEDLFFI
SEQ ID #2               (54)  NESITALLLGLFTGSIVLISS--KGQGSHILEFDEELFFI
D.melanogaster Q9VP1   (130)  PESIVVVFLGAFIGLSLNVMSGQNGSWKREEVFSPMGFFL
C. elegans Q9X1H       (160)  PESLAIVALGALIGSILSYSR--R-DWSEIEALSPDVFFL 201                                      240
O. sativa Q9SXJ8        (87)  YLLPPIIFNAGFQVKKKQFFRNFMTITLFGAVGTMISFFT
Aribodopsis AtNhx1      (85)  YLLPPIIFNAGFQVKKKQFFRNFVTIMLFGAVGTIISCTI
SEQ ID #2               (92)  YLLPPIIFNAGFQVKKKEFFRNFITIMFFGVIGVFISFGI
D.melanogaster Q9VP1   (170)  VLLPPIIFESGYNLHKGNFFQNIGSILVFAIFGTTISALV
C. elegans Q9X1H       (197)  VLLPPIIFENAYNLNKGYFFSNFVPILTFAIFGTTISAMV 241                                      280
O. sativa Q9SXJ8       (127)  ISIAAIAIFSRMNIGTLDVGDFLAIGAIFSATDSVCTLQV
Aribodopsis AtNhx1     (125)  ISLGVTQFFKKLDIGTFDLGDYLAIGAIFAATDSVCTLQV
SEQ ID #2              (132)  ISTGSWYFFSKFGLKNLPIRDILAIGVIFSATDSVCTLQV
D.melanogaster Q9VP1   (210)  IGAGIYLLGLGEVAFRLSFSESFAFGSLISAVDPVATVAI
C. elegans Q9X1H       (237)  IGAGLYILGAIGLIFEFTFFECFAFAAMISAVDPVGTLAI 281                                      320
O. sativa Q9SXJ8       (167)  LN-QDETPFLYSLVFGEGVVNDATSIVLFNALQN----FD
Aribodopsis AtNhx1     (165)  LN-QDETPLLYSLVFGEGVVNDATSVVVFNAIQS----FD
SEQ ID #2              (172)  LN-QDETPLLYSLVFGEGVVNDATSVVLSRAVQT----YN
D.melanogaster Q9VP1   (250)  FHALDVDPILNMLVFGESILNDAISIVLTASITQSAN-VN
C. elegans Q9X1H       (277)  FQAVKVESLLYMLVFGESMLNDAVSIVLAATALRHAKPSF
```

Figure 4B

```
                              321                                        360
O. sativa Q9SXJ8       (202) LVHIDAAVVLKFLGNFFYLFLSSTFLGVFAGLLSAYIIKK
Arabidopsis AtNhx1     (200) LTHLNHEAAFHLLGNFLYLFLLSTLLGAATGLISAYVIKK
SEQ ID #2              (207) FDNFTSLEGLQIGGSFLYLFFSSCILGIASGLISAYIIKT
D.melanogaster Q9VP1   (289) AEASTGEAMFSALKTFCAMFFASAGIGVIFALISALLLKH
C. elegans Q9X1W       (317) NSLPASEIITSAFVTFTEMFFFSACLGVGIGLLSALLFKH 361                                        400
O. sativa Q9SXJ8       (242) LYIGRHSTDREVALMMLMAYLSYMLAELLDLSGILTVFFC
Arabidopsis AtNhx1     (240) LYFGRHSTDREVALMMLMAYLSYMLAELFDLSGILTVFFC
SEQ ID #2              (247) MYFGRHSTDREIAIMTLMAYLSYVFAELFYLSGILSVFFC
D.melanogaster Q9VP1   (329) IDLRKHP-SLEFAMMLMFTYAPYVLAEGIHLSGIMAILFC
C. elegans Q9X1W       (357) VDLRKTP-SLEFALLLIFSYIPYGFAEALDLSGIMAILFC 401                                        440
O. sativa Q9SXJ8       (282) GIVMSHYTWHNVTESSRVTTKHAFATLSFIAETFLFLYVG
Arabidopsis AtNhx1     (280) GIVMSHYTWHNVTESSRITTKHTFATLSFLAETFIFLYVG
SEQ ID #2              (287) GIVMSHYTWHNVTENSRITSKHSFATMSFIAETFIFLYVG
D.melanogaster Q9VP1   (368) GIVMSHYTHFNLSTVTQITMQQTMRTLAFIAETCVFAYLG
C. elegans Q9X1W       (396) GISMSQFTRHNVSPIAQITFRHTFRTISFVAETSTFAYIG 441                                        480
O. sativa Q9SXJ8       (322) MDALDIEKWEFASDRPGKSIGISSILLGLVLIGRAAFVFP
Arabidopsis AtNhx1     (320) MDALDIDKWRSVSDTPGTSIAVSSILMGLVMVGRAAFVFP
SEQ ID #2              (327) MDALDFEKWKMMQSSFTESAGLFGSLLFLVLLGRAAFVFP
D.melanogaster Q9VP1   (408) LAIFSFKHQVELSF------VIWA--IVLCLIGRACNIFP
C. elegans Q9X1W       (436) MAFFTIKLNFAPWLIFWS--------VVLCLLGRACNVFP 481                                        520
O. sativa Q9SXJ8       (362) LSFLSNLTKKAPNEKITWRQQVVIWWAGLMRGAVSIALAY
Arabidopsis AtNhx1     (360) LSFLSNLAKKNQSEKINFNMQVVIWWSGLMRGAVSMALAY
SEQ ID #2              (367) LSALSNYSTKSPDAKINLRQMVIIWWAGLMRGAVSIALAF
D.melanogaster Q9VP1   (440) LAFLVNKFR---EHKINNKMQFIMWFSGLR-GAISYALSL
C. elegans Q9X1W       (468) LAYLVNQCR--KDVQISMKNQIIMWFSGMR-GAVCFALVL 521                                        560
O. sativa Q9SXJ8       (402) NKFTRSGHTQLHGNAIMITSTITVVLFSTMVFGMMTKPLI
Arabidopsis AtNhx1     (400) NKFTRAGHTDVRGNAIMITSTITVCLFSTVVFGMLTKPLI
SEQ ID #2              (407) N---QGGDAKDSNQATLMVITIIIVLFSTIVFGTATKPLI
D.melanogaster Q9VP1   (476) HLN----LDSQEKRHVIITTTLIIVLFTTLVLGGSTMPLL
C. elegans Q9X1W       (505) YMDLDK-----EKKSILLTTVLFLILFTTIFLGGSALPFI 561                                        600
O. sativa Q9SXJ8       (442) RLLLPAS--GHPVTSEPSSPKS-----LHSPLLTSMQGSD
Arabidopsis AtNhx1     (440) SYLLPHQNATTSMLSDDNTPKS-----IHIPLLDQDSFIE
SEQ ID #2              (444) SWLLPPHFRSNYSDSASLSPKASLDADFHIPLLMDTEREE
D.melanogaster Q9VP1   (512) KYLKPGKKRRARGSGRNAAEEGG--RRNGSGRKRSKSISL
C. elegans Q9X1W       (540) SFINRCYP-NERQRKRRRTPRNKESTGNSSALMMSKTQEM 601                                        640
O. sativa Q9SXJ8       (475) LEST------------TNIVRPSSLRMLLTKPTHTVHYYW
Arabidopsis AtNhx1     (475) PSGN------------HNVPRPDSIRGFLTRPTRTVHYYW
SEQ ID #2              (484) LEANDRSTI---NQILNGLPCPQSIGMLLTAPRSTIHHVW
D.melanogaster Q9VP1   (550) SKTREWGQA---IDSEHLSELTEEEDVTFTQARDRFGRMD
C. elegans Q9X1W       (579) SFFGSDDWGPKKSALDATSSAGRIMRQLFVRKFTAIERLE
```

Figure 4C

```
                              641                                    680
    O. sativa Q9SXJ8    (503) RKFDDALMRPMFGGR---------------------G
  Arabidopsis AtNhx1    (503) RQFDDSFMRPVFGGR---------------------G
         SEQ ID #2      (521) RKFDDSYMRPTFGGR---------------------G
D.melanogaster Q9VP1    (587) RKYFIPFFTRRFNSQELHECKSQMAD----------LTNK
     C. elegans Q9X14   (619) NRDKLAALTKRALASDQMTDSDDVEFGGGGGVGGGGRMKD 681                                    720
    O. sativa Q9SXJ8    (519) FVPFSPGSPTEQSHGGR-----------------------
  Arabidopsis AtNhx1    (519) FVPFVPGSPTERNPPDLSKA--------------------
         SEQ ID #2      (537) YVRLVSRRDMDIQEDEILEDHS------------------
D.melanogaster Q9VP1    (617) WYQAIRVSPLDSDESDEEIGLAAS--TSQIHLTRS-----
     C. elegans Q9X14   (659) DVTPTRGRSGSRNSSDVIISAGGGGVSGEHHLLISSGSDS 721
    O. sativa Q9SXJ8    (536) -----SEQ ID NO: 23
  Arabidopsis AtNhx1    (539) -----SEQ ID NO: 24
         SEQ ID #2      (559) -----SEQ ID NO: 2
D.melanogaster Q9VP1    (650) -----SEQ ID NO: 25
     C. elegans Q9X14   (699) STNEF SEQ ID NO: 26
```

Figure 5

```
                     (112) 112        120        130        140        150        160        170         189
          ppNHX2(108) LELDMTQNRKTGKQAMSIAAAGIELPFVAGVGSFNLHLTIAPEGAFGPFVFMGVAMSITAFPVLARILAERKLLTT    SIN: 27
A. thaliana Q9SUQ7(110) LELDPKSLKRTGKRAMSEALAGIMPFVLGLGTSFALRSSIADEASKAPFMVFMGVAMSITAFPVLARILAEIKLLTT    SIN: 28
      O.sativa Q9SXJ8 (71) ----------GKS----N--HLFVFSEDEFFIMLPPIIFNAGFCMKKKQFFRNFMHITLFGAVGTMESFFTIESIA    SIN: 29
A. thaliana Q9SS27 (71) ----------GKN----N--HLEVFSEDEFFIMALPPIIFNAGFQMVKKKQFFRNFWMIMAFGAMGIMVMSCTIMSLG    SIN: 30
A. thaliana Q9LUN4(112) LELDFAARMMTGKRGMLIALAGISDPFMVGMSTSFVLSAMISKGVDQLEHMVFMGVALSITAFPVLARILAELKLMMT    SIN: 31
        Consensus(112) LELD    IKKIGK AL IASAGIILPFV GLG SFLL  TIA AG QVPFLVFMGVALSITAFPVLARILAE KLLTT   SIN: 32
```

Figure 6

| Identity (similarity) | O.Sativa Q9SXJ8 | SEQ ID #2 | SEQ ID #5 | D.Melanogaster Q9VP1 | C.elegans Q9X14 | AtNHX1 AAD 16946 | Arabidopsis BAB02053 |
|---|---|---|---|---|---|---|---|
| O.Sativa Q9SXJ8 | - | - | - | - | - | | - |
| SEQ ID #2 | 56 (67) | - | - | - | - | - | - |
| SEQ ID #5 | 10 (20) | 27 (32) | - | | | | - |
| D.Melanogaster Q9VP1 | 25 (40) | 24 (39) | 11 (22) | - | - | - | - |
| C.elegans Q9X14 | 22 (34) | 24 (37) | 10 (23) | 36 (52) | - | - | - |
| AtNHX1 AAD 16946 | 72 (81) | 56 (68) | 10 (20) | 24 (38) | 22 (36) | - | - |
| Arabidopsis BAB02053 | 10 (22) | 11 (22) | 50 (63) | 11 (22) | 12 (26) | 10 (21) | - |

PLANT POLYNUCLEOTIDES ENCODING NOVEL NA+/H+ ANTIPORTERS

FIELD OF THE INVENTION

The present invention provides novel polynucleotides encoding plant Na$^+$/H$^+$ antiporter polypeptides, fragments and homologs thereof. Also provided are vectors, host cells, antibodies, and recombinant methods for producing said polypeptides. The invention further relates to methods of applying these novel plant polypeptides to the identification, prevention, and/or conferment of resistance to various plant diseases and/or disorders, particularly those associated with modulating environmental stress responses, such as drought and salt tolerance.

BACKGROUND OF THE INVENTION

Environmental stress due to salinity is one of the most serious factors limiting the productivity of agricultural crops, which are predominantly sensitive to the presence of high concentrations of salts in soil. It is estimated that 35–45% of the 279 million hectares of land irrigation is presently affected by salinity. This is exclusive of the regions classified as arid and desert lands. In this century, more areas including vast regions of Australia, Europe, Southwest USA, the Canadian prairies and others have seen considerable declines in crop productivity due to salinity in lands. The consequence represents a significant economic and political factor and contributes to food shortages in many undeveloped countries.

Although there is engineering technology available to overcome this problem, though drainage and supply of high quality water, these measures are extremely costly. In most of the cases, due to the increased need for extensive agriculture, neither improved irrigation efficiency nor the installation of drainage systems is applicable. Moreover, in the arid and semi-arid regions of the world water evaporation exceeds precipitation. These soils are inherently high in salt and require vast amounts of irrigation to become productive. Since irrigation water contains dissolved salts and minerals, an application of water is also an application of salt that compounds the salinity problem.

Conventional breeding strategies for salt tolerance have been attempted for a long time. These breeding practices have been based mainly on the following strategies: a) the use of wide crosses between crop plants and their more salt-tolerant wild relatives (Rush, P W and Epstein, E, 1981 J. Amer. Soc. Hort. Sci. 106, 699–704) (b) screening and selecting for variation within a particular phenotype (Norlyn, J D. 1980. In: Genetic Engineering of Osmoregulation (Eds. D W Rains, R C Valentine and A Hollaender) pp. 293–309. Plenum press: New York.), c) designing new phenotypes through recurrent selection (Tal, M. 1985. Plant and Soil 89, 199–226). The lack of success in generating tolerant varieties would suggest that conventional breeding practices are not enough and that in order to succeed a breeding program should include the engineering of transgenic crops which allows one to generate salt stress-tolerant crops (Flowers T J and Yeo, A R, 1995. Aust. J. Plant. Physiol. 22., 875–884., Bohnert H J and Jensen, R G. 1996. Aust. J. Plant. Physiol. 23., 661–667.)

Plant cells are structurally well suited to the compartmentation of ions. Large membrane-bound vacuoles are the site for a considerable amount of sequestration of ions and other osmotically active substances. Transport mechanisms could actively move ions into the vacuole, removing the potentially harmful ions from cytosols. Thus, at the cellular level both specific transport systems for sodium accumulation in the vacuole and sodium extrusion out of the cell are correlated with salt tolerance.

Several sodium transport systems associated with salt tolerance have been characterized in different organisms and a few of the genes involved in this process have been identified and in some cases the predicted role of protein has been investigated in transgenic/overexpression experiments. A single gene (sod2) coding for a Na$^+$/H$^+$ antiport has been shown to confer sodium tolerance in fission yeast (Jia, Z P, et al. 1992 EMBO J. 11, 1631–1640., Young, P G and Zheng, P J. Patent#WO9106651), although the role of this plasma membrane-bound protein appears to be only limited to yeast One of the main disadvantages of using this gene for transformation of plants is associated with the typical problems encountered in heterologous gene expression. Two homologues of sodium antiporter, AtNhx1 and SOS1 from salt-sensitive plants, *Arabidopsis thaliana* have been identified and characterized (Apse, M P et al., 1999, Science 285, 1256–1258., Shi, H et al., 2000 Proc. Natl. Aca. Sci. USA 97, 6896–6901). Overexpression of AtNhx1 in Arabidopsis as well as in fusion yeast shows increased salt tolerance due to better performance of salt compartmentation into the vacuole (Gaxiola, R A., et al. 1999. Proc. Natl. Acad. Sci. USA. 96, 1480–1485., Apse, MP et al., 1999, Science 285, 1256–1258.,). However, a comparison of ion distribution in cells and tissues of various plant species indicates that a primary characteristic of salt-tolerant plants is their ability to exclude sodium out of the cell and to take up sodium and sequester it in the cell vacuoles (Niu, X., et al., 1995 Plant Physiol. 109, 735–742). This strongly suggests that Na$^+$/H$^+$ antiporter from salt-tolerant plants have functionally more effective sodium transport systems compared with salt-sensitive plants such as Arabidopsis.

Therefore, elucidating the function of sodium transport genes in salt tolerant plants will not only advance our understanding of plant adaptation and tolerance to salinity stress, but also may provide important information for designing new strategies for crop improvement Newly generated salt tolerant plants will have many advantages, such as increasing the range that crop plants can be cultivated in salinity lands. This invention fulfills this need by providing the sequences of plant Na$^+$/H$^+$ antiporter genes that are expressed in the halophyte *Physcomitrella patens*, which can therefore provide a basis of increasing the salt tolerance of non-halophytic plants.

Moreover, the present invention provides novel polynucleotides encoding plant Na$^+$/H$^+$ antiporter polypeptides, fragments and homologs thereof. Also provided are vectors, host cells, antibodies, and recombinant methods for producing said polypeptides. The invention further relates to methods of applying these novel plant polypeptides to the identification, prevention, and/or conferment of resistence to various plant diseases and/or disorders, particularly environmental stress tolerance in plants.

Due to the commercial consequences of environmental damage to crops, there is an interest in understanding how to improve a plant's response to environmental damage. By improving a plant's performance or survival in response to cold, drought and salinity the environment stress-related risks of farming can be reduced. This invention fulfills in part the need to identify new Na$^+$/H$^+$ antiporters capable of conferring drought, freezing and salt tolerance to plants upon over-expression. Namely, we describe Na$^+$/H$^+$ antiporters (PpNHX1 and PpNHX2) from *Physcomitrella patens*.

BRIEF SUMMARY OF THE INVENTION

This invention provides novel nucleic acid molecules encoding for either fully active polypetides or portions thereof from the enzymes Na$^+$/H$^+$ antiporter from *Physcomitrella patens*.

The present invention further provides a general method for engineering salt-tolerant plants. Moreover, this method should be applicable to all plants of interest. Moreover, this method should be applicable to other environmental stresses.

The present invention describes the introduction of a Na$^+$/H$^+$ antiporter activity from the halophyte *Physcomitrella patens* into plants. This method should be very well suited to enhance salt tolerance as the antiporter from a halophyte is more efficient to protect the cell from salt stress than is the antiporter from non-halophyte sources.

Further described in this invention are vectors used to transform *Arabidopsis,* Rapeseed, soybeans and corn plants.

In a preferred aspect of this invention, the engineering of salt-tolerant plants is described.

Moreover, the invention provides methods of applying the polynucleotides and polypeptides of the invention for creating transgenic plants with desirable traits, which include, but are not limited, to enhanced plant defense, drought tolerance, salt tolerance, ultraviolet(uv) tolerance, enhanced flower development and terpene synthesis. The invention provides antibodies specific to polypeptides of the present invention. Further, the invention provides methods of using antibodies of the present invention to modulate plant phenotype, both functionally and morphologically. The invention also provides methods for more particularly refining the function of the polynucleotides and/or polypeptides of the present invention.

BRIEF DESCRIPTION OF THE FIGURES/DRAWINGS

FIG. 1—Diagram of the plant expression vector pGMSG containing the plant promoter controlling the expression of the *Physcomitrella* Na$^+$/H$^+$ Antiporter (PpNHX1 and PpNHX2). Diagram of the plant expression vector pGMSG containing the plant promoter controlling the expression of the *Physcomitrella* Na$^+$/H$^+$ Antiporter gene.

The components are: aacCI gentamycin resistance gene (Hajdukiewicz et al., 1994 (Hajdukiweicz, P., Svab, Z. and Maliga, P. (1994). The small, versatile pPZP family of Agrobacterium binary vectors for plant transformation. Plant Molecular Biology 25, 989–994)), nosP NOS promoter (Becker et al., 1992 (Becker, D., E. Kemper, J. Schell, and R Masterson. 1992. New plant binary vectors with selectable markers located proximal to the left T-DNA border. Plant Mol. Biol. 20(6): 1195–1197)), g7T terminator (Becker et al., 1992), NOSpA terminator (Jefferson et al., 1987 (Jefferson, R. A., T. A. Kavanagh, and M. W. Bevan. 1987. GUS fusions: β-Glucuronidase as a sensitive and versatile gene fusion marker in higher plants. EMBO J. 6(13): 3901–7)). In pBPSNVT001 and pBPSNVT003, the expression of the Na$^+$/H$^+$ Antiporter (PpNHX1 and PpNHX2) gene is under control of the constitutive superpromoter. (Ni et al., 1995 (Ni, M., Cui, D., Einstein, J., Narasimhulu, S., Vergara, C. E., and Gelvin, S. B. (1995) Strength and tissue specificity of chimeric promoters derived from the octopine and mannopine synthase gene. The Plant Journal 7(4): 661–676)).

FIGS. 2A–D—Na$^+$/H$^+$ Antiporters. Nucleotide sequence of the full-length PpNHX1 (SEQ ID NO: 1); and the partial and full-length PpNHX2 (SEQ ID NO: 3 and NO: 4, respectively) from *Physcomitrella patens.*

FIG. 3—Deduced amino acid sequence of the full length Na$^+$/H$^+$ antiporters NHX1 (SEQ ID NO: 2); and NHX2 (SEQ ID NO: 5) from *Physcomitrella patens*

FIGS. 4A–C—Amino acid multiple sequence alignment (CLUSTAL W algorithm, blosum62 scoring matrix) between the full-length Vacuole-type Na$^+$/H$^+$ Antiporter (SEQ ID NO:2) and sequences of *Oryza sativa* (Q9SXJ8, SEQ ID NO:23), *Caenorhabditis elegans* (Q9X14, SEQ ID NO:26), *Drosophila melanogaster* (Q9VP1, SEQ ID NO:25) and *Arabidopsis* AtNHX1 (AAD16946, SEQ ID NO:24). The amilolide binding site is highlighted.

FIG. 5—Amino acid pile up comparison (PARAMETERS) of SEQ ID NO:5 and sequences of *Oryza sativa* (Swiss plot #:Q9SXJ8, SEQ ID NO:29), *Arabidopsis thaliana* (Swiss plot #:Q9SUQ7, SEQ ID NO:28; Q9SS27, SEQ ID NO:30; Q9LUN4, SEQ ID NO:31).

FIG. 6—Amino acid sequence comparison (fasta: Pairwise alignment, blosum 62 scoring matrix, gap opening penalty: 10, gap extension penalty: 0.1) of the full-length Na$^+$/H$^+$ Antiporter (SEQ ID NO:2 and SEQ ID NO:5), *Oryza sativa* (Q9SXJ8, SEQ ID NO:29), *Caenorhabditis elegans* (Q9X14, SEQ ID NO:26), *Drosophila melanogaster* (Q9VP1, SEQ ID NO:25), and *Arabidopsis* AtNHX1 (AAD16946, SEQ ID NO:24) and Ha$^+$/H$^+$ exchanging protein-like (BAB02053). The percent identity and percent similarity values are shown in parenthesis.

DETAILED DESCRIPTION OF THE INVENTION

The present invention may be understood more readily by reference to the following detailed description of the preferred embodiments of the invention and the Examples included herein.

One aspect of this invention pertains to isolated nucleic acid molecules that encode fully active polypeptides the PpNHX1 and PpNHX2 Na$^+$/H$^+$ antiporter from *Physcomitrella patens*. Moreover, this invention pertains to nucleic acid fragments originated from the clones mentioned above, as well as other nucleic acid fragments from other organisms that can be isolated using the described nucleic acid fragments as probes in hybridization experiments.

One embodiment of the present invention relates to increasing stress resistance in a plant by transforming a plant using the polynucleotides and polypeptides, including agonists and/or fragments thereof. This method has herein been demonstrated for *Arabidopsis thaliana*, Rapeseed, soybeans, and corn but its application is not restricted to these plants. The method relies on the increased sodium transport efficiency of the PpNHX1 and PpNHX2 polypeptides as compared to endogenous plant sodium antiporters. The method is most advantageous when the PpNHX1 and PpNHX2 polynucleotides are expressed constitutively in a plant However, it may be advantageous to have the PpNHX1 and PpNHX2 polynucleotides expressed respectively in specific tissues and/or under the control of an inducible promoter using promoters disclosed herein. Alternatively, the method is also advantageous when the expression of the PpNHX1 and PpNHX2 polynucleotides are under the control of a stress-responsive promoter, such as a drought and/or salt activatable promoter.

The present invention can make a significant contribution to the art by providing new strategies to engineer salt-and drought-tolerance in crop plants, especially the use of the previously unknown PpNHX1 and PpNHX2 clone, respectively. Over-expression of these $Na^+/H^+$ antiporter (PpNHX1 and PpNHX2) in Arabidopsis confers a high degree of salt tolerance to this plant It is noteworthy that the analyses of these transgenic lines were performed with T2 plants. The results will be better when a homozygous, strong expression variant is found. The predicted proteins of PpNHX1 and PpNHX2 are homologous to several plant $Na^+/H^+$ antiporter. The PpNHX1 and PpNHX2 proteins have 27% identity each other at the amino acid level, suggesting that these genes could function differentially as a $Na^+/H^+$ antiporter (e.g. stress specific or tissue/organ specific).

The present invention also encompasses polynucleotides of the present invention comprising a sodium binding site (amilolide binding site).

In another embodiment of the present invention, the polynucleotides and polypeptides of the present invention, in addition to agonists and/or fragments thereof, are useful in modulating the stress tolerance in a plant, preferably modulating a plant's tolerance to the following, non-limiting conditions: limited or inadequate water availability, excess salt or osmotic conditions, excess temperature conditions, excess metal concentrations in soil or water, chemical stress, in addition to oxidative stress. Moreover, the polynucleotides and polypeptides of the present invention are useful in modulating multiple stress responses in a plant, preferably at least one, two, three, four, or more stres respones.

The invention also encompasses the use of the polynucleotides and polypeptides of the present invention, including fragments thereof, in modulating the activity of the sodium antiporter of the present invention, in addition to other sodium antiporters, through protein-protein interactions of the C-terminal regulatory domain of the present invention. Proteins that bind to the C-terminal regulatory domain of the present invention are encompasses by the present invention.

The polynucleotides can also be used to express recombinant proteins for analysis, characterization and agronomic use, to express recombinant proteins to raise antibodies directed against polypeptides of the present invention, as markers for tissues in which the corresponding protein is expressed (e.g., preferentially, or non-preferentially), as hybridization markers on Southern gels, as genetic markers for breeding assistance, as RFLP markers, as markers for genotyping (varieties, etc,), and the encoded protein, can, at the very least, be used as a molecular weight marker.

The polynucleotides of the present invention are also useful as chromosome markers or tags (when labeled) to identify chromosomes, to map related gene positions within a chromosome, or as a comparative reference to endogenous DNA sequences of mutant plants to identify allelic varients, and/or spontaneous or biotic mutations.

The polynucleotides of the present invention are also useful for genetic fingerprinting, for selecting and making oligomers for attachment to a "gene chip" or other support, including for examination of expression patterns for particular genes, to differentiate intron and/or exon boundaries, to identify splice and/or allelic variants, and as diagnostic tools for identification of developmental stages, disease states, and/or nutrient levels.

The present invention encompasses polynucleotides that hybridize to the polynucleotides of the present invention under either stringent or non-stringent conditions. Such hybridization may be used to identify orthologs, homologs, alleleic variants, variants, and/or mutants of the polynucleotides of the present invention. Additionally, the polynucleotides of the present invention may be used to clone orthologs, homologs, alleleic variants, variants, and/or mutants of the polynucleotides of the present by using oligonucleotides directed to polynucleotide sequences of the present invention, and performing PCR on plant cell or tissue samples.

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that discribed by Ozenberger and Young (Mol Endocrinol., 9(10):1321–9, (1995); and Ann N Y Acad. Sci., 7;766:279–81, (1995)).

Potential uses of polynucleotides and polypeptides of the present invention include nutritional (e.g., as an amino acid supplement), as a carbon source, as nitrogen source, as a carbohydrate source, modulating plant defense activity, modulating signal transduction, modulating metabolite transport (e.g., carbon, nitrogen fluxes, etc.), conferring abiotic stress tolerance and/or resistance (water, drought, cold, salt, etc.), conferring xenobiotic stress tolerance and/or resistance, and development control (for example, yield, flowering time, etc.).

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify gene expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention.

In preferred embodiments, the invention provides methods for identifying the glycosylation sites inherent in the polynucleotides and polypeptides of the invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion In further preferred embodiments, methods are provided for evolving the polynucleotides and polypeptides of the present invention using molecular evolution in an effort to create and identify novel variants with desired structural, functional, and/or physical characteristics.

The present invention in further preferred embodiments provides for other experimental methods and procedures currently available to derive functional assignments. These procedures include but are not limited to spotting of clones on arrays, micro-array technology, PCR based methods and other procedures that could use sequence information from the clones to build a primer or a hybrid partner.

As used herein, the term "environmental stress" refers to any sub-optimal growing condition and includes, but is not limited to, sub-optimal conditions associated with salinity, drought, temperature, metal, chemical, pathogenic and oxidative stresses, or combinations thereof. In preferred embodiments, the environmental stress can be salinity, drought, or temperature, or combinations thereof, and in particular, can be high salinity, low water content or low temperature. It is also to be understood that as used in the specification and in the claims, "a" or "an" can mean one or more, depending upon the context in which it is used. Thus, for example, reference to "a cell" can mean that at least one cell can be utilized.

As also used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR and in vitro or in vivo transcription.

An "isolated" nucleic acid molecule is one that is substantially separated from other nucleic acid molecules which are present in the natural source of the nucleic acid (i.e., sequences encoding other polypeptides). Preferably, an "isolated" nucleic acid is free of some of the sequences which naturally flank the nucleic acid (i.e., sequences located at the 5' and 3' ends of the nucleic acid) in its naturally occurring replicon. For example, a cloned nucleic acid is considered isolated. In various embodiments, the isolated NA$^+$/H$^+$ ANTIPORTER nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparations or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

Preferred Polynucleotides and Polypeptides of the Invention

Features of the Polypeptides

The polypeptides of genes provided as SEQ ID NO:2 and SEQ ID NO:5 (FIG. 3), encoded by the polynucleotide sequence according to SEQ ID NO:1 and SEQ ID NO:3, and SEQ ID NO:4 (FIGS. 2A–D), and/or encoded by the polynucleotide contained within the clones, PpNHX1 and PpNHX2, have significant homology at the nucleotide and amino acid level to sodium anti-porters in *Oryza sativa* (Q9SXJ8, Q9SXJ8#2), *Caenorhabditis elegans* (Q9X14), *Drosophila melanogaster* (Q9VP1), and *Arabidopsis* (AtNHX1; BAB02053) (see FIGS. 4A–C, FIG. 5 and FIG. 8). Based upon the homology, the polypeptide of the present invention may share at least some biological activity with Na$^+$/H$^+$ antiporters. The polynucleotides and polypeptides of the present invention, including agonists and/or fragments thereof, have uses that include, but are not limited to conferring drought tolerance and/or salt tolerance to plants. Moreover, the polynucleotides and polypeptides of the present invention may also be useful in increasing the cultivatable range of crops within high salinity soils.

The polypeptide of the present invention has been shown to comprise a sodium binding site (See FIG. 4). Such a binding site is also known as an amilolide binding site.

In prefered embodiments, the following polypeptide is encompassed by the present invention: ILEFDEELFFIYLL-PPIIFNAGFQVKKKEFFRNFITTMFF (SEQ ID NO:13). Polynucleotide encoding this polypeptide is also provided.

The polypeptide of the present invention has also been shown to comprise a FKBP-type peptidyl-prolyl cis-trans isomerase domain. FKBP [1,2,3] is the major high-affinity binding protein, in vertebrates, for the immunosuppressive drug FK506. It exhibits peptidyl-prolyl cis-trans isomerase activity (EC 5.2.1.8) PPIase or rotamase). PPIase is an enzyme that accelerates protein folding by catalyzing the cis-trans isomerization of proline imidic peptide bonds in oligopeptides [4]. At least three different forms of FKBP are known in mammalian species: FKBP-12, which is cytosolic and inhibited by both FK506 and rapamycin; FKBP-13, which is membrane associated and inhibited by both FK506 and rapamycin; and FKBP-25, which is preferentially inhibited by rapamycin. The following publications are referenced above and are hereby incorporated herein in their entirety: [1] Tropschug M., Wachter E., Mayer S., Schoenbrunner E. R, Schmid F. X., Nature 346:674–677(1990); [2] Stein R. L., Curr. Biol. 1:234–236(1991); [3] Siekierka J. J., Widerrecht G., Greulich H., Boulton D., Hung S. H. Y., Cryan J., Hodges P. J., Sigal N. H., J. Biol. Chem. 265: 21011–21015(1990); and [4] Fischer G., Schmid F. X., Biochemistry 29:2205–2212(1990).

Based upon the presence of the FKBP-type peptidyl-prolyl cis-trans isomerase domain, the polypeptide of the present invention may share at least some biological activity with FKBP-type peptidyl-prolyl cis-trans isomerase domain containing proteins.

In prefered embodiments, the following polypeptide is encompassed by the present invention: QDETPLLYSLVF-GEGVVNDATSVVLS (SEQ ID NO:14). Polynucleotide encoding this polypeptide is also provided.

Although it is believed the encoded polypeptides may share at least some biological activities with $Na^+/H^+$ antiporters, a number of methods of determining the exact biological function of this clone are either known in the art or are described elsewhere herein. Briefly, the function of these clones may be construed by applying microarray methodology. The PpNHX1 and PpNHX2 clones in addition to other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been cold treated might indicate a function in modulating cold tolerance, for example. In the case of PpNHX1 and PpNHX2, tissue deprived of water or stressed by other biotic or abiotic stresses (heat, drought, high light, high salt, etc.) should be used to extract RNA to prepare the probe.

In addition, the function of the protein may be assessed by applying quantitative PCR methodology, for example. Real time quantitative PCR would provide the capability of following the expression of specific genes throughout the plant development cycle, for example. Quantitative PCR methodology requires only a nominal amount of tissue from each developmentally important step (3 days germinated seedlings, 1 week old seedlings [roots, shoots, and stems]; roots, leaves and stems before the onset of flowering, flowers [different parts]; and/or developing embryos) is needed to perform such experiments. Therefore, the application of quantitative PCR methodology to refining the biological function of this polypeptide is encompassed by the present invention. Also encompassed by the present invention are quantitative PCR probes corresponding to the polynucleotide sequence provided as SEQ ID NO:1 and SEQ ID NO: 3 and 4 (FIGS. 2A–D).

The function of the protein may also be assessed through complementation assays in yeast For example, in the case of the PpNHX1 and PpNHX2 clones, transforming yeast deficient in sodium antiporter activity and assessing their ability to grow in high salinity conditions would provide additional evidence the PpNHX1 and PpNHX2 clones have sodium antiporter activity. Alternatively, transforming wild type yeast with the PpNHX1 and PpNHX2 clones under increasing salinity conditions and assessing the ability of the transformed yeast to grow on media containing higher concentrations than non-transformed yeast could also establish the sodium antiporter activity of PpNHX1 and PpNHX2 clones, in addition to its increased sodium transport efficiency. Additional assay conditions and methods that may be used in assessing the function of the polynucletides and polypeptides of the present invention are known in the art, some of which are disclosed elsewhere herein.

Alternatively, a biological function of the encoded polypeptide may be determined by disrupting a homologue of these polypeptides in *Synecosystis*. Cyanobacteria (blue-green algae) is considered a precursor to the plant chloroplast. It possesses both photosynthetic systems and many other metabolic processes reminiscent to those of plants. These processes are often targets for many commercial herbicides, and this organism has been widely used in the study of the mode of action of many classes of herbicides. *Synechocystis* is one of the best-studied cyanobacteria. In addition to most of the features common to cyanobacteria, it offers many other added advantages. *Synechocystis* has a naturally occurring genetic transformation system, thus entailing vigorous and sophisticated genetic and molecular manipulation (e.g. targeted-gene disruption, gene replacement, etc.) applicable to some of the well-characterized systems (*S. cerevisiae, E. coli*). Most importantly, the availability of the complete genomic sequence information of the *Synechocystis* affords an avenue for the rapid identification and cloning of gene(s) of interest, and elucidation of gene function through genetic and molecular means.

Moreover, a biological function of these polypeptides may be determined by the application of antisense and/or sense methodology and the resulting generation of transgenic plants. Expressing a particular gene in either sense or antisense orientation in a transgenic plant can lead to respectively higher or lower expression levels of that particular gene. Altering the endogenous expression levels of a gene can lead to the observation of a particular phenotype that can then be used to derive indications on the function of the gene. These genes can be either over-expressed or under expressed in every cell of the plant at all times using a strong ubiquitous promoter, or it can be expressed in one or more discrete parts of the plant using a well characterized tissue-specific promoter (i.e., a root promoter or a flower specific promoter), or it can be expressed at a specified time of development using an inducible and/or a developmentally regulated promoter.

In the case of PpNHX1 and PpNHX2 transgenic plants, if no phenotype is apparent in normal growth conditions, observing the plants under stress conditions (deprivation of water, presence of high salt, OT other biotic or abiotic stresses, such as cold, heat, drought, high light, etc.) may lead to understanding the function of the gene. Therefore, the application of antisense and/or sense methodology to the creation of transgenic plants to refine the biological function of the polypeptide is encompassed by the present invention.

In preferred embodiments, the following N-terminal deletion mutants are encompassed by the present invention: M1-S558, A2-S558, T3-S558, N4-S558, D5-S558, V6S558, V7-S558, S8-S558, V9-S558, S10-S558, H11-S558, S12-S558, M13-S558, L14-S558, L15-S558, K16-S558, A17-S558, T18-S558, D19-S558, L20-S558, K21-S558, D22-S558, D23-S558, R24-S558, 125-S558, D26-S558, V27-S558, I28-S558, S29-S558, 130-S558, C31-S558, L32-S558, F33-S558, V34-S558, F35-S558, L36-S558, L37-S558, C38-S558, A39-S558, C40-S558, 141-S558, V42-S558, L43-S558, G44-S558, H45-S558, L46-S558, L47-S558, E48-S558, E49-S558, N50-S558, R51-S558, W52-S558, M53-S558, N54-S558, E55-SS58, S56-S558, 157-S558, T58-S558, A59-S558, L60-S558, L61-SS58, L62-S558, G63-S558, L64-S558, F65-S558, T66-S558, G67-S558, S68-S558, 169-S558, V70-S558, L71-S558, 172-S558, S73-S558, S74-S558, K75-S558, G76-S558, Q77-S558, G78-S558, S79-S558, H80-S558, I81-S558, L82-S558, E83-S558, F8SS558, D85-S558, E86-S558, E87-S558, L88-S558, F89-S558, F90-S558, 191-S558, Y92-

S558, L93-S558, L94-S558, P95-S558, P96-S558, I97-S558, I98-S558, F99-S558, N100-S558, A101-S558, G102-S558, F103-S558, Q104-S558, V105-S558, K106-S558, K107-S558, K108-S558, E109-S558, F110-S558, F111-S558, R112-S558, N113-S558, F114-S558, I115-S558, T116-S558, I117-S558, M118-S558, F119-S558, F120-S558, G121-S558, V122-S558, I123-S558, G124-S558, V125-S558, F126-S558, I127-S558, S128-S558, F129-S558, G130-S558, I131-S558, I132-S558, S133-S558, T134-S558, G135-S558, S136-S558, W137-S558, Y138-S558, F139-S558, F140-S558, S141-S558, K142-S558, F143-S558, G144-S558, L145-S558, K146-S558, N147-S558, L148-S558, P149-S558, I150-S558, R151-S558, D152-S558, 1153558, L154-S558, A155-S558, I156-S558, G157-S558, V158-S558, 1159-S558, F160-S558, S161-S558, A162-S558, T163-S558, D164-S558, S165-S558, V166-S558, C167-S558, T168-S558, L169-S558, Q170-S558, V171-S558, L172-S558, N173-S558, Q174-S558, D175-S558, E176-S558, T177-S558, P178-S558, L179-S558, L180-S558, Y181-S558, S182-S558, L183-S558, V184-S558, F185-S558, G186-S558, E187-S558, G188-S558, V189-S558, V190-S558, N191-S558, D192-S558, A193-S558, T194-S558, S195-S558, V196-S558, V197-S558, L198-S558, S199-S558, R200-S558, A201-S558, V202-S558, Q203-S558, T204-S558, Y205-S558, N206-S558, F207-S558, D208-S558, N209-S558, F210-S558, T211-S558, S212-S558, L213-S558, E214-S558, G215-S558, L216-S558, Q217-S558, 1218-S558, G219-S558, G220-S558, S221-S558, F222-S558, L223-S558, Y224-S558, L225-S558, F226-S558, F227-S558, S228-S558, S229-S558, C230-S558, I231-S558, L232-S558, G233-S558, I234-S558, A235-S558, S236-S558, G237-S558, L238-S558, 1239-S558, S240-S558, A241-S558, Y242-S558, I243-S558, I244-S558, K245-S558, T246-S558, M247-S558, Y248-S558, F249-S558, G250-S558, R251-S558, H252-S558, S253-S558, T254-S558, D255-S558, R256-S558, E257-S558, I258-S558, A259-S558, I260-S558, M261-S558, T262-S558, L263-S558, M264-S558, A265-S558, Y266-S558, L267-S558, S268-S558, Y269-S558, V270-S558, F271-S558, A272-S558, E273-S558, L274-S558, F275-S558, Y276-S558, L277-S558, S278-S558, G279-S558, I280-S558, L281-S558, S282-S558, V283-S558, F284-S558, F285-S558, C286-S558, G287-S558, I288-S558, V289-S558, M290-S558, S291-S558, H292-S558, Y293-S558, T294-S558, W295-S558, H296-S558, N297-S558, V298-S558, T299-S558, E300-S558, N301-S558, S302-S558, R303-S558, I304S558, T305-S558, S306-S558, K307-S558, H308-S558, S309-S558, F310-S558, A311-S558, T312-S558, M313-S558, S314-S558, F315-S558, 1316-S558, A317-S558, E318-S558, T319-S558, F320-S558, I321-S558, F322-S558, L323-S558, Y324-S558, V325-S558, G326-S558, M327-S558, D328-S558, A329-S558, L330-S558, D331-S558, F332-S558, E333-S558, K334-S558, W335-S558, K336-S558, M337-S558, M338-S558, Q339-S558, S340-S558, S341-S558, F342-S558, T343-S558, E344-S558, S345-S558, A346-S558, G347-S558, L348-S558, F349-S558, G350-S558, S351-S558, L352-S558, L353-S558, F354-S558, L355-S558, V356-S558, L357-S558, L358-S558, G359-S558, R360-S558, A361-S558, A362-S558, F363-S558, V364-S558, F365-S558, P366-S558, L367-S558, S368-S558, A369-S558, L370-S558, S371-S558, N372-S558, Y373-S558, S374S558, T375-S558, K376-S558, S377-S558, P378-S558, D379-S558, A380-S558, K381-S558, 1382-S558, N383-S558, L384-S558, R385-S558, Q386-S558, M387-S558, V388-S558, I389-S558, I390-S558, W391-S558, W392-S558, A393-S558, G394-S558, L395-S558, M396-S558, R397-S558, G398-S558, A399-S558, V400-S558, S401-S558, 1402-S558, A403-S558, L404-S558, A405-S558, F406-S558, N407-S558, Q408-S558, G409-S558, G410-S558, D411-S558, A412-S558, K413-S558, D414-S558, S415-S558, N416-S558, Q417-S558, A418-S558, T419-S558, L420-S558, M421-S558, V422-S558, I423-S558, T424-S558, I425-S558, I426-S558, 1427-S558, V428-S558, L429-S558, F430-S558, S431-S558, T432-S558, 1433-S558, V434-S558, F435-S558, G436-S558, T437-S558, A438-S558, T439-S558, K440-S558, P441-S558, L442-S558, 1443-S558, S444-S558, W445-S558, L446-S558, L447-S558, P448-S558, P449-S558, H450-S558, F451-S558, R452-S558, S453-S558, N454-S558, Y455-S558, S456-S558, D457-S558, S458-S558, A459-S558, S460-S558, L461-S558, S462-S558, P463-S558, K464-S558, A465-S558, S466-S558, L467-S558, D468-S558, A469-S558, D470-S558, F471-S558, H472-S558, I473-S558, P474-S558, L475-S558, L476-S558, M477-S558, D478-S558, T479-S558, E480-S558, R481-S558, E482-S558, E483-S558, L484-S558, E485-S558, A486-S558, N487-S558, D488-S558, R489-S558, S490-S558, T491-S558, 1492-S558, N493-S558, Q494-S558, I495-S558, L496-S558, N497-S558, G498-S558, L499-S558, S558, P500-S558, C501-S558, P502-S558, Q503-S558, S504-S558, I505-S558, G506-S558, M507-S558, L508-S558, L509-S558, T510-S558, A511-S558, P512-S558, R513-S558, S514-S558, T515-S558, I516-S558, H517-S558, H518-S558, V519-S558, W520-S558, R521-S558, K522-S558, F523-S558, D524-S558, D525-S558, S526-S558, Y527-S558, M528-S558, R529-S558, P530-S558, T531-S558, F532-S558, G533-S558, G534-S558, R535-S558, G536-S558, Y537-S558, V538-S558, R539-S558, L540-S558, V541-S558, S542-S558, R543-S558, R544-S558, D545-S558, M546-S558, D547-S558, 1548-S558, Q549-S558, E550-S558, D551-S558, E552-S558, of SEQ ID NO:2. Polynucleotide sequences encoding these polypeptides are also provided.

In preferred embodiments, the following C-terminal deletion mutants are encompassed by the present invention: M1-S558, M1-H557, M1-D556, M1-E555, M1-L554, M1-I553, M1-E552, M1-D551, M1-E550, M1-Q549, M1-I548, M1-D547, M1-M546, M1-D545, M1-R544, M1-R543, M1-S542, M1-V541, M1-L540, M1-R539, M1-V538, M1-Y537, M1-G536, M1-R535, M1-G534, M1-G533, M1-F532, M1-T531, M1-P530, M1-R529, M1-M528, M1-Y527, M1-S526, M1-D525, M1-D524, M1-F523, M1-K522, M1-R521, M1-W520, M1-V519, M1-H518, M1-H517, M1-I516, M1-T515, M1-S514, M1-R513, M1-P512, M1-A511, M1-T510, M1-L509, M1-L508, M1-M507, M1-G506, M1-I505, M1-S504, M1-Q503, M1-P502, M1-C501, M1-P500, M1-L499, M1-G498, M1-N497, M1-L496, M1-I495, M1-Q494, M1-N493, M1-I492, M1-T491, M1-S490, M1-R489, M1-D488, M1-N487, M1-A486, M1-E485, M1-L484, M1-E483, M1-E482, M1-R481, M1-E480, M1-T479, M1-D478, M1-M477, M1-L476, M1-L475, M1-P474, M1-I473, M1-H472, M1-F471, M1-D470, M1-A469, M1-D468, M1-L467, M1-S466, M1-A465, M1-K464, M1-P463, M1S462, M1-L461, M1-S460, M1-A459, M1-S458, M1-D457, M1-S456, M1-Y455, M1-N454, M1-S453, M1-R452, M1-F451, M1-H450, M1-P449, M1-P448, M1-L447, M1-L446, M1-W445, M1-S444, M1-I443, M1-L442, M1-P441, M1-K440, M1-T439, M1-A438, M1-T437, M1-G436, M1-F435, M1-V434, M1-I433, M1-T432, M1-S431, M1-F430, M1-L429, M1-V428, M1-I427, M1-I426, M1-I425, M1-T424, M1-I423, M1-V422, M1-M421, M1-L420, M1-T419, M1-A418, M1-Q417, M1-N416, M1-S415, M1-D414, M1-K413, M1-A412, M1-D411, M1-G410, M1-G409, M1-Q408, M1-N407, M1-F406, M1-A405, M1-L404, M1-A403, M1-I402, M1-S401, M1-V400, M1-V399, M1-G398, M1-R397, M1-M396, M1-L395, M1-G394, M1-A393, M1-W392, M1-W391, M1-I390, M1-I389, M1-V388, M1-M387, M1-Q386, M1-R385, M1-L384, M1-N383, M1-I382, M1-K381, M1-A380, M1-D379, M1-P378, M1-S377, M1-K376, M1-T375, M1-S374, M1-Y373, M1-N372, M1-S371, M1-L370, M1-A369, M1-S368, M1-L367, M1-P366, M1-F365, M1-V364, M1-F363, M1-A362, M1-A361, M1-R360, M1-G359, M1-L358, M1-L357, M1-V356, M1-L355, M1-F354, M1-L353, M1-L352, M1-S351, MI-350, M1-F349, M1-L348, M1-G347, M1-A346, M1-S345, M1-E344, M1-T343, M1-F342, M1-S341, M1-S340, M1-Q339, M1-M338, M1-M337, M1-K336, M1-W335, M1-K334, M1-E333, M1-F332, M1-D331, M1-L330, M1-A329, M1-D328, M1-M327, M1G326, M1-V325, M1-Y324, M1-L323, M1-F322, MI-1321, M1-F320, MI-T-319, M1-E318, M1-A317, M1-I316, M1-F315, M1-S314, M1-M313, M1-T312, M1-A311, M1-F310, M1-S309, M1-H308, M1-K307, M1-S306, M1-T305, M1-I304, M1-R303, M1-S302, M1-N301, M1-E300, M1-T299, M1-V298, M1-N297, M1-H296, M1-W295, M1-T294, M1-Y293, M1-H292, M1-S291, M1-M290, M1-V289, M1-I288, M1-G287, M1-C286, M1-F285, M1-F284, M1-V283, M1-S282, M1-L281, M1-I280, M1-G279, M1-S278, M1-L277, M1-Y276, M1-F275, M1-L274, M1-E273, M1-A272, M1-F271, M1-V270, M1-Y269, M1-S268, M1-L267, M1-Y266, M1-A265, M1-M264, M1-L263, M1-T262, M1-M261, MI-1260, M1-A259, M1-I258, M1-E257, M1-R256, M1-D255, M1-T254, M1-S253, M1-H252, M1-R251, M1-G250, M1-F249, M1-Y248, M1-M247, M1-T246, M1-K245, M1-I244, M1-I243, M1-Y242, M1-A241, M1-S240, M1-I239, M1-L238, M1-G237, M1-S236, M1-A235, M1-I234, M1-G233, M1-L232, M1-I231, M1-C230, M1-S229, M1-S228, M1-F227, M1-F226, M1-L225, M1-Y224, M1-L223, M1-F222, M1-S221, M1-G220, M1-G219, M1-I218, M1-Q217, M1-L216, M1-G215, M1-E214, M1-L213, M1-S212, M1-I211, M1-F210, M1-N209, M1-D208, M1-F207, M1-N206, M1-Y205, M1-T204, M1-Q203, M1-V202, M1-A201, M1-R200, M1-S199, M1-L198, M1-V197, M1-V196, M1-S195, M1-T194, M1-A193, M1-D192, M1-N191, M1-V190, M1-V189, M1-G188, M1-E187, M1-G186, M1-F185, M1-V184, M1-L183, M1-S182, M1-Y181, M1-L180, M1-L179, M1-P178, M1-T177, M1-E176, M1-D175, M1-Q174, M1-N173, M1-L172, M1-V171, M1-Q170, M1-L169, M1-T168, M1-C167, M1-V166, M1-S165, M1-D164, M1-T163, M1-A162, M1-S161, M1-F160, M1-I159, M1-V158, M1-G157, M1-I156, M1-A155, M1-L154, M1-I153, M1-D152, M1-R151, M1-I150, M1-P149, M1-L148, M1-N147, M1-K146, M1-L145, M1-G144, M1-F143, M1-K142, M1-S141, M1-F140, M1-F139, M1-Y138, M1-W137, M1-S136, M1-G135, M1-T134, M1-S133, M1-I132, M1-I131, M1-G130, M1-F129, M1-S128, M1-I127, M1-F126, M1-V125, M1-G124, M1-I123, M1-V122, M1-G121, M1-F120, M1-F119, M1-M118, M1-I117, M1-T116, M1-I115, M1-F114, M1-N113, M1-R112, M1-F111, M1-F110, M1-E109, M1-K108, M1-K107, M1-K106, M1-V105, M1-Q104, M1-F103, M1-G102, M1-A110, M1-N100, M1-F99, M1-I98, M1-L97, M1-P96, M1-P95, M1-L94, M1-L93, M1-Y92, M1-I91, M1-F90, M1-F89, M1-L88, M1-E87, M1-E86, M1-D85, M1-F84, M1-E83, M1-L82, M1-I81, M1-H80, M1-S79, M1-G78, M1-Q77, M1-G76, M1-K75, M1-S74, M1-S73, M1-I72, M1-L71, M1-V70, M1-I69, M1-S68, M1-G67, M1-T66, M1-F65, M1-L64, M1-G63, M1-L62, M1-L61, M1-L60, M1-A59, M1-T58, M1-I57, M1-S56, M1-E55, M1-N54, M1-M53, M1-W52, M1-R51, M1-N50, M1-E49, M1-E48, M1-L47, M1-L46, M1-H45, M1-G44, M1-L43, M1-V42, M1-I41, M1-C40, M1-A39, M1-C38, M1-L37, M1-L36, M1-F35, M1-V34, M1-F33, M1-L32, M1-C31, M1-I30, M1-S29, M1-I28, M1-V27, M1-D26, M1-I25, M1-R24, M1-D23, M1-D22, M1-K21, M1-L20, M1-D19, M1-T18, M1-A17, M1-K16, M1-L15, M1-L14, M1-M13, M1-S12, M1-H11, M1-S10, M1-V9, M1-S8, M1-V7, of SEQ ID NO:2. Polynucleotide sequences encoding these polypeptides are also provided.

Many polynucleotide sequences, such as EST sequences, are publicly available and accessible through sequence databases. Some of these sequences are related to SEQ ID NO: 1 and SEQ ID NO: 3 and SEQ ID NO: 4 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1677 of SEQ ID NO: 1, b is an integer between 15 to 1677, where both a and b correspond to the positions of nucleotide residues shown in SEQ ID NO:1, and where b is greater than or equal to a+14. Accordingly, preferably excluded from the present invention are one or more polynucleotides comprising a nucleotide sequence described by the general formula of a-b, where a is any integer between 1 to 2624 of SEQ ID NO: 4, b is an integer between 15 to 2624, where both a and b correspond to the positions of nucleotide residues shown in SEQ ID NO: 4, and where b is greater than or equal to a+14.

TABLE 1

| Gene No. | CDNA Clone ID | ATCC Deposit NO:Z | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|---|
| 1. | PpNHX1 | Acc. No xxx | pCR2.1 | 1 | 1677 | 1 | 1674 | 2 | 558 |
| 2. | PpNHX2 | Acc. No xxx | pCR2.1 | 4 | 2624 | 14 | 2564 | 5 | 849 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually several overlapping sequences at each nucleotide position), resulting in a final sequence identified as SEQ ID NO:X.

The cCDA Clone ID was deposited and given the accession number and date provided in Table 1, referred to collectively herein as ATCC Deposit No:Z. "Vector" refers to the type of vector contained in the cDNA Clone ID. pCR2.1 was obtained from Invitrogen, Inc.

"Total NT Seq. Of Clone" refers to the total number of nucleotides in the clone contig identified by "Gene No." The deposited clone may contain all or most of the sequence of SEQ ID NO:X. The nucleotide position of SEQ ID NO:X of the putative start codon (methionine) is identified as "5' NT of Start Codon of ORF."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The total number of amino acids within the open reading frame of SEQ ID NO:Y is identified as "Total AA of ORF".

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides may cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a cDNA of the invention as set forth in Table 1. The nucleotide sequence of each clone can readily be determined by sequencing the clone in accordance with known methods. The predicted amino acid sequence can then be verified. Moreover, the amino acid sequence of the protein encoded by a particular clone can also be directly determined by peptide sequencing or by expressing the protein in a suitable host cell containing the cDNA, collecting the protein, and determining its sequence.

The present invention also relates to the genes corresponding to SEQ ID NO:X, SEQ ID NO:Y, or the clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs, allelic variants, and/or orthologs. The skilled artisan could, using procedures well-known in the art, obtain the polynucleotide sequence corresponding to full-length genes (including, but not limited to the full-length coding region), allelic variants, splice variants, orthologs, and/or species homologs of genes corresponding to SEQ ID NO:X, SEQ ID NO:Y, or a deposited clone, relying on the sequence from the sequences disclosed herein or the clones deposited with the ATCC. For example, allelic variants and/or species homologs may be isolated and identified by making suitable probes or primers which correspond to the 5', 3', or internal regions of the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the fill-length protein, including the mature form (if applicable), or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the full-length polypeptide, can be substantially purified using techniques described herein or otherwise known in the art, such as, for example, by the one-step method described in Smith and Johnson, Gene 67:31–40 (1988). Polypeptides of the invention also can be purified from natural, synthetic or recombinant sources using protocols described herein or otherwise known in the art, such as, for example, antibodies of the invention raised against the mature and/or full-length form of the protein.

The present invention provides a polynucleotide comprising, or alternatively consisting of, the sequence identified as SEQ ID NO:X, and/or a cDNA provided in ATCC Deposit No. Z:. The present invention also provides a polypeptide comprising, or alternatively consisting of, the sequence identified as SEQ ID NO:Y, and/or a polypeptide encoded by the cDNA provided in ATCC Deposit NO:Z. The present invention also provides polynucleotides encoding a polypeptide comprising, or alternatively consisting of the polypeptide sequence of SEQ ID NO:Y, and/or a polypeptide sequence encoded by the cDNA contained in ATCC Deposit No:Z.

Preferably, the present invention is directed to a polynucleotide comprising, or alternatively consisting of, the sequence identified as SEQ ID NO:X, and/or a cDNA provided in ATCC Deposit No.:Z that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences may be complementary to the sequence disclosed as SEQ ID NO:X, the sequence contained in a deposit, and/or the nucleic acid sequence encoding the sequence disclosed as SEQ ID NO:Y.

The present invention also encompasses polynucleotides capable of hybridizing, preferably under reduced stringency conditions, more preferably under stringent conditions, and most preferably under highly stingent conditions, to polynucleotides described herein. Examples of stringency conditions are shown in Table 2 below: highly stringent conditions are those that are at least as stringent as, for example, conditions A–F; stringent conditions are at least as stringent as, for example, conditions G–L; and reduced stringency conditions are at least as stringent as, for example, conditions M–R.

TABLE 2

| Stringency Condition | Polynucleotide Hybrid± | Hybrid Length (bp)‡ | Hyridization Temperature and Buffer† | Wash Temperature and Buffer† |
| --- | --- | --- | --- | --- |
| A | DNA:DNA | > or equal to 50 | 65° C.; 1xSSC -or- 42° C.; 1xSSC, 50% formamide | 65° C.; 0.3xSSC |
| B | DNA:DNA | <50 | Tb*; 1xSSC | Tb*; 1xSSC |
| C | DNA:RNA | > or equal to 50 | 67° C.; 1xSSC -or- 45° C.; 1xSSC, 50% formamide | 67° C.; 0.3xSSC |
| D | DNA:RNA | <50 | Td*; 1xSSC | Td*; 1xSSC |
| E | RNA:RNA | > or equal to 50 | 70° C.; 1xSSC -or- 50° C.; 1xSSC, 50% formamide | 70° C.; 0.3xSSC |
| F | RNA:RNA | <50 | Tf*; 1xSSC | Tf*; 1xSSC |
| G | DNA:DNA | > or equal to 50 | 65° C.; 4xSSC -or- 45° C.; 4xSSC, 50% formamide | 65° C.; 1xSSC |
| H | DNA:DNA | <50 | Th*; 4xSSC | Th*; 4xSSC |
| I | DNA:RNA | > or equal to 50 | 67° C.; 4xSSC -or- 45° C.; 4xSSC, 50% formamide | 67° C.; 1xSSC |
| J | DNA:RNA | <50 | Tj*; 4xSSC | Tj*; 4xSSC |
| K | RNA:RNA | > or equal to 50 | 70° C.; 4xSSC -or- 40° C.; 6xSSC, 50% formamide | 67° C.; 1xSSC |
| L | RNA:RNA | <50 | Tl*; 2xSSC | Tl*; 2xSSC |
| M | DNA:DNA | > or equal to 50 | 50° C.; 4xSSC -or- 40° C. 6xSSC, 50% formamide | 50° C.; 2xSSC |
| N | DNA:DNA | <50 | Tn*; 6xSSC | Tn*; 6xSSC |
| O | DNA:RNA | > or equal to 50 | 55° C.; 4xSSC -or- 42° C.; 6xSSC, 50% formamide | 55° C.; 2xSSC |

TABLE 2-continued

| Stringency Condition | Polynucleotide Hybrid± | Hybrid Length (bp)‡ | Hyridization Temperature and Buffer† | Wash Temperature and Buffer† |
|---|---|---|---|---|
| P | DNA:RNA | <50 | Tp*; 6xSSC | Tp*; 6xSSC |
| Q | RNA:RNA | > or equal to 50 | 60° C.; 4xSSC -or- 45° C.; 6xSSC, 50% formamide | 60° C.; 2xSSC |
| R | RNA:RNA | <50 | Tr*; 4xSSC | Tr*; 4xSSC |

‡The "hybrid length" is the anticipated length for the hybridized region(s) of the hybridizing polynucleotides. When hybridizing a polynucletotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., MegAlign program of the DNA*Star suite of programs, etc).
†SSPE (1xSSPE is 0.15M NaCl, 10 mM NaH2PO4, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete. The hyridizations and washes may additionally include 5X Denhardt's reagent, .5–1.0% SDS, 100 ug/ml denatured, fragmented salmon sperm DNA, 0.5% sodium pyrophosphate, and up to 50% formamide.
*Tb–Tr: The hybridization temperature for hybrids anticipated to be less than 50 base pairs in length should be 5–10° C. less than the melting temperature Tm of the hybrids there Tm is determined according to the following equations. For hybrids less than 18 base pairs in length, Tm (° C.) = 2 (# of A + T bases) + 4 (# of G + C bases). For hybrids between 18 and 49 base pairs in length, Tm (° C.) = 81.5 + 16.6 ($\log_{10}$[Na+]) + 0.41 (% G + C) − (600/N), where N is the number of bases in the hybrid, and [Na+] is the concentration of sodium ions in the hybridization buffer ([NA+] for 1xSSC = .165 M).
±The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds, John Wiley and Sons, Inc., sections 2.10 and 6.3–6.4, which are hereby incorporated by reference herein.

Preferably, such hybridizating polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while g sequence gaps. The determination of identity is well known in the art, and discussed more specifically elsewhere herein.

The invention encompasses the application of PCR methodology to the polynucleotide sequences of the present invention, the clone deposited with the ATCC, and/or the cDNA encoding the polypeptides of the present invention. PCR techniques for the amplification of nucleic acids are described in U.S. Pat. No. 4,683,195 and Saiki et al., Science, 239:487–491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al;., Cold Spring Harbor Symp. Quant. Biol., 51:263, (1987), Ehrlich (ed), PCR Technology, Stockton Press, NY, 1989; Ehrlich et al., Science, 252:1643–1650, (1991); and "PCR Protocols, A Guide to Methods and Applications", Eds., Innis et al., Academic Press, New York, (1990).

Signal Sequences

The present invention also encompasses mature forms of the polypeptide comprising, or alternatively consisting of, the polypeptide sequence of SEQ ID NO:Y, the polypeptide encoded by the polynucleotide described as SEQ ID NO:X and/or the polypeptide sequence encoded by a cDNA in the deposited clone. The present invention also encompasses polynucleotides encoding mature forms of the present invention, such as, for example the polynucleotide sequence of SEQ ID NO:X and/or the polynucleotide sequence provided in a cDNA of the deposited clone.

According to the signal hypothesis, proteins secreted by eukaryotic cells have a signal or secretary leader sequence which is cleaved from the mature protein once export of the growing protein chain across the rough endoplasmic reticulum has been initiated. Most eukaryotic cells cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, it is inherent in the amino acid sequence of the polypeptide.

Methods for predicting whether a protein has a signal sequence, as well as the cleavage point for that sequence, are available. For instance, the method of McGeoch, Virus Res.

3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

The established method for identifying the location of signal sequences, in addition, to their cleavage sites has been the SignalP program (v1.1) developed by Henrik Nielsen et al., Protein Engineering 10:1–6 (1997). The program relies upon the algorithm developed by von Heinje, though provides additional parameters to increase the prediction accuracy.

More recently, a hidden Markov model has been developed (H. Neilson, et al., Ismb 1998;6:122–30), which has been incorporated into the more recent SignalP (v2.0). This new method increases the ability to identify the cleavage site by discriminating between signal peptides and uncleaved signal anchors. The present invention encompasses the application of the method disclosed therein to the prediction of the signal peptide location, including the cleavage site, to any of the polypeptide sequences of the present invention.

As one of ordinary skill would appreciate, however, cleavage sites sometimes vary from organism to organism and cannot be predicted with absolute certainty. Accordingly, the polypeptide of the present invention may contain a signal sequence. Polypeptides of the invention which comprise a signal sequence have an N-terminus beginning within 5 residues (i.e., +or −5 residues, or preferrably at the −5, −4, −3, −2, −1, +1, +2, +3, +4, or +5 residue) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. Nonetheless, the present invention provides the mature protein produced by expression of the polynucleotide sequence of SEQ ID NO:X and/or the polynucleotide sequence contained in the cDNA of a deposited clone, in a mammalian cell (e.g., COS cells, as described below). These polypeptides, and the polynucleotides encoding such polypeptides, are contemplated by the present invention.

Polynucleotide and Polypeptide Variants

The present invention also encompases variants (e.g., allelic variants, orthologs, etc.) of the polynucleotide sequence disclosed herein in SEQ ID NO:X, the complementary strand thereto, and/or the cDNA sequence contained in the deposited clone.

The present invention also encompasses variants of the polypeptide sequence, and/or fragments therein, disclosed in SEQ ID NO:Y and/or encoded by a deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

The present invention is also directed to polynucleotide sequences which comprise, or alternatively consist of, a polynucleotide sequence which is at least 80%, 85%, 90%, 91%, 92%, 93%, 94%, 95%, 96%, 97%, 98%, or 99% identical to, the following non-limiting examples, the polynucleotide sequence of the coding region of the sequence in SEQ ID NO:X, the complementary strand of said coding region, the polynucleotide sequence provided in a cDNA of the deposited clone, the complementary strand of said deposited cDNA, a polynucleotide sequence encoding the polypeptide identified as SEQ ID NO:Y, a polynucleotide sequence encoding the polypeptide of a cDNA provided in the deposited clone. The invention also encompasses polynucleotide fragments of any of the polynucleotide sequences provided herein.

The present invention also encompasses polynucleotide sequences which hybridize to any of the provided polynucleotide sequences of the present invention, including the aforementioned polynucleotide fragments, under stringent or lower stringent hydrization conditions. Polypeptides encoded by the polynucleotide sequences which hybridize to the polynucleotide sequences of the present invention are also encompassed by the present invention.

The present invention encompasses polypeptide sequences which comprise, or alternatively consist of, an amino acid sequence which is at least 80%, 98%, 90%, 91%, 92%, 93%, 94%, 95%, 96%, 97%, 98%, or 99% identical to, the following non-limited examples, the polypeptide sequence identified as SEQ ID NO:Y, the polypeptide sequence encoded by a cDNA provided in the deposited clone, and/or polypeptide fragments of any of the polypeptides provided herein.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced in Table 1, the ORF (open reading frame), or any fragment specified as described herein.

As a practical matter, whether any particular nucleic acid molecule or polypeptide is at least 80%, 85%, 90%, 91%, 92%, 93%, 94%, 95%, 96%, 97%, 98%, or 99% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673–4680, (1994)), which is based on the algorithm of Higgins, D. G., et al., Computer Applications in the Biosciences (CABIOS), 8(2): 189–191, (1992). In a sequence alignment the query and subject sequences are both DNA sequences. An RNA sequence can be compared by converting U's to T's. The result of said global sequence alignment is in percent identity. Preferred parameters used in a CLUSTALW alignment of DNA sequences to calculate percent identity are: Matrix=BLOSUM, k-tuple=1, Number of Top Diagonals=5, Gap Penalty=3, Gap Open Penalty 10, Gap Extension Penalty=0, Scoring Method=Percent, Window Size=5 or the length of the subject nucleotide sequence, whichever is shorter.

If the subject sequence is shorter than the query sequence because of 5' or 3' deletions, not because of internal deletions, a manual correction must be made to the results. This is because the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score is what may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 91%, 92%, 93%, 94%, 95%, 96%, 97%, 98%, or 99% identical to, for instance, an amino acid sequence referenced in Table 1 (SEQ ID NO:Y) or to the amino acid sequence encoded by cDNA contained in a deposited clone, can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673–4680, (1994)), which is based on the algorithm of Higgins, D. G., et al., Computer Applications in the Biosciences (CABIOS), 8(2):189–191, (1992). In a sequence alignment the query and subject sequences are both DNA sequences. An RNA sequence can be compared by converting U's to T's. The result of said global sequence alignment is in percent identity. Preferred parameters used in a CLUSTALW alignment of DNA sequences to calculate percent identity are: Matrix=BLOSUM, k-tuple=1, Number of Top Diagonals-5, Gap Penalty=3, Gap Open Penalty 10, Gap Extension Penalty=0, Scoring Method=Percent, Window Size5 or the length of the subject nucleotide sequence, whichever is shorter.

If the subject sequence is shorter than the query sequence due to N- or C-terminal deletions, not because of internal deletions, a manual correction must be made to the results. This is because the CLUSTALW program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the CLUSTALW sequence alignment. This percentage is then subtracted from the percent identity, calculated by the above CLUSTALW program using the specified parameters, to arrive at a final percent identity score. This final percent identity score is what may be used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the CLUSTALW alignment does not show a matching/alignment of the first 10 residues at the N-terminus. The 10 unpaired residues represent 10% of the sequence (number of residues at the N- and C-terminus not matched/total number of residues in the query sequence) so 10% is subtracted from the percent identity score calculated by the CLUSTALW program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence, which are not matched/aligned with the query. In this case the percent identity calculated by CLUSTALW is not manually corrected. Once again, only residue positions outside the N- and C-terminal ends of the subject sequence, as displayed in the CLUSTALW alignment, which are not matched/aligned with the query sequence are manually corrected for. No other manual corrections are required for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as E. coli).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein (Dobeli et al., J. Biotechnology 7:199–216 (1988)).

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247: 1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include, but are not limited to, the following: (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art. From the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

Moreover, the invention further includes polypeptide variants created through the application of molecular evolution ("DNA Shuffling") methodology to the polynucleotide disclosed as SEQ ID NO:X, the sequence of the clone submitted in a deposit, and/or the cDNA encoding the polypeptide disclosed as SEQ ID NO:Y. Such DNA Shuffling technology is known in the art and more particularly described elsewhere herein (e.g., WPC, Stemmer, PNAS, 91:10747, (1994)), and example 39).

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

The present invention is directed to polynucleotide fragments of the polynucleotides of the invention, in addition to polypeptides encoded therein by said polynucleotides and/or fragments.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:X or the complementary strand thereto, or is a portion of a polynucleotide sequence encoding the polypeptide of SEQ ID NO:Y. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:X. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351400, 401450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:X, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of that contained in SEQ ID NO:Y or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the full-length protein. Further preferred polypeptide fragments include the full-length protein having a continuous series of deleted residues from the amino or the carboxy terminus, or both. For example, any number of amino acids, ranging from 1–60, can be deleted from the amino terminus of the full-length polypeptide. Similarly, any number of amino acids, ranging from 1–30, can be deleted from the carboxy terminus of the full-length protein. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the fill-length protein, the fragments ability to interact with at lease one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

Epitopes and Antibodies

In the present invention, "epitopes" refer to polypeptide fragments having antigenic and/or immunogenic activity in an organism, preferably an animal or a plant A preferred embodiment of the present invention relates to a polypeptide fragment comprising an epitope, as well as the polynucleotide encoding this fragment. A region of a protein molecule to which an antibody can bind is defined as an "antigenic epitope". In contrast, an "immunogenic epitope" is defined as a part of a protein that elicits an antibody reponse (i.e., in animals), or a defensive response (i.e., in plants). (See, for instance, Geyson et al., Proc. Natl. Aced. Sci. USA 81:3998–4002 (1983)).

Epitope fragments may be produced by any conventional means known in the art Epitopes that are immunogenic may be useful for inducing antibodies according to methods well known in the art. Such epitopes may be presented together with a carrier protein such as an albumin, or may be presented without a carrier if the epitope is of sufficient length (greater than or equal to 25 amino acids). Nonetheless, epitopes have been found to elicit an immune response that comprise as few as 8 to 10 amino acids. Epitopes of the present invention may be linear epitopes derived from a denatured polypeptide (e.g., as found in Western blots).

In the present invention, antigenic epitopes preferably contain a sequence of at least seven, more preferably at least nine, and most preferably between about 15 to about 30 amino acids. Antigenic epitopes are useful to raise antibodies, including monoclonal antibodies, that specifically bind the epitope. (See, for instance, Wilson et al., Cell 37:767–778 (1984); Sutcliffe, J. G., et al., Science 219:660–666 (1983)).

As used herein, the term "antibody" (Ab) or "monoclonal antibody" (Mab) is meant to include intact molecules, as well as, antibody fragments (such as, for example, Fab and F(ab')$_2$ fragments) which are capable of specifically binding to protein. Fab and F(ab')$_2$ fragments lack the Fc fragment of intact antibody, clear more rapidly from the circulation of the animal or plant, and may have less nonspecific tissue binding than an intact antibody (Wahl et al., J. Nucl. Med 24:316–325 (1983)). Thus, these fragments are preferred, as well as the products of a FAB or other immunoglobulin expression library. Moreover, antibodies of the present invention include chimeric, single chain, and humanized antibodies.

The present invention is further directed to antibodies specific to polypeptides, polypeptide fragments, and polypeptide variants of the present invention. The antibodies of the present invention may include, but are not limited to, polyclonal, monoclonal, humanized, fully-human, monospecific, bispecific, trispecific, heteroconjugate, chimeric, single chain, variable light chain, variable heavy chain, one or more complementarity-determining regions (CDRs), phage-display derived antibodies (those derived from a Fab expression library, etc.), anti-idiotype antibodies, and those antibodies having enzymatic activity (i.e., catalytic antibodies). The antibodies of the present invention may be comprised of any of the currently known antibody isotypes (e.g., IgD, IgM, IgE, IgG, IgY, and IgA, etc.), the human IgA and IgG subclasses (e.g., IgG1, IgG2, IgG3, IgG4, IgA1, or IgA2), or the mouse IgA and IgG subclasses (e.g., IgG1, IgG2a, IgG2b, IgG3, IgA1, or IgA2.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, 2$^{nd}$ ed. (1988), which is hereby incorporated herein by reference in its entirety). Polyclonal antibodies can be raised in a mammal or bird, for example, by one or more injections of an immunizing agent and, if desired, an adjuvant. For the purposes of the invention, "immunizing agent" may be defined as a polypeptide of the invention, including fragments, variants, and/or derivatives thereof in addition to fusions with heterologous polypeptides and other forms of the polypeptides described herein.

Typically, the immunizing agent and/or adjuvant will be injected in the mammal by multiple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivitizing active chemical functional groups to both the polypeptide of the present invention and the immunogenic protein such that a convalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hybridoma methods, such as those described by Köhler and Milstein, Nature, 256:495 (1975) and U.S. Pat. No. 4,376,110, by Harlow, et al., Antibodies: A Laboratory Manual, (Cold spring Harbor Laboratory Press, $2^{nd}$ ed. (1988), by Hamerling, et al., Monoclonal Antibodies and T-Cell Hybridomas (Elsevier, N.Y., (1981)), or other methods known to the artisan. Other examples of methods which may be employed for producing monoclonal antibodies includes, but are not limited to, the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybrizoma cell (Goding, Monoclonal Antibodies: Principles and Practice, Academic Press, (1986), pp. 59–103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. As inferred throughout the specification, human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51–63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoabsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4,816,567. In this contex the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hydridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglubulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The antibodies of the present invention may further comprise humanized antibodies or fully-human (human) antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat, or rabbit having the desired specificity, affinity and capacity. In some instances, Fv framework residues of the human immunoglubulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522–525 (1986); Riechmann et al., Nature 332:323–329 (1988)1 and Presta, Curr. Op. Struct. Biol., 2:593–596 (1992).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522–525 (1986); Reichmann et al., Nature, 332:323–327 (1988); Verhoeyen et al., Science, 239:1534–1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analagous sites in rodent antibodies.

Human antibodies can also be produced using various techniques known in the art, including phage display libraries (Hoogenboom and Winter, J. Mol. Biol., 227:381 (1991); Marks et al., J. Mol. Biol., 222:581 (1991)). The techniques of cole et al., and Boerder et al., are also available for the preparation of human monoclonal antibodies (cole et al., Monoclonal Antibodies and Cancer therapy, Alan R. Riss, (1985); and Boerner et al., J. Immunol., 147(1):86–95, (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., Biotechnol., 10:779–783 (1992); Lonberg et al., Nature 368:856–859 (1994); Fishwild et al., Nature Biotechnol., 14:845–51 (1996); Neuberger, Nature Biotechnol., 14:826 (1996); Lonberg and Huszer, Intern. Rev. Immunol., 13:65–93 (1995).

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, both of which are incorporated herein by reference in their entirety.)

The antibodies of the present invention may be bispecific antibodies. Bispecific antibodies are monoclonal, preferrably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglubulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzymn, 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373;

and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl4-mercaptobutyrimidate and those disclosed, for example, in U.S. Pat. No. 4,676,980.

Uses for Antibodies Directed against Polypeptides of the Invention

The antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the sample is a tissue (e.g., animal, plant, etc.), biological fluid (e.g., blood, urine, phloem fluid, xylem fluid, plant secretion, etc.), biological extract (e.g., tissue or cellular homogenate, etc.), a protein microchip (e.g., See Arenkov P, et al., Anal Biochem., 278(2):123–131 (2000)), or a chromatography column, etc. And a second step involving the quantification of antibody bound to the substrate. Alternatively, the method may additionally involve a first step of attaching the antibody, either covalently, electrostatically, or reversably, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogenous or homogenous phases (Zola, Monoclonal Antibodies: A Manual of Techniques, CRC Press, Inc., (1987), pp 147–158). The antibodies used in the diagnostic assays can be labeled with a detectable moiety. The detectable moiety should be capable of producing, either directly or indirectly, a detectable signal. For example, the detectable moiety may be a radioisotope, such as 2H, 14C, 32P, or 125I, a florescent or chemiluminescent compound, such as fluorescein isothiocyanate, rhodamine, or luciferin, or an enzyme, such as alkaline phoshatase, beta-galactosidase, green flourescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219(1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobilized on a suitable support, such as a Sephadex resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response upon ingestion of certain antigens, particularly plant antigens. In an exemplary example, the tomato LEA lectin, from *Lycospersicum esculentum* has been shown to elicit a strong immune response when administered both orally and i.n. in mice. Thus, the administration to the mouse of antibodies directed against the LEA lectin may decrease or altogether eliminate an immune response to the LEA lectin as the LEA lectin could effectively be eliminated from circulation prior to eliciting an immune response (for example, See Lavelle E C, et al., Immunology. 99(1):30–7, (2000)). Likewise, one could envision cloning the gene encoding an antibody directed against a polypeptide of the present invention, said polypeptide having the potential to elicit an allergic and/or immune response in an organism, and transforming the organism with said antibody gene such that it is expressed (e.g., constitutively, inducibly, etc.) in the organism. Thus, the organism would effectively become resistant to an allergic response resulting from the ingestion or presence of such an immune/allergic reactive polypeptide. Detailed descriptions of therapeutic and/or gene therapy applications of the present invention are provided elsewhere herein.

Alternatively, antibodies of the present invention could be produced in a plant (e.g., cloning the gene of the antibody directed against a polypeptide of the present invention, and transforming a plant with a suitable vector comprising said gene for constitutive expression of the antibody within the plant), and the plant subsequently ingested by an animal, thereby conferring temporary immunity to the animal for the specific antigen the antibody is directed towards (See, for example, U.S. Pat. Nos. 5,914,123 and 6,034,298).

In another embodiment, antibodies of the present invention, preferably polyclonal antibodies, more preferably monoclonal antibodies, and most preferably single-chain antibodies, can be used as a means of inhibiting gene expression of a particular gene, or genes, in a plant or organism. See, for example, International Publication Number WO 00/05391, published Feb. 3, 2000, to Dow Agrosciences LLC. The application of such methods for the antibodies of the present invention are known in the art, and are more particularly described elsewhere herein (See, Examples 14 and 15).

In yet another embodiment, antibodies of the present invention may be useful for multimerizing the polypeptides of the present invention. For example, certain proteins may confer enhanced biological activity when present in a multimeric state (i.e., such enhanced activity may be due to the increased effective concentration of such proteins whereby more protein is available in a localized location).

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions.

The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Peptide moieties may be added to the polypeptide to facilitate purification. Such regions may be removed prior to final preparation of the polypeptide. Similarly, peptide cleavage sites can be introduced inbetween such peptide moieties, which could additionally be subjected to protease activity to remove said peptide(s) from the protein of the present invention. The addition of peptide moieties, including peptide cleavage sites, to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331: 84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of the constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hEL-5. (See, D. Bennett et al., J. Molecular Recognition 8:52–58 (1995); K. Johanson et al., J. Biol. Chem. 270: 9459–9471 (1995).)

Moreover, the polypeptides of the present invention can be fused to marker sequences (also referred to as "tags"). Due to the availability of antibodies specific to such "tags", purification of the fused polypeptide of the invention, and/or its identification is significantly facilitated since antibodies specific to the polypeptides of the invention are not required. Such purification may be in the form of an affinity purification whereby an anti-tag antibody or another type of affinity matrix (e.g., anti-tag antibody attached to the matrix of a flow-thru column) that binds to the epitope tag is present. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984)).

The skilled artisan would acknowledge the existance of other "tags" which could be readily substituted for the tags referred to supra for purification and/or identification of polypeptides of the present invention (Jones C., et al., J Chromatogr A. 707(1):3–22 (1995)). For example, the c-myc tag and the 8F9, 3C7, 6E10, G4m B7 and 9E10 antibodies thereto (Evan et al., Molecular and Cellular Biology 5:3610–3616 (1985)); the Herpes Simplex virus glycoprotein D (gD) tag and its antibody (Paborsky et al., Protein Engineering, 3(6):547–553 (1990), the Flag-peptide—i.e., the octapeptide sequence DYKDDDDK (SEQ ID NO:8), (Hopp et al., Biotech. 6:1204–1210 (1988); the KT3 epitope peptide (Martin et al., Science, 255:192–194 (1992)); a-tubulin epitope peptide (Skinner et al., J. Biol. Chem., 266:15136–15166, (1991)); the T7 gene 10 protein peptide tag (Lutz-Freyermuth et al., Proc. Natl. Sci. USA, 87:6363–6397 (1990)), the FITC epitope (Zymed, Inc.), the GFP epitope (Zymed, Inc.), and the Rhodamine epitope (Zymed, Inc.).

The present invention also encompasses the attachment of the coding region of a repeating series of up to nine argininine amino acids to a polynucleotide of the present invention. The invention also encompasses chemically derivitizing a polypeptide of the present invention with a repeating series of up to nine arginine amino acids. Such a tag, when attached to a polypeptide, has recently been shown to serve as a universal pass, allowing compounds access to the interior of cells without additional derivitization or manipulation (Wender, P., et al., unpublished data).

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivitized to attach hapten molecules (e.g., DNP, (Zymed, Inc.)). Due to the availability of monoclonal antibodies specific to such haptens, the protein could be readily purified using immunoprecination, for example.

Polypeptides of the present invention, including fragments and/or variants thereof, in addition to, antibodies directed against such polypeptides, fragments, and/or variants, may be fused to any of a number of known, and yet to be determined, toxins, such as ricin, saporin (Mashiba H, et al., Ann N Y Acad. Sci. 1999;886:233–5), HC toxin (Tonukari N J, et al., Plant Cell. 2000 February; 12(2): 237–248), BT endotoxin, or pseudomonias endotoxin. Such fusions could be used to deliver the toxins to desired tissues for which a ligand or a protein capable of binding to the polypeptides of the invention exists.

The invention encompasses the fusion of antibodies directed against polypeptides of the present invention, including variants and fragments thereof, to said toxins for delivering the toxin to specific locations in a cell to specific plant tissues, and/or to specific plant species. Such bifunctional antibodies are known in the art, though a review describing additional advantageous fusions, including citations for methods of production, can be found in P. J. Hudson, Curr. Opp. In Imm. 11:548–557, (1999); this publication, in addition to the references cited therein, are hereby incorporated by reference in their entirety herein. In this context, the term "toxin" may be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and genetic material. In view of the present disclosure, one skilled in the art could determine whether any particular "toxin could be used in the compounds of the present invention. Examples of suitable "toxins" listed above are exemplary only and are not intended to limit the "toxins" that may be used in the present invention.

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert of the present invention should be operatively linked to an appropriate promoter, such as the 35S promoter, the 34S promoter, CMV promoter, phage lambda PL promoter, the E. coli lac, trp, phoA and tac promoters, the SV40 early and late promoters and promoters of retroviral LTR5, to name a few. In addition, it may be desirable, or required, in some instances to have tissue-specific or cell type-specific promoters operably linked to a polynucleotide of the present invention. Examples of suitable plant-expressible promoters selectively expressed in particular tissues or cell types are well known in the art and include, but are not limited to, seed specific promoters (e.g., WO 89/03887), organ-primordia specific promoters (An et al., Plant Cell, 8:15–30, (1996)), stem-specific promoters (Keller et al., EMBO J., 7:3625–3633, (1988)), leaf specific promoters (Hudspeth et al., Plant Mol. Biol., 12:579–589, (1989)), mesophyl-specific promoters (such as the light inducible Rubisco promoters), root-specific promoters (Keller et al., Genes Devel., 3:1639–1646, (1989)), tuber-specific promoters (Keil et al., EMBO J., 8:1323–1330, (1989)), vascular tissue specific promoters (Peleman et al., Gene, 84:359–369, (1989)), meristem specific promoters (such as the promoter of the SHOOTMERISTEMLESS (STM) gene, Long, et al., Nature, 379:66–69, (1996)), primodia specific promoter (such as the Antirrhinum CycD3a gene promoter, Doonan et al., in "Plant Cell Division" (Francis, Duditz, and Inze, Eds), Portland Press, London, (1998)), anther specific promoters (WO 89/10396, WO 92/13956, and WO 92/13957), stigma-specific promoters (WO 91/02068), degiscence-zone specific promoters (WO 97/13865), seed-specific promoters (WO 89/03887), etc.

Additional promoters that may be operably linked to a polynucleotide of the present invention may be found in McElroy and Brettel, Tibtech, Vol. 12, February, 1994. Moreover, a number of promoters are currently being used for transformation of dicotyledonous plants. These promoters come from a variety of different sources. One group of commonly used promoters were isolated from *Agrobacterium tumefaciens*, where they function to drive the expression of opine synthase genes carried on the T-DNA segment that is integrated into the plant genome during infection. These promoters include the octopine synthase (ocs) promoter (L. Comai et al., 1985; C. Waldron et-al., 1985), the mannopine synthase (mas) promoter (L. Comai et al., 1985; K. E. McBride and K. R. Summerfelt, 1990) and the nopaline synthase (nos) promoter (M. W. Bevan et al., 1983; L. Herrera-Estrella et al., 1983, R T. Fraley et al., 1983, M. De Block et al., 1984;, R Hain et al., 1985). These promoters are active in a wide variety of plant tissue.

In addition, the promoters disclosed in the following publications may also be operably linked to a polynucleotide of the present invention: U.S. Pat. Nos. 5,623,067; 5,712,112; 5,723,751; 5,723,754; 5,723,757; 5,744,334; 5,750,385; 5,750,399; 5,767,363; 5,783,393; 5,789,214; 5,792,922; 5,792,933; 5,801,027; 5,804,694; 5,814,618; 5,824,857; 5,824,863; 5,824,865; 5,824,866; 5,824,872; and 5,929,302; and International Publication Nos. WO 97/49727, WO 98/00533, WO 98/03655, WO 98/07846, WO 98/08961, WO 98/08962, WO 98/10734, WO 98/16634, WO 98/22593, WO 98/38295, and WO 98/44097; and European Patent Application No. EP 0 846 770.

Several viral promoters are also used to, drive heterologous gene expression in dicots (J. C. Kridl and R. M. Goodman, 1986) and may be operably linked to a polynucleotide of the present invention. The Cauliflower Mosaic Virus 35S promoter is one of the promoters used most often for dicot transformation because it confers high levels of gene expression in almost all tissues (J. Odell et al., 1985; D. W. Ow et al., 1986; D. M. Shah et al., 1986). Modifications of this promoter are also used, including a configuration with two tandem 35S promoters (R. Kay et al.,1987) and the mas-35S promoter (L. Comai et al., 1990), which consists of the mannopine synthase promoter in tandem with the 35S promoter. Both of these promoters drive even higher levels of gene expression than a single copy of the 35S promoter. Other viral promoters that have been used include the Cauliflower Mosaic Virus 19S promoter (J. Paszkowski et al., 1984; E. Balazs et al.) and the 34S promoter from the figwort mosaic virus (M. Sanger et al., 1990).

Alternatively, the polynucleotide insert of the present invention could be operatively linked to any of a number of inducible promoters known in the art, which include, but are not limited to: tetracycline inducible promoters, small-molecule inducible promoters, light inducible promoters, chemical compounds (e.g., safeners, herbicides, glucocorticoids, etc.), abiotic stress inducible promoters (e.g., wounding, heavy metals, cold-sensitive promoters, heat-sensitive promoters, salt sensitive promoters, drought sensitive promoters, hypoxia inducible (such as those disclosed in EP1012317), etc.), biotic stress promoters (e.g., pathogen or pest infection including infection by fungi, viruses, bacteria, insects, nematodes, mycoplasms, and mycoplasma-like organisms, etc.). Examples of plant-expressible inducible promoters suitable for the invention are: nematode inducible promoters (such as those disclosed in WO 92/21757 and/or EP1007709), fungus inducible promoters (WO 93/19188, WO 96/28561), chemically inducible Arabidopsis PR-1 promoter (WO 98/03536), the inducible promoters disclosed in WO 98/45445, the inducible promoters disclosed in U.S. Pat. No. 5,804,693, the tomato soft fruit inducible promoter disclosed in U.S. Pat. No. 5,821,398, promoters inducible after application of glucocorticoids such as dexamethasone, or promoters repressed or activated after application of tetracyclin (Gatz et al., PNAS USA, 85:1394–1397, (1988)). Other suitable inducible promoters will be known to the skilled artisan.

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by tans-acting transcription factors. Preferably, the cis acting DNA sequence elements and transacting transcription factors are operable in plants. Further, the trans-acting transcription factors of such "artificial" promoters could also be "artificial" or chimeric in design themselves and could act as activators or repressors to said "artficial" promoter. For example, a chimeric promoter of the invention could comprise one or more, upstream activating sequences from the Octopine Synthase gene (OCS), matrix attachment regions (MAR), etc.

The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

The expression constructs may additionally comprise 5' leader sequences in the expression constructs. Such leader sequences can act to enhance translation. Translation leaders are known in the art and include: picornavirus leaders, for example, EMCV leader (Encephalomyocarditis 5' noncoding region) (Elroy-Stein, 0., Fuerst, T. R., and Moss, B. (1989) PNAS USA, 86:6126–6130); potyvirus leaders, for example, TEV leader (Tobacco Etch Virus) (Allison et al. (1986)); MDMV leader (Maize Dwarf Mosaic Virus) Virology, 154:9–20); and human immunoglobulin heavy-chain binding protein (BiP), (Macejak, D. G., and Sarnow, P. (1991) Nature, 353:90–94; untranslated leader from the coat protein mRNA of alfalfa mosaic virus (AMV RNA 4), (Jobling, S. A., and Gehrke, L., (1987) Nature, 325:622–625); tobacco mosaic virus leader (TW), (Gallie, D. R. et al. (1989) Molecular Biology of RNA, pages 237–256); and maize chlorotic mottle virus leader (MCNW) (Lommel, S. A. et al. (1991) Virology, 81:382–385). See also, Della-Cioppa et al. (1987) Plant Physiology, 8196506& Other methods known to enhance translation can also be utilized, for example, introns, and the like.

As indicated, the expression vectors will preferably include at least one selectable marker. Such markers include, but are not limited to, dihydrofolate reductase, G418 or neomycin resistance, kanamycin resistance, hygromycin resistance, bialaphos resistance, sulfonoamide resistance, stretomycin resistance, spectinomycin resistance, chlorosulfuron resistance, glyphosphate resistance, and methotrexate resistance, for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhiniurium cells; fungal cells, such as yeast cells (e.g., Saccharomyces cerevisiae or Pichia pastoris (ATCC Accession No. 201178)); insect cells such as Drosophila S2 and Spodoptera Sf9 cells; animal cells such as CHO, COS, 293, and Bowes melanoma cells; plant cells, and specifically plant cells and/or tissues derived from any of the plants listed in Table 3. Appropriate culture mediums and conditions for the above-described host cells are known in the art.

The polynucleotides and polypeptides of the present invention can be targeted to the chloroplast or amyloplast for expression. In this manner, the expression construct will additionally contain a polynucleotide sequence encoding a transit peptide operably linked to a polynucleotide of the present invention to direct the polynucleotide of the present invention to the chloroplasts. Such transit peptides are known in the art. See, for example, Von Heijne et al. (1991) Plant Mol. Biol. Rep. 9:104–126; Clark et al. (1989) J. Biol. Chem. 264:17544–17550; della-Cioppa et al. (1987) Plant Physiol. 84065060 R. omer et al. (1993) Biochem. Biophys. Res Commun. 196:1414–1421; and Shah et al. (1986) Science 233:478–481.

The expression construct may also comprise any other necessary regulators such as nuclear localization signals (Kalderon et al. (1984) Cell 39:499–509; and Lassner et al. (1991) Plant Molecular Biology 17:229–234); plant translational consensus sequences (Joshi, C. P. (1987) Nucleic Acids Research 15:6643 6653), introns (Luehrsen and Walbot (1991) Mol. Gen. Genet. 225:81–93) and the like, operably linked to a polynucleotide of the present invention.

The polynucleotide sequences encoding the proteins or polypeptides of the present invention may be particularly useful in the genetic manipulation of plants. In this manner, the polynucleotides of the invention are provided in expression cassettes for expression in the plant of interest Where appropriate, the gene(s) may be optimized for increased expression in the transformed plant. That is, the polynucleotides can be synthesized using plant preferred codons for improved expression specific to a particular species. Methods are available in the art for synthesizing plant preferred genes. See, for example, U.S. Pat. Nos. 5,380,831, 5,436, 391, and Murray et al. (1989) Nucleic Acids Res. 17:477–498, herein incorporated by reference.

Depending upon the species in which the DNA sequence of interest is to be expressed, it may be desirable to synthesize the sequence with plant preferred codons, or alternatively with chloroplast preferred codons. The plant preferred codons may be determined from the codons of highest frequency in the proteins expressed in the largest amount in the particular plant species of interest. See, EPA 0359472; EPA 0385962; WO 91/16432; Perlak et al. (1991) Proc. Natl. Acad. Sci. USA 88:3324–3328; and Murray et al. (1989) Nucleic Acids Research. In this manner, the polynucleotide sequences can be optimized for expression in any plant. It is recognized that all or any part of the gene sequence may be optimized or synthetic. That is, synthetic or partially optimized sequences may also be used.

Additionally, it may be desirable to selectively express a polypeptide of the present invention in a specific target cell or tissue of a plant by synthesizing the encoding polynucoleotide sequence to contain codons optimized for high translational efficiency within the particular target cell or tissue. Such methods are known in the art and are specifically provided in PCT International Publication No. WO 00/42190 (which is hereby incorporated herein by reference).

Additional sequence modifications are known to enhance gene expression in a cellular host. These include elimination of sequences encoding spurious polyadenylation signals, exon-intron splice site signals, transposon like repeats, and other such well-characterized sequences that may be deleterious to gene expression. The G-C content of the sequence may be adjusted to levels average for a given cellular host, as calculated by reference to known genes expressed in the host cell. When possible, the sequence may be modified to avoid predicted hairpin secondary mRNA structures.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlbad, Calif.).

Preferred expression vectors in plant systems include, but are not limited to, Bin 19 (ATCC Deposit No: 37327), GA437 (ATCC Deposit No: 37350), pAK1003 (ATCC Deposit No: 37425), pAS2022 (ATCC Deposit No: 37426), pAS2023 (ATCC Deposit No: 37427), pAP2034 (ATCC Deposit No: 37428), pC22 (ATCC Deposit No: 37493), pHS24 (ATCC Deposit No: 37841), pHS85 (ATCC Deposit No: 37842), is pPM1 (ATCC Deposit No: 40172), pGV3111SE (ATCC Deposit No: 53213), pCGN978 (ATCC Deposit No: 67064), pFL61 (ATCC Deposit No: 77215), pGPTV-KAN (ATCC Deposit No: 77388), pGPTV-HPT (ATCC Deposit No: 77389), pGPTV-DHFR (ATCC Deposit No: 77390), pGPTV-BAR (ATCC Deposit No: 77391), pGPTV-BLEO (ATCC Deposit No: 77392), and/or pPE1000 (ATCC Deposit No: 87573). The skilled artisan would appreciate that any of the above vectors could easily be modified to either include or delete specific elements as may be required for operability. Other suitable vectors will be readily apparent to the skilled artisan.

Introduction of the construct into the host cell can be effected by biolistic transformation (Klein et al., Nature, 327:70–73 (1987)), PEG-mediated transfection (Paskowski, et al., EMBO J., 3:2717, (1984)), calcium phosphate transfection, DEAE-dextran mediated transfection, cationic lipid-mediated transfection, electroporation (Fromm, et al., PNAS, USA, 82:5824 (1985)), transduction, infection, *Agrobacterium tumefaciens*-directed infection, or other methods. Such methods are described in many standard laboratory manuals, such as Davis et al., Basic Methods in Molecular Biology (1986).

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells.

Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides, analogs, derivatives, and/or fragments of the invention can be chemically synthesized. (See, e.g., Merrifield, 1963, J. Amer. Chem. Soc. 85:2149–2156). For example, polypeptides can be synthesized by solid phase techniques, cleaved from the resin, and purified by preparative high performance liquid chromatography (e.g., see Creighton, 1983, Proteins, Structures and Molecular Principles, W. H. Freeman and Co., N.Y., pp. 50–60). The polypeptides can also be synthesized by use of a peptide synthesizer. The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49; Mass Spectroscopy peptide sequencing, etc). Furthermore, it desired, nonclassical amino acids or chemical amino acid analogs can be introduced as a substitution or addition into the polypeptide of the invention. Non-classical amino acids include but are not limited to the D-isomers of the common amino acids, 2,4-diaminobutyric acid, alpha.-amino isobutyric acid, 4-aminobutyric acid, Abu, 2-amino butyric acid, gamma.-Abu, .epsilon.-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, beta.-alanine, fluoro-amino acids, designer amino acids such as beta.-methyl amino acids, C.alpha.-methyl amino acids, N.alpha.-methyl amino acids, and amino acid analogs in general. Furthermore, the amino acid can be D (dextrorotary) or L (levorotary).

Manipulations of the polypeptide sequences of the invention may be made at the protein level. Included within the scope of the invention are polypeptides of the invention, fragments thereof, derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including, but not limited to, specific chemical cleavage by cyanogen bromide, trypsin, chymotrypsin, papain, V8 protease, NaBH4, acetylation, formulation, oxidation, reduction, metabolic synthesis in the presence of tunicamycin, etc.

Moreover, the invention encompasses additional post-translational modifications which include, for example, the addition of N-linked or O-linked carbohydrate moieties or chains, the addition of detectable labels which may be fluorescent, radioisotopic, enzymatic, in nature, the addition of epitope tagged peptide fragments (e.g., FLAG: SEQ ID NO:20, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methioine residue, etc.

Furthermore, the invention encompasses chemical derivitization of the polypeptides of the present invention, preferably where the chemical is a hydrophilic polymer residue. Exemplary hydrophilic polymers, including derivitives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. More preferred polymers have a molecular weight of about 150 to about 10,000, with molecular weights of 200 to about 8,000 being even more preferred.

Additional preferred polymers which may be used to derivitize polypeptides of the invention, include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivitize the polypeptides of the present invention can be a saccharide residue. Exemplary saccharides which can be derived include, for example, monosaccharides or sugar alcohols, such as erytlirose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides which may be used for derivitization include saccharides that can be attached to the polypeptides of the invention via alkylation or acylation reactions.

Moreover, the invention also encompasses derivitization of the polypeptides of the present invention, for example, with lipids (including cationic, anionic, polymerized, charged, synthetic, saturated, unsaturated, and any combination of the above, etc.). stabilizing agents.

The invention encompasses derivitization of the polypeptides of the present invention, for example, with compounds that may serve a stabilzing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutanine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as Pluronics.RTM., commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivitized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivitization, etc., in U.S. Pat. No. 6,028,066, which is hereby incorporated in its entirety herein.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:X. Primers can be selected using computer analysis so that primers do not span more than one predicted exon in the genomic DNA These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Disease mapping data are known in the art. Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected organisms can be examined. First, visible structural alterations in the chromosomes, such as deletions or translocations, are examined in chromosome spreads or by PCR. If no structural alterations exist, the presence of point mutations are ascertained. Mutations observed in some or all affected organisms, but not in normal organisms, indicates that the mutation may cause the disease. However, complete sequencing of the polypeptide and the corresponding gene from several normal organisms is required to distinguish the mutation from a polymorphism. If a new polymorphism is identified, this polymorphic polypeptide can be used for further linkage analysis.

Furthermore, increased or decreased expression of the gene in affected organisms as compared to unaffected organisms can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an organism and comparing the measured gene expression level with a standard level of polynucleotide expression level, whereby an increase or decrease in the gene expression level compared to the standard is indicative of a disorder.

By "measuring the expression level of a polynucleotide of the present invention" is intended qualitatively or quantitatively measuring or estimatng the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, phloem, xylym, secreted fluids, nectar, nodule fluid, appressorium fluid, canker fluid, gall fluid, fruit juice, trichome fluid, vacuole fluid, plastid fluid, cytosolic fluid, root exudates, interstitial fluid, etc.) which contain the polypeptide of the present invention, and other tissue sources found to express the polypeptide of the present invention (such as the following non-limiting examples root, stem, apical meristem, leaves, flowers, pedals, etc.). Methods for obtaining tissue biopsies and body fluids from plants are well known in the art. For example, methods for isolating interstitial fluid of plant cells and tissues can be found, for example, in International Publication No. WO 00/09725. Where the biological sample is to include mRNA, a tissue biopsy is the preferred source.

The method(s) provided above may preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject The knowledge of such polymorphisms (i.e. their location, as well as, their existence) would be beneficial in identifying disease loci for many disorders, including proliferative diseases and conditions. Such a method is described in U.S. Pat. Nos. 5,858,659 and 5,856,104. The US Patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point ($T_{sub.m}$) by 8°–20° C., vs. 4°–16° C. for the DNA/DNA 15-mer duplex. Also, the absence of charge groups in PNA means that hybridization can be done at low ionic strengths and reduce possible interference by salt during the analysis.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression, CRCPress, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

The present invention encompasses the addition of a nuclear localization signal, operably linked to the 5' end, 3' end, or any location therein, to any of the oligonucleotides, antisense oligonucleotides, triple helix oligonucleotides, ribozymes, PNA oligonucleotides, and/or polynucleotides, of the present invention. See, for example, G. Cutrona, et al., Nat. Biotech., 18:300–303, (2000); which is hereby incorporated herein by reference.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in a plant upon systemic injection, for example (Bartlett, R. J., et al., Nat Biotech, 18:615–622 (2000), which is hereby incorporated by reference herein in its entirety). Such RNA/DNA oligonucleotides could be designed to correct genetic defects in certain host strains, and/or to introduce desired traits in the plant host (e.g., introduction of a specific polymorphism within an endogenous gene corresponding to a polynucleotide of the present invention that may confer resistance to certain herbicides, pesticides, fungicides, etc.). Alternatively, the polynucleotide sequence of the present invention may be used to construct duplex oligonucleotides corresponding to said sequence, specifically designed to correct genetic defects in certain host strains, and/or to introduce desired traits in the plant host (e.g., introduction of a specific polymorphism within an endogenous gene corresponding to a polynucleotide of the present invention that may confer resistence to certain herbicides, pesticides, fungicides, etc.). Such methods of using duplex oligonucleotides are known in the art and are encompassed by the present invention (see EP1007712, which is hereby incorporated by reference herein in its entirety).

The polynucleotides are also useful for identifying organisms from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organisms genome. These sequences can be used to prepare PCR primers for amplifying and isolating such selected DNA, which can then be sequenced. Using this technique, organisms can be identified because each organism will have a unique set of DNA sequences. Once an unique ID database is established for an organism, positive identification of that organism, living or dead, can be made from extremely small tissue samples. Similarly, polynucleotides of the present invention can be used as polymorphic markers, in addition to, the identification of transformed or non-transformed plant cells and/or tissues.

There is also a need for reagents capable of identifying the source of a particular tissue. Such need arises, for example, when presented with tissue of unknown origin Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed plant cells and/or tissues.

Moreover, the polynucleotides of the present invention, the polynucleotides encoding the polypeptides of the present invention, the cDNA contained in the deposit, including variants and/or fragments therein, may be useful for modulating, inhibiting, increasing, decreasing, or introducing the following, non-limiting traits in a plant: drought tolerance, TV tolerance, flower development, terpene synthesis, abiotic stresse tolerance, heat stress tolerance, cold stress tolerance, nutritional stress tolerance, xenobiotic stress tolerance, protein storage capability, oil storage capability, amino acid content, amino acid composition, carbohydrate storage capability, oil content, oil composition, carbohydrate content, carbohydrate composition, fiber content, fiber composition, metabolite content, metaboliter composition, vitamin content, and/or vitamin composition. The polynucleotides of the invention, may also be useful in modulating plant yield, plant development, plant differentiation, root growth, root morphology, plant color, plant aroma, plant flavor, palatability of plant tissue, plant organoleptic properties, may be useful in phytoremediation, and/or plant defense. Moreover, the polypeptides of the invention may also be useful in modulating the plants ability to serve as a plant neutriceutical, pharmaceutical, or phytoceutical. Alternatively, polypeptides of the invention may also be useful in modulating the plants ability to produce plant neutriceuticals, pharmaceuticals, or phytoceuticals of either endogenous or exogenous origin (e.g., from another plant species, a human, a mammal, an animal, or other organism). In these contexts, the term "plant" may be applied to mean any plant cell, plant tissue, plant fluid, or plant feature, and includes plant infection structures, which may include, but are not limited to an appressorium, a gall, a canker, and/or nodules. In these contexts, the term "modulate" may be applied to mean the qualitative or quantitative increase, decrease, introduction of, inhibition of, complete loss of, or over-expression of a specific trait or characteristic as described above and elsewhere herein.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technecium (99 mTc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the organism. It will be understood in the art that the size of the subject and the imaging system used will determine the quantity of imaging moiety needed to produce diagnostic images. In the case of a radioisotope moiety, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982)). Such methods are equally applicable to plants.

Thus, the invention provides a diagnostic method of a disorder, which involves (a) assaying the expression of a polypeptide of the present invention in cells or body fluid of an organism; (b) comparing the level of gene expression with a standard gene expression level, whereby an increase or decrease in the assayed polypeptide gene expression level compared to the standard expression level is indicative of a disorder.

Moreover, polypeptides of the present invention can be used for the treatment, detection, and/or prevention of a disease, or disease state. For example, an organism can be administered a polypeptide of the present invention in an effort to replace absent or decreased levels of the polypeptide, to supplement absent or decreased levels of a different polypeptide, to inhibit the activity of a polypeptide, either directly or indirectly, to activate the activity of a polypeptide, either directly or indirectly, (e.g., by binding to a receptor), to reduce the activity of a membrane bound receptor by competing with it for free ligand, or to bring about a desired response (e.g., induction of differentiation, growth, senescence, germination, etc,).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Transgenic Methods

Another aspect of the present invention is to gene therapy methods for treating or preventing disorders, diseases and conditions. The gene therapy methods relate to the introduction of nucleic acid (DNA, RNA, and antisense DNA or RNA) sequences into an organism, preferably a plant, to achieve expression of a polypeptide of the present invention. This method requires a polynucleotide which codes for a polypeptide of the invention operatively linked to a promoter and any other genetic elements necessary for the expression of the polypeptide by the target tissue. Such transgenic and delivery techniques are known in the art, see, for example, WO90/11092, which is herein incorporated by reference.

Thus, for example, cells from a plant may be engineered with a polynucleotide (DNA or RNA) comprising a promoter operably linked to a polynucleotide of the invention ex vivo, with the engineered cells then being introduced back into the plant to "treat" the deficiency. Such methods are well-known in the art and are equally applicable to plants. For example, see Belldegrun et al., J. Natl. Cancer Inst., 85:207–216 (1993); Ferrantini et al., Cancer Research, 53:107–1112 (1993); Ferrantini et al., J. Immunology 153: 4604–4615 (1994); Kaido, T., et al., Int. J. Cancer 60: 221–229 (1995); Ogura et al., Cancer Research 50: 5102–5106 (1990); Santodonato, et al., Human Gene Therapy 7:1–10 (1996); Santodonato, et al., Gene Therapy 4:1246–1255 (1997); and Zhang, et al., Cancer Gene Therapy 3: 31–38 (1996)), which are herein incorporated by reference.

As discussed in more detail below, the polynucleotide constructs can be delivered by any method that delivers materials to the cells of an organism, such as, biolistic injection into the plant tissues (apical meristem, root, flower, stem, and the like). The polynucleotide constructs may be delivered in an acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art Such methods are described, for example, in U.S. Pat. Nos. 5,593,972, 5,589,466, and 5,580,859, which are herein incorporated by reference.

The polynucleotide vector constructs of the invention used in the gene therapy method are preferably constructs that will not integrate into the host genome nor will they contain sequences that allow for replication. Alternatively, the polynucleotide vector construcuts of the invention may integrate into the host genome and may replicate. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include the 35S, 34S, and actin promoters, in addition to any other promoter known in the art and/or described elsewhere herein. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The preferred route of administration is by the parenteral route of injection into the interstitial space of tissues. However, other parenteral routes may also be used In addition, naked DNA constructs can be delivered to a plants circulatory system by direct injection.

The naked polynucleotides are delivered by any method known in the art, including, but not limited to, direct needle injection at the delivery site, topical administration, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA, 84:7413–7416 (1987), which is herein incorporated by reference); mRNA (Malone et al., Proc. Natl. Acad. Sci. USA, 86:6077–6081 (1989), which is herein incorporated by reference); and purified transcription factors (Debs et al., J. Biol. Chem., 265:10189–10192 (1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl. Acad. Sci. USA, 84:7413–7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Felgner et al., Proc. Natl. Acad. Sci. USA, 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios.

Methods for making liposomes using these materials are well known in the art. For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512–527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include Ca2+-EDTA chelation (Papahadjopoulos et al., Biochim. Biophys. Acta, 394:483 (1975); Wilson et al., Cell, 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA, 76:145 (1979)); and reverse-phase evaporation (REV) (Fraley et al., J. Biol. Chem., 255:10431 (1980); Szoka et al., Proc. Natl. Acad. Sci. USA, 75:145 (1978); Schaefer-Ridder et al., Science, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1. U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals. Such methods are equally applicable to plants and is within the skill of the artisan.

In certain embodiments, cells are engineered, ex vivo or in vivo, using a retroviral particle containing RNA that comprises a sequence encoding polypeptides of the invention. Retroviral integration has been detected to occur in plants based upon the identification of a pararetrovirus sequences within the tabacco genome. Since such integration was determined to occur at very limited integration sites, such a pararetrovirus may represent a desirable genetic transformation vehicle for the polynucleotides of the present invention (Jakowitsch, J., et al., PNAS 96(23):13241–6 (1999).

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy, 1:5–14 (1990), which is incorporated herein by reference in its entirety. The vector may transduce the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line generates infectious retroviral vector particles that include polynucleotides encoding polypeptides of the invention. Such retroviral vector particles then may be employed, to transduce eukaryotic cells, either in vitro or in vivo. The transduced eukaryotic cells will express polypeptides of the invention.

The present invention also encompasses the application of retrotransposons to the genetic transformation of plants. The retrotransposons would preferably represent retrotransposons with known plant host range and would comprise polynucleotides encoding polypeptides of the present invention. Many retrotransposons are known in the art, some of which are described by Bennetzen J L, Trends Microbiol., 4(9):347–53 (1996) which is hereby incorporated herein by reference.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932–8935 (1989); and Zijlstra et al., Nature, 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transformation-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transformed. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, infusion, biolistic injectors, particle accelerators (i.e., "gene guns"), gelfoam sponge depots, other commercially available depot materials, osmotic pumps (e.g., Alza minipumps), and decanting or topical application. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)). Moreover, direct injection of naked DNA has been reported in plants and is encompassed by the present invention (Davey M R, et al., Plant Mol Biol, 13(3):273–85 (1989), and Potrykus I, Ciba Found Symp, 154:198–212 (1990)).

A preferred method of local administration is by direct injection. Preferably, a recombinant molecule of the present invention complexed with a delivery vehicle is administered by direct injection into or locally within the area of the organisms circulatory system (e.g., phloem, xylem, etc). Administration of a composition locally within the area of the organisms circulatory system refers to injecting the composition centimeters and preferably, millimeters within the organisms circulatory system.

Another method of local administration is to contact a polynucleotide construct of the present invention in or around a surgical wound or grafting. For example, the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include injection, aerosol, percutaneous (topical) delivery. Injections can be performed using methods standard in the art Aerosol delivery can also be performed using methods standard in the art (see, for example, Stribling et al., Proc. Natl. Acad. Sci. USA, 189:11277–11281 (1992), which is incorporated herein by reference). Topical delivery can be performed is by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the plant or animal, the precise condition requiring treatment and its severity, and the route of administration. The frequency of treatments depends upon a number of factors, such as the amount of polynucleotide constructs administered per application, as well as the half-life of the polynucleotide and polypeptides (i.e., the effective period of application). The precise amount, number of applications and timing of applications will be determined per desired application.

Therapeutic compositions of the present invention can be administered to any organism, preferably to plants. Preferred plants, may include the following non-limiting examples, including barley, oats, rye, sorghum, pea, sunflower, tobacco, cotton, petunia, tomato, broccoli, lettuce, apple, plum, orange, and lemon, and more preferrably rice, maize, conola, wheat, sugerbeet, sugercane, and soybean, in addition to other plants known in the art and referenced more particularly elsewhere herein (e.g., Table 3).

Moreover, the present invention encompasses transgenic cells, including, but not limited to seeds, organisms, and plants into which genes encoding polypeptides of the present invention have been introduced. Non-limiting examples of suitable recipient plants for introducing polynucleotides of the invention, polynucleotides encoding the polypeptides of the invention, the cDNA contained in a deposit, and/or fragments, and varients therein, are listed in Table 3 below:

TABLE 3

RECIPIENT PLANTS

| {PRIVATE}COMMON NAME | FAMILY | LATIN NAME |
|---|---|---|
| Maize | Gramineae | *Zea mays* |
| Maize, Dent | Gramineae | *Zea mays dentiformis* |
| Maize, Flint | Gramineae | *Zea mays vulgaris* |
| Maize, Pop | Gramineae | *Zea mays microsperma* |
| Maize, Soft | Gramineae | *Zea mays amylacea* |
| Maize, Sweet | Gramineae | *Zea mays amyleasaccharata* |
| Maize, Sweet | Gramineae | *Zea mays saccharate* |
| Maize, Waxy | Gramineae | *Zea mays ceratina* |
| Wheat, Dinkel | Pooideae | *Triticum spelta* |
| Wheat, Durum | Pooideae | *Triticum durum* |
| Wheat, English | Pooideae | *Triticum turgidum* |
| Wheat, Large Spelt | Pooideae | *Triticum spelta* |
| Wheat, Polish | Pooideae | *Triticum polonium* |
| Wheat, Poulard | Pooideae | *Triticum turgidum* |
| Wheat, Singlegrained | Pooideae | *Triticum monococcum* |
| Wheat, Small Spelt | Pooideae | *Triticum monococcum* |
| Wheat, Soft | Pooideae | *Triticum aestivum* |
| Rice | Gramineae | *Oryza sativa* |
| Rice, American Wild | Gramineae | *Zizania aquatica* |
| Rice, Australian | Gramineae | *Oryza australiensis* |
| Rice, Indian | Gramineae | *Zizania aquatica* |
| Rice, Red | Gramineae | *Oryza glaberrima* |
| Rice, Tuscarora | Gramineae | *Zizania aquatica* |
| Rice, West African | Gramineae | *Oryza glaberrima* |
| Barley | Pooideae | *Hordeum vulgare* |
| Barley, Abyssinian Intermediate, also Irregular | Pooideae | *Hordeum irregulare* |
| Barley, Ancestral Tworow | Pooideae | *Hordeum spontaneum* |
| Barley, Beardless | Pooideae | *Hordeum trifurcatum* |
| Barley, Egyptian | Pooideae | *Hordeum trifurcatum* |
| Barley, fourrowed | Pooideae | *Hordeum vulgare polystichon* |
| Barley, sixrowed | Pooideae | *Hordeum vulgare hexastichon* |
| Barley, Tworowed | Pooideae | *Hordeum distichon* |
| Cotton, Abroma | Dicotyledoneae | *Abroma augusta* |
| Cotton, American Upland | Malvaceae | *Gossypium hirsutum* |
| Cotton, Asiatic Tree, also Indian Tree | Malvaceae | *Gossypium arboreum* |
| Cotton, Brazilian, also, Kidney, and, Pernambuco | Malvaceae | *Gossypium barbadense brasiliense* |
| Cotton, Levant | Malvaceae | *Gossypium herbaceum* |
| Cotton, Long Silk, also Long Staple, Sea Island | Malvaceae | *Gossypium barbadense* |
| Cotton, Mexican, also Short Staple | Malvaceae | *Gossypium hirsutum* |
| Soybean, Soya | Leguminosae | *Glycine max* |
| Sugar beet | Chenopodiaceae | *Beta vulgaris altissima* |
| Sugar cane | Woody-plant | *Arenga pinnata* |
| Tomato | Solanaceae | *Lycopersicon esculentum* |
| Tomato, Cherry | Solanaceae | *Lycopersicon esculentum cerasiforme* |
| Tomato, Common | Solanaceae | *Lycopersicon esculentum commune* |

TABLE 3-continued

RECIPIENT PLANTS

| COMMON NAME | FAMILY | LATIN NAME |
|---|---|---|
| Tomato, Currant | Solanaceae | *Lycopersicon pimpinellifolium* |
| Tomato, Husk | Solanaceae | *Physalis ixocarpa* |
| Tomato, Hyenas | Solanaceae | *Solanum incanum* |
| Tomato, Pear | Solanaceae | *Lycopersicon esculentum pyriforme* |
| Tomato, Tree | Solanaceae | *Cyphomandra betacea* |
| Potato | Solanaceae | *Solanum tuberosum* |
| Potato, Spanish, Sweet potato | Convolvulaceae | *Ipomoea batatas* |
| Rye, Common | Pooideae | *Secale cereale* |
| Rye, Mountain | Pooideae | *Secale montanum* |
| Pepper, Bell | Solanaceae | *Capsicum annuum grossum* |
| Pepper, Bird, also Cayenne, Guinea | Solanaceae | *Capsicum annuum minimum* |
| Pepper, Bonnet | Solanaceae | *Capsicum sinense* |
| Pepper, Bullnose, also Sweet | Solanaceae | *Capsicum annuum grossum* |
| Pepper, Cherry | Solanaceae | *Capsicum annuum cerasiforme* |
| Pepper, Cluster, also Red Cluster | Solanaceae | *Capsicum annuum fasciculatum* |
| Pepper, Cone | Solanaceae | *Capsicum annuum conoides* |
| Pepper, Goat, also Spur | Solanaceae | *Capsicum frutescens* |
| Pepper, Long | Solanaceae | *Capsicum frutescens longum* |
| Pepper, Oranamental Red, also Wrinkled | Solanaceae | *Capsicum annuum abbreviatum* |
| Pepper, Tabasco Red | Solanaceae | *Capsicum annuum conoides* |
| Lettuce, Garden | Compositae | *Lactuca sativa* |
| Lettuce, Asparagus, also Celery | Compositae | *Lactuca sativa asparagina* |
| Lettuce, Blue | Compositae | *Lactuca perennis* |
| Lettuce, Blue, also Chicory | Compositae | *Lactuca pulchella* |
| Lettuce, Cabbage, also Head | Compositae | *Lactuca sativa capitata* |
| Lettuce, Cos, also Longleaf, Romaine | Compositae | *Lactuca sativa longifolia* |
| Lettuce, Crinkle, also Curled, Cutting, Leaf | Compositae | *Lactuca sativa crispa* |
| Celery | Umbelliferae | *Apium graveolens dulce* |
| Celery, Blanching, also Garden | Umbelliferae | *Apium graveolens dulce* |
| Celery, Root, also Turniprooted | Umbelliferae | *Apium graveolens rapaceum* |
| Eggplant, Garden | Solanaceae | *Solanum melongena* |
| Sorghum | Sorghum | All crop species |
| Alfalfa | Leguminosae | *Medicago sativum* |
| Carrot | Umbelliferae | *Daucus carota sativa* |
| Bean, Climbing | Leguminosae | *Phaseolus vulgaris vulgaris* |
| Bean, Sprouts | Leguminosae | *Phaseolus aureus* |
| Bean, Brazilian Broad | Leguminosae | *Canavalia ensiformis* |
| Bean, Broad | Leguminosae | *Vicia faba* |
| Bean, Common, also French, White, Kidney | Leguminosae | *Phaseolus vulgaris* |
| Bean, Egyptian | Leguminosae | *Dolichos lablab* |
| Bean, Long, also Yardlong | Leguminosae | *Vigna sesquipedalis* |
| Bean, Winged | Leguminosae | *Psophocarpus tetragonolobus* |
| Oat, also Common, Side, Tree | Avena | *Sativa* |
| Oat, Black, also Bristle, Lopsided | Avena | *Strigosa* |
| Oat, Bristle | Avena | |
| Pea, also Garden, Green, Shelling | Leguminosae | *Pisum, sativum sativum* |
| Pea, Blackeyed | Leguminosae | *Vigna sinensis* |
| Pea, Edible Podded | Leguminosae | *Pisum sativum axiphium* |
| Pea, Grey | Leguminosae | *Pisum sativum speciosum* |
| Pea, Winged | Leguminosae | *Tetragonolobus purpureus* |
| Pea, Wrinkled | Leguminosae | *Pisum sativum medullare* |
| Sunflower | Compositae | *Helianthus annuus* |
| Squash, Autumn, Winter | Dicotyledoneae | *Cucurbita maxima* |
| Squash, Bush, also Summer | Dicotyledoneae | *Cucurbita pepo melopepo* |

TABLE 3-continued

RECIPIENT PLANTS

| COMMON NAME | FAMILY | LATIN NAME |
|---|---|---|
| Squash, Turban | Dicotyledoneae | *Cucurbita maxima turbaniformis* |
| Cucumber | Dicotyledoneae | *Cucumis sativus* |
| Cucumber, African, also Bitter | | *Momordica charantia* |
| Cucumber, Squirting, also Wild | | *Ecballium elaterium* |
| Cucumber, Wild | | *Cucumis anguria* |
| Poplar, California | Woody-Plant | *Populus trichocarpa* |
| Poplar, European Black | | *Populus nigra* |
| Poplar, Gray | | *Populus canescens* |
| Poplar, Lombardy | | *Populus italica* |
| Poplar, Silverleaf also White | | *Populus alba* |
| Poplar, Western Balsam | | *Populus trichocarpa* |
| Tobacco | Solanaceae | *Nicotiana* |
| *Arabidopsis Thaliana* | Cruciferae | *Arabidopsis thaliana* |
| Turfgrass | Lolium | |
| Turfgrass | Agrostis | |
| | Other families of turfgrass | |
| Clover | Leguminosae | |

Biological Activities

The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Hyperproliferative Disorders

Polynucleotides or polypeptides, or agonists or antagonists of the invention can be used to detect, prevent, and/or confer resistence to hyperproliferative diseases, disorders, and/or conditions, which include, but are not limited to, cankers, galls, tumors, appressorium, etc. Polynucleotides or polypeptides, or agonists or antagonists of the present invention may inhibit the proliferation of the disorder through direct or indirect interactions. Alternatively, polynucleotides or polypeptides, or agonists or antagonists of the present invention may proliferate other cells which can inhibit the hyperproliferative disorder.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in organisms comprising administration of one or more active gene copies of the present invention to an abnormally proliferating cell or cells. In a preferred embodiment, a polynucleotide of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus vector, or more preferrably a plant retrotransposon-based vector. In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such, a beneficial therapeutic affect of the present invention may be expressly modulated (i.e. to increase, decrease, or inhibit expression of the present invention) based upon said external stimulus.

Polynucleotides of the present invention may be useful in repressing expression of proliferating genes or antigens. By "repressing expression of the proliferating genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transformation, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transform cells which are abnormally proliferating and spare non-dividing cells, it is preferable to utilize a retrovirus, or a plant retrotransposon-based vector (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in the plants body by use of imaging devices used to guide an injecting needle directly to the disease site. The polynucleotides of the present invention may also be administered to disease sites at the time of grafting, etc.

By "cell proliferative disease" is meant any disease or disorder, affecting any one or any combination of organs, cavities, or body parts, which is characterized by single or multiple local abnormal proliferations of cells, groups of cells, or tissues.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target or abnormally proliferating cell growth in tissue culture, tumor growth in plants and cell cultures, or any other method known to one of ordinary skill in the art.

The present invention is further directed to antibody-based therapies which involve administering anti-polypeptides and anti-polynucleotide antibodies to a plant, for detecting, preventing, and/or conferring resistance to one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for detecting, preventing, and/or conferring resistance to a plant having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with cytokinins or plant growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragements thereof, of the present invention. Such antibodies, fragments, or regions, will preferably have an affinity for polynucleotides or polypeptides, including fragements thereof. Preferred binding affinities include those with a dissociation constant or Kd less than $5 \times 10\text{-}6M$, $10\text{-}6M$, $5 \times 10\text{-}7M$, $10\text{-}7M$, $5 \times 10\text{-}8M$, $10\text{-}8M$, $5 \times 10\text{-}9M$, $10\text{-}9M$, $5 \times 10\text{-}10M$, $10\text{-}10M$, $5 \times 10\text{-}11M$, $10\text{-}11M$, $5 \times 10\text{-}12M$, $10\text{-}12M$, $5 \times 10\text{-}13M$, $10\text{-}13M$, $5 \times 10\text{-}14M$, $10\text{-}14M$, $5 \times 10\text{-}15M$, and $10\text{-}15M$.

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues. Apoptosis has been described in plants and is thought to be regulated via mechanisms analogous to apoptosis induction in animals (see, for example, LoSchiavo F, et al., Eur J. Cell Biol., 79(4):294–8 (2000); and Tian R, et al., FEBS Lett., 474(1):11–15 (2000)).

Moreover, in another preferred embodiment of the present invention, said polypeptides may induce apoptosis through other mechanisms, such as in the activation of other proteins which will activate apoptosis (e.g., caspase 3, poly(ADP-ribose) polymerase (PARP), etc), or through stimulating the expression of said proteins, either alone or in combination with small molecule drugs or adjuvants, such as apoptonin, galectins, thioredoxins, antiinflammatory proteins (See for example, Mutat Res 400(1–2):447–55 (1998), Med Hypotheses.50(5):423–33 (1998), Chem Biol Interact. April 24;111–112:23–34 (1998), J Mol Med.76(6):402–12 (1998), Int J Tissue React;20(1):3–15 (1998), which are all hereby incorporated by reference).

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, or indirectly, to said antigens and immunogens.

Infectious Diseases

Infectious agents may inhibit the plants overall ability to maintain plan homeostasis and/or cellular homeostasis. For example, the infectious agent may inhibit the plants ability to control cellular division, differentiation, and development; absorption of water and minerals from the soil and the translocation of these substances throughout the plant; photosynthesis and translocation of the photosynthetic products to areas of use or storage; metabolism of systhesized compounds; reproduction; and storage of plant food-stuffs for overwintering or reproduction, for example.

Affected cells and tissues of diseased plants are usually weakened or destroyed by disease-causing agents. The ability of such infected cells and tissues to perform normal physiological functions is thus reduced or completely inhibited, causing cell or plant death. The type of tissue affected determines the physiological function affected. For example, infection of the root (e.g., root rot), interferes with absorption of water and nutrients from the soil; infection of the xylem vessels (e.g., vascular wilts, cankers, etc.) interferes with translocation of water and minerals to the crown of the plant; infection of the foliage (e.g., leaf spots, blights, mosaics, etc.) interferes with photosynthesis; infection of the cortex (e.g., cortical canker, viral and mycoplasmal infections of phloem, etc.) interferes with the downward translocation of photosynthetic products; flower infections (e.g., bacterial and fungal blights, viral, mycoplasmal, and fungal infections of flowers, etc.) interfere with reproduction; and infections of fruit (e.g., fruit rot, etc.) interefer with reproduction or storage of reserve food stuffs for the new plant. The above list of infectious traits and/or symptoms is exemplary and should not be construed as limiting the present invention. Additional infectious traits are known in the art, some of which are described elsewhere herein (see for example, Agrios, G. N., in "Plant Pathology", $3^{rd}$ Ed., Academic Press, Inc., (1988); which is hereby incorporated in its entirety herein).

Viruses are one example of an infectious agent that can cause disease or traits that can be detected, prevented, and/or resistence conferred to by a polynucleotide or polypeptide and/or agonist or antagonist of the present invention. Examples of viruses, include, but are not limited to to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Additional examples of viruses, include, but are not limited to to the following Tobamovirus group (e.g., Tobacco Mosaic), Tobravirus group (e.g., Tobacco rattle virus), Hordeivirus group (e.g., Barlet strip mosaic), Potexvirus group (e.g., Potato virus X), Carlavirus group (e.g., Carnation latent virus), Potyvirus group (e.g., potato virus Y), Closterovirus group (e.g., beet yellows virus), Maize chlorotic dwarf virus, Tobacco necrosis virus, Tymovirus group (e.g., Turnip yellow mosiac virus), Tombusvirus group (e.g., Tomato bushy stunt virus), Sobemovirus group (e.g., Southern bean mosaic virus), Luteovirus group (e.g., Barley yellow dwarf virus), Comovirus group (e.g., Cowpea mosaic virus), Nepovirus group (e.g., Tobacco ringspot virus), Pea enation mosaic virus, Dianthovirus group (e.g., Carnation ringspot virus), Cucumovirus group (e.g., Cucumber mosaic virus), Bromovirus group (e.g., Brome mosaic virus), Ilavirus group (e.g., Tobacco streak virus), Alfalfa mosaic virus, Tomatto spotter wilt virus, Rhabdoviridae (e.g., Lettuce necrotic yellows virus), Rioviridae (e.g., Wound tumor virus), Geminivirus group (e.g., Maize streak virus), and Caulimovirus (e.g., Cauliflower mosaic virus). Additional viruses capable of infecting a plant or animal are known in the art (see, for example, G. N., Agrios, supra, and Jones, T. C., in "Veterinary Pathology", $4^{th}$ Edition, Lea and Febiger, Philadelphia, (1972).

Viruses falling within these families can cause a variety of diseases or symptoms, generally including, but not limited to: mosaics, ring spots, stunting, dwarfing, leaf roll, yellowing, streaking, pox, enation, tumors, pitting of stem, aspermy, sterility, pitting of fruit, flattening and distortion of the stem; and specifically include, but not limited to tobacco mosaic, bean mosaic, apple mosaic, pear ring pattern mosaic, maize dwarf mosaic, tulip breaking, tobacco ringspot, prunus necrtic ringspot, elm ringspot, chysanthemum ringspot, lilac ringspot, blueberry ringspot, beet yellows, wheat streak mosaic, tobacco etch, vein enation, vein clearing, vein banding, vein necrosis, potato leaf roll, grape fan leaf, tomato shoestring, stunting, banana bunchy top, citrus tristeza, cocao swollen shoot, stem pitting, apple flat limb, pear rough bark, stem necrosis, graft brown line, cherry black canker, elm zonate canker, citrus woody gall, clover wound tumor, apple russet ring, apple scar skin, pear stony pit, spotted wilt, etc. Viruses may also lead to decreased photosynthesis, decreased chorophyll per leaf, decreased photosynthesis, decreased chorophyll per leaf, decreased chlorophyll efficiency, decrease in plant hormone production, decreased growth rate, decreased soluble nitrogen, decreased carbohydrate levels, either an increase or decrease in respiration, aberant plant metabolism, decrease water translocation, decreased nutrient retention, increased transpiration, reduced yields, modulate transcription of the plant, modulate translation of the plant, and aberrant cellular metababoliss. Additional symptoms caused by viral infections are known in the art (see, for example, G. N., Agrios, supra; Jones, T. C., in "Veterinary Pathology", $4^{th}$ Edition, Lea and Febiger, Philadelphia, (1972); and in "Viral and Rickettsial Infections of Animals", eds, Betts, A. O., and York, C. J., Academic Press, NY, (1967)). Polynucleotides or polypeptides, or agonists or antagonists of the invention, can be used to either directly or indirectly, detect, prevent, and/or confer resistance to any of these traits or diseases. For example, a polynucleotide or polypeptide of the present invention may directly inhibit a disorder or infection when transgenically overexpressed in a plant Alternatively, for example, a polynucleotide or polypeptide of the present invention may indirectly inhibit a disorder or infection by inhibiting the ability of the virus to transmit the infection from one plant to another.

As inferred to above, plant viral infections may be transmitted through a number of mechanisms, which include, but are not limited to the following: transmission through vegetative propagation, mechanical transmission through sap, seed transmission, pollen transmission, insect transmission, mite transmission, nematode transmission, fungal transmission, and dodder transmission. Polynucleotides or polypeptides, or agonists or antagonists of the invention, can be used to either directly or indirectly, detect, prevent, inhibit, and/or confer resistance to any of these mechanisms of viral transmission.

Similarly, bacterial agents that can cause disease or symptoms in plants or animals can be detected, prevented, and/or resistance conferred to the plant by a polynucleotide or polypeptide and/or agonist or antagonist of the present invention. Examples of such bacterial agents include, but not limited to, the following: Gram-Negative and Gram-positive bacteria and bacterial families and fungi: Bacillaceae (e.g., Anthrax, Clostridium), Bacteroidaceae, *Blastomycosis, Bordetella, Borrelia* (e.g., *Borrelia burgdorferi*), *Brucellosis, Candidiasis, Campylobacter, Coccidioidomycosis, Crypto-*

*coccosis, Dermatocycoses, E. coli* (e.g., Enterotoxigenic *E. coli* and Enterohemorrhagic *E. coli*), Enterobacteriaceae (*Klebsiella, Salmonella* (e.g., *Salmonella typhi,* and *Salmonella paratyphi*), *Serratia, Yersinia*), *Erysipelothrix, Helicobacter, Legionellosis, Leptospirosis, Listeria, Mycoplasmatales, Mycobacterium leprae, Vibrio cholerae,* Neisseriaceae (e.g., *Acinetobacter, Gonorrhea, Menigococcal*), *Meisseria meningitidis,* Pasteurellacea Infections (e.g., *Actinobacillus, Heamophilus* (e.g., *Heamophilus influenza* type B), *Pasteurella*), *Pseudomonas,* Rickettsiaceae, Chlamydiaceae, *Syphilis, Shigella* spp., Staphylococcal, Meningiococcal, Pneumococcal and Streptococcal (e.g., *Streptococcus pneumoniae* and Group B *Streptococcus*). Additional examples of bacterial agents include, for example, *Agrobacterium, Clavibacter, Erwinia, Pseodomonas, Xanthomonas, Streptomyces, Xylella, Mycoplasm, Acholeplasma,* and *Spiroplasmas.* Additional bacterial agents capable of infecting a plant or animal are known in the art (see, for example, G. N., Agrios, supra, and Jones, T. C., in "Veterinary Pathology", 4$^{th}$ Edition, Lea and Febiger, Philadelphia, (1972)

Bacterial agents falling within any of the aforementioned families can cause a variety of diseases or symptoms, generally including, but not limited to: leaf spots, leaf blights, soft rots (e.g., of fruit, root, and storage organs, etc.), wilts, overgrowths, scabs, cankers, nodules, galls, yellowing, phloem necrosis, X-disease, fasciation, and hairy root; and specifically, for example, crown gall, twig gall, cane gall, potato ring rot, tomato canker and wilt, banana wilt bud blast, cutting rot, black venation, bulb rot, citrus canker, walnut blight, pototo scab, sweet potato soil rot, tobacco wildfire, bean blight, cucumber angular leaf spot, cotton angular leaf spot, cereal blight, grass blight, tomato bacterial spot, pepper bacterial spot, stone fruit bacterial spot, bacterial vascular wilts, cucurbit bacterial wilt, pear fire blight, apple fire blight, pototo ring rot, southern bacterial wilt of solanaceous plants, Moko disease of banana, gummosis of stone fruit trees, Pierce's Disease of grape, almpond leaf scorch, alfalfa dwarf, phony peach, plum leaf scald, ratoon stunting, clover club leaf, aster yellows, big bud, apple proliferation, peach yellows, apple rubbery wood, pear decline, elm phloem necrosis, coconut lethal yellowing, citrus tubborn, decreased photosynthesis, decreased chorophyll per leaf, decreased chlorophyll efficiency, decrease in plant hormone production, decreased growth rate, decreased soluble nitrogen, decreased carbohydrate levels, either an increase or decrease in respiration, aberant plant metabolism, decrease water translocation, decreased nutrient retention, increased transpiration, reduced yields, modulate transcription of the plant, modulate translation of the plant, aberrant cellular metababolism, and corn stunt Additional symptoms and diseases caused by bacterial agents are known in the art (see, for example, G. N., Agrios, supra, and Jones, T. C., in "Veterinary Pathology", 4$^{th}$ Edition, Lea and Febiger, Philadelphia, (1972). Polynucleotides or polypeptides, agonists or antagonists of the invention, can be used, either directly or indirectly, to detect, prevent, and/or confer resistance to any of these symptoms or diseases.

Similarly, fungal agents that can cause disease or symptoms in plants or animals can be detected, prevented, and/or resistance conferred to the plant by a polynucleotide or polypeptide and/or agonist or antagonist of the present invention. Examples of such fungal agents include, but not limited to, the following: Actinomycetales (e.g., *Corynebacterium, Mycobacterium, Norcardia*), *Cryptococcus neoformans,* Aspergillosis, Myxomycota (e.g., Myxomycetes (*Fuligo, Muciliago, Physarum, Physarales,* etc), and Plasmodiophoromycetes (*Plasmodiophora* (e.g., *P. brassicae*), *Polymyxa* (e.g., *P. graminis*, etc.), *Spongospora* (e.g., *S. subteranea,* etc.))), Eumycota (e.g., Mastigomycotina, Chrytridiomycetes (e.g., *Olpidium brassicae, Physoderma maydia, Synchytrium endobioticum, Urophlyctis alfalfae,* etc.), Oomycetes, Saprolegniales (e.g., *Aphanomyces*, etc.), Peronosporales, Pythiaceae, *Pythium* (e.g., *Phytophthora infestans,* etc.), Albuginaceae (e.g., *Albugo candida,* etc.), Peronosporaceae (e.g., *Plasmopara viticola, Peronospora nicotianae, Bremia lactucae, Sclerospora grainicola,* and *Pseudoperonospora cubensis,* etc.), Zygomycotina, Zygomycetes, Mucorales, *Rhizopus* (e.g., *Choanephora cucurbitaum,* etc.), Endogonales, Endogone, Ascomycotina, Heriascomycetes, Endomycetales (e.g., *Saccharomyces cerevisiae,* etc.), Taphrina, Pytenomycetes, Erysiphales (e.g., *Erysiphe, Microsphaera, Podosphaera leucotricha, Spaerotheca pannosa, Uncinula necator* etc.), Sphaeriales (e.g., *Botryosphaeria obtusa, Ceratocystis, Diaporthe, Endothia parasitica, Eutyps armeniacae, Glomerella cingulata, Gnomonia, Hypoxylon mammatum, Rosellinia, Valsa, Xylaria,* etc.), Hypocreales (e.g., *Claviceps purpurea, Gibberella, Nectria,* etc.), Loculoascomycetes, Myriangiales (e.g., *Elsinoe,* etc.), Dothideales (e.g., *Capnodium, Didymella, Guignardia bidwellii, Microcyclus elei, Plowrightia morbosum,* etc.) Pleosporales (e.g., *Cochliobolus sativus, Gaeumannomyces graminis, Pyrenophora, Venturia inaequalis,* etc.), Discomycetes, Phacidiales (e.g., *Rhytisma acerinum*), Helotiales (e.g., *Diplocarpos rosae, Higginsia hiemalis,* Lophodermium, *Monilinia fructicola, Pseudopeziza trifolii, Sclerotinia sclerotiorum,* etc.), Deuteromycotina, Coelomycetes, Sphaeropsidales (e.g., *Ascochyta pisi, Coniothyrium, Cytospora, Diplodia maydis, Phoma lingam, Phomopsis, Phyllosticta, Septoria apii,* etc.), Melanconiales (e.g., *Celletotrichum, Coryneium beijerincki, Cylindrosporium, Gloeosporium, Marssonina, Melanconium fuligenum, Sphaceloma,* etc.), Hyphomycetes, Hyphales (e.g., *Alternaria, Asperigillus, Bipolaris, dreschslerea, Excerophilum, Botrytis cinerea, Cercospora, Fulvia fulva, Fusarium, Geotrichum candidum, Graphium ulmi, Peniciuum, Phymatotrichum omnivorum, Pyricularia, Spilocaea, Theilaviopsis basicola, Trichoderma, Verticillum,* etc.), Agonomycetes, Agonomycetales (e.g., *Rhizoctonia, Sclerotium,* etc.), Basidomycotina, Hemibasidiomycetes, Ustilaginales (e.g., *Sphaceltheca, Tilletia, Urocystis cepulae, Ustilago,* etc.), Uredinales (e.g., *Cronartium, Gymnosporangium juniperivirginianae, Melampsora lini, Phragmidium, Puccinia, Uromyces appendiculatus,* etc.), Hymenomycetes, Exobasidiales (e.g., *Exobasidium,* etc.), Aphyllochorales (e.g., *Aethalia, Corticium, Heterobasidum, Lenzites, Peniophora, Polyporus, Poria, Schizophyllum, Stereum,* etc.), Tulasnellales (e.g., *Thanatephorus, Typhula,* etc.), Agaricales (e.g., *Armillaria mellea, Marasmius, Pholiota, Pleurotus,* etc.), and particularly *Ascomycota, Basidiomycota, Zygomycota, Oomycota, Plasmodiophoromycota, Puccinia recondita, Rhizo puschinensis, Plasmo paraviticola, Plasmodiophora brassicae, Erwinia amylovora, Elsinoe fawcettii, Phaeosphaeria nodorum, Mycosphaerella arachidis, Mycosphaerella berkeleyi, Mycosphaerella fijiensis, Mycosphaerella graminicola, Pyrenophora teres, Pyremophora tritici-repentis, Venturia carpophila, Alternaria brassicae, Alternaria kikuchiana, Alternaria mali, Alternaria solani, Cercospora beticola, Cladosporium cucumerinum, Septoria lycopersici, Blumaria graminis, Erysiphe cichoracearum, Podosphaera leucotricha, Sphaerotheca fliginea, Uncinila necator, Emericella nidulans, Penicillium digitatum, Penicillium italicum, Gibberella fujikuroi, Nectria haematococca, Fusarium culmorum, Fusarium oxysporum,*

*Fusarium roseum, Gliocladium virens, Botryotinia fuckeliana, Monilinia fructigena, Sclerotinia homoeocarpa, Sclerotinia sclerotiorum, Mollisia yallundae, Glomerella lagenaria, Saccaromyces cerevisiae, Neurospora crassa, Gaemannomyces graminis, Magneporthe grisea, Monographella nivalis, Rhyncosporium secalis, Athelia rolisii, Typhula incarnata, Thanatephoms cucumeris, Rhizoctonia solani, Hemileia vastatix, Puccinia hordei,* and *Uromyces appendiculatas.* Additional fungal agents are known in the art (see, for example, G. N., Agrios, supra, G. C. Ainsworth, in "Fungal Diseases of Animals", Commonwealth Agricultural Bureaux, Farmham Royal Bucks, England, (1959), and Jones, T. C., in "Veterinary Pathology", 4th Edition, Lea and Febiger, Philadelphia, (1972)).

Fungal agents falling within any of the aforementioned divisions, subdivisions, classes, orders, genus's, or species can cause a variety of diseases or symptoms, generally including, but not limited to: necrosis, plant death, cell death, hypotrophy, hypoplasmia, stunting, hyperplasia (e.g., clubroot, galls, warts, witches brooms, leaf curls, etc.), tumors, leaf spots, blight, cankers, dieback, root rot, damping off, basal stem rot, soft rots, dry rots, anthracnose, scab, decline, wilt, rust, mildew, and smut; and specifically, fructifications, powdery scab of potato, clubroot of crucifers, black wort of potato, crown wart of alfalfa, brown spot of corn, seed rot, seedling damping off, root and stem rot, blight, tuber rot, white rust, upper side, downy mildews, oospores on soybean seed, rhizopus soft rots, rhizopus fruit rot, choanephora squash rot, bread mold, bud rot, stem rot, collar rot, crown rot, trunk rot, black pod disease, late blight of potatoes, Anthraenose diseases, Colletotrichum diseases, onion smudge, ergot, Botrytis diseases, vascular wilts, Dutch Elm disease, Gibberella diseases, Sclerotinia Diseases, Rhizoctonia Diseases, Sclerotium Diseases, postharvest decay of fruits and vegetables, decreased photosynthesis, decreased chorophyll per leaf, decreased chlorophyll efficiency, decrease in plant hormone production, decreased growth rate, decreased soluble nitrogen, decreased carbohydrate levels, either an increase or decrease in respiration, aberant plant metabolism, decrease water translocation, decreased nutrient retention, increased transpiration, reduced yields, modulate transcription of the plant, modulate translation of the plant, and aberrant cellular metababolism; and particularly citrus scab, grape black rot, wheat septoria nodorum blotch, early leaf spot of peanut, banana black sigatoka, wheat septoria tritici blotch, barley net blotch, cereal tan spot, apple scab, peach feckle, cabbage blackspot, apple leaf blotch, tomato and potato early blight, cercospora leaf spot of beet, cucumber scab, tomato seporial leaf spot, wheat powdery mildew, barlet powdery mildew, cucumber powdery mildew, apple powdery mildew, cucumber powdery mildew, grape powdery mildew, saporphyte, green mold of citrus, blue mold of citrus, rice bakanae disease, cereal headscab, cucumber fusarium wilt, tomato fusarium wilt, radish yellow fusarium, rice damping, pepper botrytis blight, botrytis blights of bean, botrytis blights of cuke, botrytis blights of grape, botrytis blights of marigold, brown rot of stone fruits, turf dollar spot, wheat eye spot, cucumber anthracnose, pestalotial leaf spot, rice blast, turf snow mold, barley scald, typhula blight, rhizoctonia damping, coffee rust, wheat lead rust, barley leaf rust, and bean rust Polynucleotides or polypeptides, agonists or antagonists of the invention, can be used, either directly or indirectly, to detect, prevent, and/or confer resistance to any of these symptoms or diseases. Additional fungal agents capable of infecting a plant or animal are known in the art (see, for example, G. N., Agrios, supra, G. C. Ainsworth, in "Fungal Diseases of Animals", Commonwealth Agricultural Bureaux, Farmham Royal Bucks, England, (1959), and Jones, T. C., in "Veterinary Pathology", 4th Edition, Lea and Febiger, Philadelphia, (1972)).

Moreover, parasitic agents causing disease or symptoms that can be detected, prevented, and/or conferred resistance to by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae,* and *Plasmodium ovale*). Additional examples of parasitic agents include, for example, Cuscutaceae (e.g., Cuscuta, dodder, etc.), Viscaceae (e.g., *Arceuthobium* (dwarf mistletoe of conifers), Phoradendron (American true mistletoes of broadleaved trees), and Viscum (European true mistletoes)), Orobanchaceae (e.g., Orobanche (broomrapes of tabocco)), and Scrophulariaceae (e.g., Striga (witchweeds of monocot plants)). These parasites can cause a variety of diseases or symptoms, including, but not limited to: decreased water storage, decreased mineral availability, decreased carbohydrate storage, decreased plant defense, and increased susceptability to fungal, bacterial, or viral infections. Additional parasitic diseases are known in the art (see, for example, G. N., Agrios, supra, and Jones, T. C., in "Veternay Pathology", 4th Edition, Lea and Febiger, Philadelphia, (1972). Polynucleotides or polypeptides, or agonists or antagonists of the invention, can be used to detect, prevent, and/or confer resistence to any of these symptoms or diseases.

Methods of treatment or prevention using a polypeptide or polynucleotide and/or agonist or antagonist of the present invention are well known in the art, though may include administering an effective amount of a polypeptide to the plant, seed, tissue, or cells. Alternatively, treatment or prevention could be conferred by transforming the plant, seed, tissue, or cells with a polynucleotide of the present invention, or cells could be removed from the plant, transformed, and then returning the engineered cells to the plant (ex vivo therapy). Moreover, the polypeptide or polynucleotide of the present invention can be used as an antigen to create antibodies that inhibit the pathogenicity of a particular infectious disease (e.g., inhibiting the expression of a plant-specific gene or protein critical for the pathogenicity of an infectious organism). In addition, any method of detecting, preventing, conferring resistence to, or inhibiting an infectious agent using a polypeptide or polynucleotide and/or agonist or antagonist of the present invention may be applied to detecting, preventing, conferring resistance to, or inhibiting an infectious agent in a human, animal, mammal, or other organism, with or without additional modification.

Pest Tolerance

Nematodes are one example of pests capable of causing disease or traits that can be detected, prevented, and/or resistance conferred to by a polynucleotide or polypeptide and/or agonist or antagonist of the present invention. Examples of nematodes include, but are not limited to, the following: Tylenchida, Tylenchina, Tylenchoidia, Tylenchidea, Tylenchidae, Anguina, Ditylenchus, Tylenchorhynchidae, Tylenchorhynchus, Pratylenchidae, Pratylenchus, Radopholus, Hoplolaimidae, Hoplolaimus, Rotylenchus, Helicotylenchus, Belonolaimidae, Belonolaimus, Heteroderoidea, Heterderidae, Globodera, Heterodera, Meloidogyne, Nacobbidae, Nacobbus, Rotylenchulus, Criconematoidea, Criconematidae, Criconemella, Hemicycliophora, Paratylenchidae, Paratylenchus, Tylenchuidae, Tylenchulus, Aphelenchina, Aphelenchoidea, Aphelenchoididae, Aphlenenchoides, Bursaphelenchus, Rhadinaphelenchus, Dorylaimida, Longidoridae, Longidorus, Xiphinema, Trichodoridae, Paratrichodorus, And Trichodorus. Other members of the nematode phylum, orders, suborders, superfamilies, families, genuses, and species are known in the art.

Nematodes falling within any of the aforementioned, orders, suborders, superfamilies, families, genuses, and/or species can cause a variety of diseases or symptoms in plants, generally including, but not limited to: root knots, root galls, reduced plant growth, plant nutrient deficiencies, yellowing, wilting, reduced yields, poor product quality, plant galls, necrotic lesions, rots, twisting or distortion of leaves and stems, abnormal floral development; hypertrophy, hypotrophy, cysts, and chlorosis. Polynucleotides or polypeptides, agonists or antagonists of the invention, can be used, either directly or indirectly, to detect, prevent, and/or confer resistance to any of these symptoms or diseases. Additional diseases and/or disorders caused by nematodes are known in the art.

Insects are another example of pests capable of causing disease or traits that can be detected, prevented, and/or resistance conferred to by a polynucleotide or polypeptide and/or agonist or antagonist of the present invention. Examples of insects include, but are not limited to, the following: insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera.

Polynucleotides or polypeptides, agonists or antagonists of the invention, can be used, either directly or indirectly, to detect, prevent, and/or confer resistance to any of the following, non-limiting, symptoms or diseases caused by insect pests of major crops: Maize: *Ostrinia nubilalis*, European corn borer, *Agrotis ipsilon*, black cutworm; *Helicoverpa zea*, corn earworm; *Spodoptera ftugiperda*, fall armyworm; *Diatraea grandiosella*, southwestern corn borer; *Elasmopalpus lignosellus*, lesser cornstalk borer; *Diatraea saccharalis*, surgarcane borer, *Diabrotica virgifera*, western corn rootworm; *Diabrotica barberi*, northern corn rootworm, *Diabrotica undecimpunctata howardi*, spotted cucumber beetle, *Melanotus* spp., wireworms; *Cyclocephala borealis*, northern masked chafer (white grub); *Cyclocephala immaculata*, southern masked chafer (white grub); *Popilliajaponica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus*, chinch bug; *Melanoplus femurrubrum*, redlegged grasshopper; *Melanoplus sanguinipes*, migratory grasshopper, *Delia platura*, seedcorn maggot; *Agromyza parvicomis*, corn blotch leafminer; *Anaphothrips obscrurus*, grass thrips; *Solenopsis milesta*, thief ant; *Tetranychus urticae*, twospotted spider mite; *Busseola Jusca*, African Maize Stem Borer (AMB); *Sesamia calamistis*, African Pink Borer (AP13); *Eldana sacchharina*, African Sugarcane Borer (ASB); *Chilo partellus*, Sorghum Stem Borer (SSB); *Osuna fuaacalis*, Oriental Corn Borer (OCB); *Sesamia nonagrioides*, Corn borer in Europe/N. Africa; Syrahum: *Clilo partellus*, sorghum borer, *Spodoptera ftugiperda*, fall armyworm; *Relicoverpa zea*, corn earworm; *Elasmopalpus lignosellus*, lesser cornstalk borer; *Agrotis subterranea*, granulate cutworm; *Phyllophaga crinita*, white grub; *Eleodes, Conoderus,* and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Siphaflava*, yellow sugarcane aphid; *Blissus leucopterus*, chinch bug; *Contarinia sorghicola*, sorghum midge; *Tetranychus cinnabarinus*, carmine spider mite; *Tetranychus urticae*, twospotted spider mite; *Schizaphis graminum*, Greenbug (aphid); Wheat: *Pseudaletia unipunctata*, army worm; *Spodoptera ftugiperda*, fall armyworm; *Elasmopalpus lignosellus*, lesser cornstalk borer; *Agrotis orthogonia*, plae western cutworm; *Oulema melanopus*, cereal leaf beetle; *Hypera punctata*, clover leaf weevil; *Diabrotica undecimpunctata howardi*, spotted cucumber beetle; Russian wheat aphid; *Schizaphis graminum*, greenbug; *Sitobion avenae*, English grain aphid; *Melanoplus femurrubrum*, redlegged grasshopper; *Melanoplus differentialis*, differential grasshopper, *Melanoplus sanguinipes*, migratory grasshopper; *Mayetiola destructor*, Hessian fly; *Sitodiplosis niosellana*, wheat midge; *Meromyza americana*, wheat stem maggot; *Hylemya coarctata*, wheat bulb fly; *Franklniella jusca*, tobacco thrips; *Cephus cinctus*, wheat stem sawfly; *Eriophyes tulipae*, wheat curl mite; Sunflower. *Suleima helianthana*, sunflower bud moth; *Homeosoma ellectellum*, sunflower head moth; *Zygoramma exclamationis*, sunflower beetle; *Bothyrus gibbosus*, carrot beetle; *Neolasioptera mur~feldtiana*, sunflower seed midge; *Cochylis hospes*, banded sunflower moth; *Rachiplusia nu*, agentina looper, *Smicronyx julvus*, red sunflower seed weevil; *Cylindrocopturus adspersus*, spotted sunflower stem weevil; Cotton: *Heliothis virescens*, tobacco budworm; *Helicoverpa zea*, bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franlinkiella jusca*, tobacco thrips; *Tetranychus cinnabarinus*, carmine spider mite; *Tetranychus urticae*, twospotted spider mite; Rice: *Diatraea saccharalis*, sugarcane borer, *Spodoptera ftugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhoper, *Blissus leucopterus*, chinch bug, *Acrosternum hilare*, green stink bug; *Pseudoplusia includens*, soybean looper; *Anticarsia gemmatalis*, velvetbean caterpillar, *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton boll worm; *Helicoverpa zea*, cotton bollworm; *Epilachna varivestis*, Mexican bean beetle; *Myzus persicae*, green peach aphid; *Empoasca jabae*, potato leafhopper; *Acrosternum hilare*, green stink bug; *Melanoplus femurrubrum*, redlegged grasshopper; *Melanoplus dififerentialis*, differential grasshopper; *Delia platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley. *Ostrinia nubilalis*, European corn borer; *Agrotis ipsilon*, black cutworm; *Schizaphis graminum*, greenbug; *Blissus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rgpe; *Brevicoryne brassicae*, cabbage aphid; Flea beetle, *Phyllotreta* spp.; Bertha Armyworm; *Mamestra configurata*; Diamondback Moth; *Plutella xylostella*; Alfalfa: alfalfa looper, *Autographa californica*; alfalfa snout beetle, *Otiorhynchus*

*ligusticii*; alfalfa caterpillar, *Colias eurytheme*; alfalfa blotch leafrunner, *Agronyza frontella*; Egyptian alfalfa weevil, *hypera brunneipeonis;* meadow spittlebug, *Philaerius spumarius*; spotted alfalfa aphid, *Theriophis meculata*; clover leaf weevil, *Hypera punctata*; pea aphid, *Acyrthosiphon pisum*; blue alfalfa aphid, *Acyrthosiphor kondoi*; green cloverworm, *Plathypena scabia*; clover root curculio, *Sitona hispidulus*; alfalfa seed chalcid, *Brachophagus roddi*; tarnished plantbug, *Lygus lineolaris*; Say stink bug, *Chlorochroa sayi*; velvetbean caterpillar, *Anticarsia ftiegiperda*, alfalfa weevil, *Hypera postica*; fall armyworm, *Spodoptera;* potato leafhopper, *Empoasca jabae*; soybean looper, *Psuedolusia includens*; Three cornered alfalfa hopper, *Spissistilus jestinus*; etc. Additional insect pests are known in the art. See, for example, Manya B. Stoetzel (1989) Common Names of Insects & Related Organisms, Entomological Society of America, herein incorporated by reference.

In addition, polynucleotides or polypeptides, agonists or antagonists of the invention may be useful in detecting, preventing, and/or confering resistance to other plant pests—including, but not limited to, insects, herbacious species, fungi, bacteria, viruse, and other pests disclosed herein. For example, polynucleotides or polypeptides, agonists or antagonists of the invention may, either directly, or indirectly, modulate (preferably decrease) the biosynthesis, assimilation, and/or concentration of a nutrient essential for pest survival. Alternatively, polynucleotides or polypeptides, agonists or antagonists of the invention may modulate (preferably increase) the biosynthesis of a metabolite and/or protein capable of decreasing the biosynthesis, assimilation, and/or concentration of a nutrient essential for pest survival. One example concerns the observation that plants harboring the cholesteral oxidase gene were resistant to boll weevil (*Anthonomus grandis* grandis Boheman) larvae (Purcell, J P., Biochem Biophys Res Commun, 196(3):1406–13 (1993)). Since cholesterol is an essential nutrient for most organisms, including insects, polynucleotides or polypeptides, agonists or antagonists of the invention capable of modulating levels and/or activity of cholesteral degrading enzymes, including cholesteral oxidase, would be useful in confering resistance to plant pests. In another example, plants expressing certain latherogens have been shown to confer resitance to some pathogens. Such latherogens have been identified as being able to interfere with collagen synthesis and/or aggregation.

In another embodiment, the polynucleotides or polypeptides, agonists or antagonists of the invention, can be used, either directly or indirectly, to detect, prevent, and/or confer resistance to any of the pests and/or diseases described herein through direct topical application to the plants for which protection is desired. For example, several protein- and/or peptide-based commercial pesticides have recently been introduced into the marketplace that provide broad pesiticide resistance to pests when applied directly to the plant—Messenger, from Eden Bioscience, and Actigard, from Novartis Crop Protection (Nat. Biotech., 18:595 (2000)). Messenger is based upon the *Erwinia amylovara* harpin gene (Wei, Z., Science, 257:85–88 (1992)). Such protein/peptide-based pesticides have been shown to activate the systemic acquired resistance (SAR) pathway in plants. The invention encompasses additional modes of action for confering resistance to plant pests, though direct or indirect activation of the SAR pathway by the polynucleotides or polypeptides, agonists or antagonists of the invention, is preferred. The method of topical application, including any formulation requirements, will vary based the unique characterisitics of each polynucleotide or polypeptide, agonist or antagonist of the invention. In addition, polynucleotides or polypeptides, agonists or antagonists of the invention that provides plant pathogen resistance may also have other beneficial uses, such as, for example, enhancing plant growth.

Plant Defense

A polypeptide or polynucleotide and/or agonist or antagonist of the present invention can be used to increase a plants defense mechanisms against either environmental or pathogenic stresses (e.g., viral, fungal, mycoplasma, bacterial, nematode, herbicidal, insecticidal, acid rain, drought, chemical, etc.). Such defense mechanisms may be a combination of structural characteristics (i.e., to serve as a physical barrier to inhibit a pathogen, for example, from entering or spreading throughout the plant), and biochemical reactions either on the scale of the whole plant or of individual cells (e.g., producing substances that are either toxic to the pathogen, or create an environment that is non-permissive for pathogen survival, etc.).

Structurally, a polypeptide or polynucleotide and/or agonist or antagonist of the present invention, may be useful for increasing the number of trichomes, increasing the thickness and/or composition of wax secretions or the waxy layer, increasing the thickness and/or composition of the cuticle, altering the structure of the epidermal cell wall, altering the size, shape, and/or location of the stomata and lenticels, inducing the plant to create or increase a layer of thick-walled cells (e.g., cork cell layer, etc.), increasing the thickness and/or composition of the outer epidermal cell wall, inducing the formation of an abscission layer, induce the formation of tyloses, induce the production and/or deposition of gums, inducing the thickening of the outer parenchyma cell layer of the cell wall, inducing the thickening of the cell wall, inducing the deposition of callose papillae in the inner layer of the cell wall, inducing a necrotic or hypersensitive defense reaction in cells and/or tissues (i.e., cell death), inducing the polymerization of oxidized phenolic compounds into lignin-like substances to structurally interefer with pathogen development, and/or inducing a cytoplasmic defense reaction.

Biochemically, a polypeptide or polynucleotide and/or agonist or antagonist of the present invention, may be useful for releasing pathogenic inhibitors into the plants environment, releasing fungitoxic exudates, and/or releasing phenolic compounds (e.g., protocatechioc acid, catechol, etc.). Alternatively, a polypeptide or polynucleotide and/or agonist or antagonist of the present invention, may be useful for increasing the synthesis of phenolic compounds (e.g., chlorogenic acids, caffeic acids, scopoletin, oxidation products of phenolic compounds, phytoalexins (see, Bell et al., Ann Rev. Plant Physiol. 32, 1981, for specific examples of phytoalexins), phaseolin, rishitin, kievitone, pisatin, glyceollin, gossypol, capsidiol etc.), tannins, and/or saponins (e.g., tomatine, avenacin, etc.) within the cells and tissues of the plant. Alternatively, a polypeptide or polynucleotide and/or agonist or antagonist of the present invention, may be useful for increasing the expression of plant hydrolytic enzymes (e.g., glucanases, chitinases, etc.) that may cause degradation of the pathogen cell wall, etc.

In another embodiment, a polypeptide or polynucleotide and/or agonist or antagonist of the present invention, may be useful for inhibiting the expression of recognition factors essential for host-pathogen interaction (e.g., specific oligosaccharides, carbohydrate moieties, receptors, ligands, proteins, glycoproteins, lectins, etc.). For example, a polypeptide or polynucleotide and/or agonist or antagonist of the present invention, may be useful for inhibiting the expression of a protein that serves as a target for a pathogenic toxin, thus rendering the host insensitive to the toxin.

In another embodiment, a polypeptide or polynucleotide and/or agonist or antagonist of the present invention, may be useful in inhibiting the ability of the plants metabolic machinary to complete essential steps required for a competent pathogenic response (e.g., inhibiting the ability of plant ribosomes to recognize the pathogens nucleic acid, such as a viral nucleic acid; and/or inhibiting the ability of the plants DNA polymerase machninary to recognize and/or synthesize pathogenic DNA; or inhibiting the plants ability to catalyze a specific enzymatic step essential to eliciting a pathogenic response, etc.)

In yet another embodiment, a polypeptide or polynucleotide and/or agonist or antagonist of the present invention, may be useful for inhibiting either the production or transport or retention of essential nutrients required for a permissive pathogenic infection (e.g., inhibiting the transport of non-essential minerals or vitamins required for a pathogenic response, etc.).

In one embodiment of the invention, a polypeptide or polynucleotide and/or agonist or antagonist of the present invention, may be useful for increasing the expression or activity of phenol oxidizing enzymes (e.g., polyphenoloxidases, peroxidase, etc.), increasing the expression or activity of phenylalanine ammonia lyase, increasing the activity or expression of proteins capable of forming pectin salts or pectin complexes, etc.

In a further embodiment, a polypeptide or polynucleotide and/or agonist or antagonist of the present invention, may be useful for either directly or indirectly inhibiting the activity of a pathogenic protein essential to eliciting an infection (e.g., inhibiting the enzymatic activity of the protein, such as for a hydrolytic enzyme, for example, inhibiting the proteins ability to bind to a receptor or ligand, inhibiting protein-protein or protein-DNA interactions of the pathogenic protein, etc.). Specifically, a polypeptide or polynucleotide and/or agonist or antagonist of the present invention, may be useful for either directly or indirectly inhibiting wildfire toxin, chlorosis-inducing toxins, tabtoxin, phaseoloyoxin, rhizobitoxine, wilt-inducing bacterial polysaccharides, amylovorin, glycopeptide toxins, peptide toxins, syringomycin, tagetitoxin, helminthosporoside, victorin, helminthospoium maydis T-toxin, helminthospoium carbonum toxin, periconia circinata toxin, phyllosticta maydis toxin, alternaria toxins, fusarial wilt toxins, ophiobolin, helminthosporal, terpinoid toxins, fusicoccin, pyricularin, colletotin, alternaric acid, tentoxin, phytotoxins, zinniol, tentoxin, ascochitine, diaporthin, skyrin, *Didyruella applanata* toxin, *Myrothecium roridum* toxin, *Leptosphaerulina briosiana* toxin, *Alternaria tenuis* phenolic toxins, *Cercospora beticola* toxin, *Verticillium albo-atrum* toxin, *Phytophthora nicotianae* var. *parasitica* toxin, *Phytophthora megasperma* var. *sojae* toxin, *Ceratocystis ulmi* toxins, peptidorhamnomannan, *Stemphylium botryosum* toxins, stemphylin, stemphyloxin, *Pyrenophora teres* toxins, N-(2-amino-2-carboxyethyl) aspartic acid, aspergillomarasmine A, and Rhynchosporosides toxins, for example.

In another embodiment, a polypeptide or polynucleotide and/or agonist or antagonist of the present invention, may be useful for either increasing or inducing the production of cyanogenic glycosides or esters, increasing the activity or expression of hydrolytic enzymes capable of hydrolyzing cyanogenic glycosides or esters, increasing the activity or expression of enzymes capable of releasing cyanide into plant cells and tissues, increasing the activity or expression of enzymes capable of detoxifying cyanide (e.g., formamide hydro-lyase, etc.) and/or increasing the expression of b-proteins, etc.

In yet a further embodiment, a polypeptide or polynucleotide and/or agonist or antagonist of the present invention, in addition to the non-coding 5' or 3' region of any of the polynucleotides of the present invention, and/or fragments thereof, may be useful for producing viral coat proteins, bacterial or fungal proteins, lipoproteins, polysaccharides, yeast RNA, polyanions, polyacrylic acid, salicylic acid, and/or 2-chloroethylphosphonic acid, in the plant, for example. Such proteins and/or compounds have been shown to elicite a local resistence response to plant pathogens when applied systemically or topically to the plant.

In another embodiment, a polypeptide or polynucleotide and/or agonist or antagonist of the present invention, may be useful for either increasing or inducing the production of secondary metabolites, which include, but are not limited to the following: acetyl salicylic acid, aconitine, atropine, cytisine, germinine, cardiac glycosides (e.g., calotropin, oleandrin, etc.), linarine, quinine, atropine, taxine, cicutoxin, hyoscyamine, pyrethrin, rotenone, camphor, etc.

In another embodiment, a polypeptide or polynucleotide and/or agonist or antagonist of the present invention, may be useful for either increasing or inducing the production of non-protein amino acids, which include, but are not limited to the following: b-cyanoalanne, azetidine 2-carboxylic acid, canavanine, 3,4-dihydroxyphenylalanine, etc.

In another embodiment, a polypeptide or polynucleotide and/or agonist or antagonist of the present invention, may be useful for either increasing or inducing the production of terpenes, which include, but are not limited to the following: 1.8 cineole, camphor, a-pinene, b-pinene, camphene, thujone, etc.

In yet another embodiment, a polypeptide or polynucleotide and/or agonist or antagonist of the present invention may either directly or indirectly inhibit the infectious agent, without necessarily increasing the plants defense mechanisms.

The present invention encompasses the application of one, two, three, four, or more, including any combination thereof, of any of the methods of increasing plant defense mechanisms against either an environmental or infectious agent described above and elsewhere herein. Additional methods of increasing a plants defense mechanisms are known in the art. Additionally, a list of compounds and/or proteins that could serve as targets for increased production or expression by the use of a polynucleotide or polypeptide of the present invention to increase a plants defense mechanisms are known in the art (see, for example, Agrious, N. C., supra; Goodman, R. N., in "The Biochemistry and Physiology of Plant Disease", University of Missouri Press, Columbia, 1986; and Lambers, H., et al., in "Plant Physiological Ecology", Spinger-Verlag, New York, (1998); which are hereby incorporated herein by reference in their entirety).

Plant Hormones

A polynucleotide or polypeptide and/or agonist or antagonist of the present invention can be used to modulate the hormone levels within a plant (including any of its cells, tissues, and/or organs, etc.). Examples of hormones that may be modulated by the present invention, either directly or indirectly, generally include, but are not limited to, the following: auxins, indoleacetic acid, gibberellins, cytokinins, ethylene, abscisic acid, polyamines, jasmonates, tuberonic acid, salicylic acid, systemin, brassinolides, zeatin; and specifically, indole-3-acetic acid, indole-3-butyric acid, 4-chloroindole-3-acetic acid, indole-3-acetyl-1-O-B-D-glucose, indole-3-acetyl-myoinositol, jasmonic acid, methyl jasmonate, kinetin, including any known derivatives of the hormones described above, etc. In this context, modulate should be applied to mean a quantitative, or qualitative increase, decrease, induction, or termination, of the expression levels of any of the aforementioned hormones. Additional examples of plant hormones are known in the art (see, for example, Davies, P. J., in "Plant Hormones: Physiology, Biochemistry, and Molecular Biology", Kluwer Academic Publishers, Boston, 1995; which is hereby incorporated by reference in its entirety herein).

A polynucleotide or polypeptide and/or agonist or antagonist of the present invention capable of modulating plant auxin levels, would necessarily be capable of the following, non-limiting, effects on a plant: stimulating cell enlargement, stimulating stem growth, stimulating cell division in the cambium, stimulating differentiation of phloem and xylem, stimulating root initiation on stem cuttings, stimulating the development of branch roots, stimulating the differentiation of roots, mediating the bending (tropistic) response of shoots and roots to gravity and light, repression of lateral buds, delay of leaf senscence, inhibition or promotion of leaf and fruit abscission (via ethylene), induction of fruit setting and growth, enhancement of assimilate transport via phloem, delay of fruit ripening, promotion of flowering in Bromeliads, stimulating flower growth, promotion of femaleness in dioecious flowers, and stimulating the production of ethylene, for example.

A polynucleotide or polypeptide and/or agonist or antagonist of the present invention capable of modulating plant gibberellin levels, would necessarily be capable of the following, non-limiting, effects on a plant stimulating cell division and cell elongation, inducing hyperelongation, inducing bolting, inducing stem elongation in response to long days, inducing germination, inducing germination in seeds in the absence of stratification or hardening, stimulating production of a-amylase, inducing fruit setting and growth, and inducing maleness in dioecious flowers, for example.

A polynucleotide or polypeptide and/or agonist or antagonist of the present invention capable of modulating plant cytokinin levels, would necessarily be capable of the following, non-limiting, effects on a plant: inducing cell division in the presence of auxin, inducing cell division in crown gall tumors, inducing cell division in apical meristem, inducing cell division in rapidly dividing cells, promoting shoot initiation, inducing bud formation, inducing growth of lateral buds, releasing lateral bud growth from apical dominance, inducing cell enlargement, inducing leaf expansion, enhancing stomatal opening, stimulating the accumulation of chlorophyll, inducing the conversion of etioplasts to chloroplasts, and delaying leaf senescence, for example.

A polynucleotide or polypeptide and/or agonist or antagonist of the present invention capable of modulating plant ethylene levels, would necessarily be capable of the following, non-limiting, effects on a plant: releasing the plant from dormancy, inducing shoot and root growth and differentiation, inducing adventitious root formation, inducing leaf and fruit abscission, inducing flowering, inducing femaleness in dioecious flowers, inducing flower opening, inducing flower and leaf senescence, and inducing fruit ripening, for example.

A polynucleotide or polypeptide and/or agonist or antagonist of the present invention capable of modulating plant abscisic acid levels, would necessarily be capable of the following, non-limiting, effects on a plant: inducing stomatal closure, inhibition of shoot growth, inducing storage protein synthesis in seeds, inhibition of a-amylase production in germinating cereal grains, induction of some aspects of dormancy, and induction of proteinase inhibitor synthesis, for example.

A polynucleotide or polypeptide and/or agonist or antagonist of the present invention capable of modulating plant polanine levels, would necessarily be capable of the following, non-limiting, effects on a plant: regulation of growth and development of plant cells and tissues, modulating the synthesis of macromolecules, modulating the activity of macromolecules, stabilizing cellular plasma membrane, decreasing leakage of betacyanin from wounded tissue, preservation of thylakoid strucuture in excised barley leaves, counteraction of hormone-induced affects on the cell membrane, binding to nucleic acids, protection of nucleic acids from alkylating agents, controlling chromosome condensation, controlling nuclear membrane dissolution during preprophase, and modulating the structure and function of tRNA's, for example.

A polynucleotide or polypeptide and/or agonist or antagonist of the present invention capable of modulating plant jasmonate levels, would necessarily be capable of the following, non-limiting, effects on a plant: inhibition of plant growth, inhibition of seed germination, promotion of senescence, promotion of abscision, promotion of tuber formation, promotion of fruit ripening, promotion of pigment formation, promotion of tendril coiling, induction of proteinase inhibitors, and inhibit insect infestation, for example.

A polynucleotide or polypeptide and/or agonist or antagonist of the present invention capable of modulating plant salicylic acid levels, would necessarily be capable of the following, non-limiting, effects on a plant: induction of thermogenesis, providing resistence to pathogens via induction of pathogenesis related proteins, enhancement of flower longevity, inhibition of ethylene biosynthesis, inhibition of seed germination, inhibiting the wound response, couteracting the plants response to abscisic acid, for example.

A polynucleotide or polypeptide and/or agonist or antagonist of the present invention capable of modulating plant brassinosteroid levels, would necessarily be capable of the following, non-limiting, effects on a plant: promotion of stem elongation, inhibition of root growth, inhibition of root development, promotion of ethylene biosynthesis, and promotion of epinasty, for example.

The polynucleotides or polypeptide and/or agonist or antagonist of the present invention may modulate one, two, three, or more, or any combination of the above, hormones in a plant. Additional effects of hormones on a plant, including its cells, tissues, and organs are known in the art and the aforementioned plant hormone effects should not be construed as limiting the utility of any of the polynucleotide or polypeptides of the present invention.

Regeneration

A polynucleotide or polypeptide and/or agonist or antagonist of the present invention can be used to differentiate, proliferate, and/or attract cells, leading to the regeneration of tissues. (See, Science 276:59–87 (1997).) The regeneration of tissues could be used to repair, replace, and/or protect tissue damaged by environmental insults (e.g., herbicidal, photobleaching, acid rain, drought, nematodes, insects, chemical, etc.), disease (e.g., fungal, viral, bacterial, mycoplasmal, etc.), necrosis, hypersensitive reaction, and/or cytokine damage.

Tissues that could be regenerated using polynucleotides or polypeptides of the present invention include tissues (e.g., apical meristem, lateral shoot, lateral bud, leaf, pith, vascular cambium, stem, phloem, xylem, cortex, epidermis, lateral root, root meristem, cuticle, etc.), in addition to cellular organelles and constituents (vacuole, mitochondrion, chloroplast, plastid, lysosomes, peroxisomes, glyoxysomes, cytoplasm, endoplasmic reticulum, ribosomes, vacuolar membrane, nucleus, nuclear membrane, plasmodesmata, scherosomes, microbodies, primary cell wall, etc.).

Nutrients

A polynucleotide or polypeptide and/or agonist or antagonist of the present invention can be used to modulate the plants nutritional status through a number of different mechanisms. For example, A polynucleotide or polypeptide and/or agonist or antagonist of the present invention can be used to modulate the plants ability to retain a particular nutrient, to modulate the plants ability to synthesize a particular nutrient, to modulate the plants ability to assimilate a nutrient, to modulate the plants ability to absorb or uptake a particular nutrient, to modulate the plants ability to transport a particular nutrient, to modulate the plants ability to store a particular nutrient, to modulate the plants ability to survive under nutrient deficiencies, and to prevent, detect, and/or provide resistance to nutrient defiency symptoms and traits.

Specific examples of nutrients that may be modulated in a plant by a polynucleotide or polypeptide and/or agonist or antagonist of the present invention include the following, non-limiting, nutrients: carbon, hydrogen, oxygen, nitrogen, phosphorus, sulfur, potassium, calcium, magnesium, boron, chlorine, copper, iron, manganese, zinc, molybdenum, cobalt, selenium, silicon, sodium, nickel water, carbon dioxide, in addition to metabolic by-products, etc. Additional nutrients essential to maintaining plant homeostasis are known in the art.

A polynucleotide or polypeptide and/or agonist or antagonist of the present invention capable of modulating plant boron levels, may be capable of preventing, detecting, alleviating, and/or confering resistance to the following, non-limiting, symptoms of plant boron deficiency: terminal leaf necrosis, premature leaf abscission layer formation, terminal shoot internode shortening, blackening and/or death of apical meristem tissue, shortening of root shoots, plant dwarfing, plant stunting, impairment of flower development, impairment of seed development, etc.

A polynucleotide or polypeptide and/or agonist or antagonist of the present invention capable of modulating plant calcium levels, may be capable of preventing, detecting, alleviating, and/or confering resistance to the following, non-limiting, symptoms of plant calcium deficiency: chlorotic leaves, leaf curling, leaf rolling, degradation of meristematic tissues in stems and roots, meristematic tissue death, decreased root development, decreased root fiber content, decreased fruit development, etc.

A polynucleotide or polypeptide and/or agonist or antagonist of the present invention capable of modulating plant chlorine levels, may be capable of preventing, detecting, alleviating, and/or confering resistance to the following, non-limiting, symptoms of plant chlorine deficiency: leaf tip wilting, leaf chlorosis, leaf bronzing, basipetal leaf necrosis proximal to areas of wilting, etc.

A polynucleotide or polypeptide and/or agonist or antagonist of the present invention capable of modulating plant copper levels, may be capable of preventing, detecting, alleviating, and/or confering resistance to the following, non-limiting, symptoms of plant copper deficiency: terminal shoot wilting, terminal shoot death, fading of leaf color, reduction of carotene in plant cells and tissues, reduction of other pigments in plant cells and tissues, etc.

A polynucleotide or polypeptide and/or agonist or antagonist of the present invention capable of modulating plant iron levels, may be capable of preventing, detecting, alleviating, and/or confering resistance to the following, non-limiting, symptoms of iron deficiency: interveinal white chlorosis of young leaves first, chlorisis of aerial tissues, aerial tissue necrosis, bleaching of leaves, scorching of leave margins and tips, etc.

A polynucleotide or polypeptide and/or agonist or antagonist of the present invention capable of modulating plant magnesium levels, may be capable of preventing, detecting, alleviating, and/or confering resistance to the following, non-limiting, symptoms of magnesium deficiency: mottling chlorosis with green veins and leaf web tissue yellow or white on old leaves first, wilting of leaves, formation of leaf ascission layer in the absence of the wilting stage, necrosis of plant cells and tissues, etc.

A polynucleotide or polypeptide and/or agonist or antagonist of the present invention capable of modulating plant manganese levels, may be capable of preventing, detecting, alleviating, and/or confering resistance to the following, non-limiting, symptoms of manganese deficiency: mottling chlorosis with green veins and leaf web tissue yellow or white on young leaves first, then spreading to old leaves, yellowish green stem, hardening and/or wooding of stem, reduction of carotene, etc.

A polynucleotide or polypeptide and/or agonist or antagonist of the present invention capable of modulating plant molybdenum levels, may be capable of preventing, detecting, alleviating, and/or confering resistance to the following, non-limiting, symptoms of molybdenum deficiency: light yellow chlorosis of leaves, failure of leaf blade expansion, etc.

A polynucleotide or polypeptide and/or agonist or antagonist of the present invention capable of modulating plant nitrogen levels, may be capable of preventing, detecting, alleviating, and/or confering resistance to the following, non-limiting, symptoms of nitrogen deficiency: stunting plant growth of young plants, yellowish green leaves in young plants, light green leaves in older leaves followed by yellowing and drying or shedding, increased accumulation of anthocyanins in veins, thin stem, spindely appearance of plant, reduced flowering, etc.

A polynucleotide or polypeptide and/or agonist or antagonist of the present invention capable of modulating plant phosphorus levels, may be capable of preventing, detecting, alleviating, and/or confering resistance to the following, non-limiting, symptoms of phosphorus deficiency: stunting of young plants, dark blue-green leaves with purplish undertones, slender stems, increased accumulation of anthocyanin in leaves, necrosis of leaves, cessation of meristematic growth, decreased rate of fruit ripening, plant dwarfing at maturity, etc.

A polynucleotide or polypeptide and/or agonist or antagonist of the present invention capable of modulating plant potassium levels, may be capable of preventing, detecting, alleviating, and/or confering resistance to the following, non-limiting, symptoms of potassium deficiency: dark green leaves, pale green monocotyledon leaves, yellowing streaking of monocoytledon leaves, marginal chlorosis of leaves, necrosis of leaves appearing first on old leaves, wrinkling of veins, currugating of veins, crinkling of veins, etc.

A polynucleotide or polypeptide and/or agonist or antagonist of the present invention capable of modulating plant sulfur levels, may be capable of preventing, detecting, alleviating, and/or confering resistance to the following, non-limiting, symptoms of sulfur deficiency: light green to yellow leaves appearing first along veins of young leaves, slender stems, etc.

A polynucleotide or polypeptide and/or agonist or antagonist of the present invention capable of modulating plant zinc levels, may be capable of preventing, detecting, alleviating, and/or confering resistance to the following, non-limiting, symptoms of zinc deficiency: chlorosis of leaves and/or necrosis of leaves affecting young leaves first, rosetting, premature formation of ascission layer of leaves, whitish chlorotic streaks between veins in older laves, whiting of upper leaves in monocotyledons, chlorosis of lower leaves in dicotyledons, etc.

Additional symptoms of plant nutrient deficiencies are known in the art (see for example, Noggle, G. R., and Fritz, G. J., in "Introductory Plant Physiology", $2^{nd}$ edition, Prentice-Hall, Inc., Englewood Cliffs, 1983).

In a specific embodiment, a polynucleotide or polypeptide and/or agonist or antagonist of the present invention may be able to modulate plant nutrient levels either directly or indirectly by increasing the activity, kinetics, and/or expression of transport proteins, ion channels, and/or ion carrier proteins.

In another embodiment, a polynucleotide or polypeptide and/or agonist or antagonist of the present invention may be able to modulate plant nutrient levels by either directly or indirectly increasing or inducing the secretion of mineral solubilizing or mineral stabilizing compounds or chelating compounds (e.g., citric acid, malic acid, pisidic acid, etc.). Alternatively, the secreted compound may be an organic chelating compound (e.g., phytometallophore, see for example, Cakinak et al., Plant Soil, 180:183–189, (1996)). Alternatively, the secreted compound is a root exudate, such as an organic acid (e.g., lactic, acetic, formic, pyruvic, succinic, tartaric, oxalic, citric, isocitric, aconitic, etc.), carbohydrate, amino acid, or polysaccharide capable of assimilating carbon (see, for example, Paul, E. A., and Clark, F. E., in "Soil microbiology and biochemistry", Academic Press, San Diego, (1989)).

In another embodiment, a polynucleotide or polypeptide and/or agonist or antagonist of the present invention may be able to modulate plant nutrient levels by modulating, either directly or indirectly, the activity, kinetics, and/or expression of phosphatase enzymes, nitrate reductase enzymes, citrate synthesis enzymes, etc.

In another embodiment, a polynucleotide or polypeptide and/or agonist or antagonist of the present invention may be able to modulate plant nutrient levels by modulating the active transport and/or passive transport mechanisms of the plant. Alternatively, a polynucleotide or polypeptide and/or agonist or antagonist of the present invention may be able to modulate plant nutrient levels by modulating the inter- and intra-tissue and/or cellular transport of nutrients in the plant (e.g., transport through the phloem, xylem, desmosomes, etc.). Additional mechanisms of modulating plant nutrient transport are known in the art (see, for example, Lambers, H., et al., in "Plant Physiological Ecology", Spinger-Verlag, New York, (1998); which is hereby incorporated herein by reference in its entirety).

Biotic Associations

A polynucleotide or polypeptide and/or agonist or antagonist of the present invention may increase the plants ability, either directly or indirectly, to initiate and/or maintain biotic associations with other organisms. Such associations may be symbiotic, nonsymbiotic, endosymbiotic, macrosymbiotic, and/or microsymbiotic in nature. In general, a polynucleotide or polypeptide and/or agonist or antagonist of the present invention may increase the plants ability to form biotic associations with any member of the fungal, bacterial, lichen, mycorrhizal, cyanobacterial, dinoflaggellate, and/or algal, kingdom, phylums, families, classes, genuses, and/or species.

Specific, non-limiting, examples of organisms known to form biotic associations with a plant are: ectomycorrhizas (e.g., members of the Diperocarpaceae, Pinaceae, Fagaceae, Myrtaceae, Salicaceae, Betulaceae, Fabaceae, etc.), endomycorrhizas, vesicular arbuscular mycorrhiza (e.g., members of the Glomales), nonmycorrhizal (e.g., members of tge Brassicaceae, Caryophyllaceae, Chenopodiaceae, Lecythideceae, Proeaceae, Restionaceae, Sapotaceae, Urticaceae, Zygophyllaceae, etc.), symbiotic N2 fixing organisms (e.g., members of the Rhizobium, Bradyrhizobium, Sinorhizobium, Mesorhizobium, Azorhizobium, etc.), nonsybiotic N2 fixing organisms (e.g., Azospirillum, etc.), endosymbiontic organisms (e.g., members of the Clavicipitaceae, Ascomycetes, etc.), etc. Additional organisms capable of forming biotic associations with plants are known in the art and are encompassed by the invention (see, for example, Lambers, H., et al., in "Plant Physiological Ecology", Spinger-Verlag, New York, (1998); Raven, P. H., et al., in "Biology of Plants", $5^{th}$ Edition, Worth Publishers, New York, (1992); which are hereby incorporated herein by reference in its entirety The mechanism by which a polynucleotide or polypeptide and/or agonist or antagonist of the present invention may increase the plants ability, either directly or indirectly, to initiate and/or maintain biotic associations is variable, though may include, modulated secretions of organic acids, phenolic compounds, nutrients, or the increased expression of a protein required for host-biotic organisms interactions (e.g., a receptor, ligand, etc.). Additional mechanisms are known in the art and are encompassed by the invention.

In an alternative embodiment, a polynucleotide or polypeptide and/or agonist or antagonist of the present invention may decrease a plants ability to form biotic associations with a plant. Such a decrease may be due to increasing the plants ability to utilize, obtain, store, and/or synthesize essential nutrients that the biotic organism supplied to the plant through the association.

Mechanisms by which a plant could inhibit colonization of biotic associating organisms are known in the art (see, for example, Smith, S. E., and Read, D. J., in "Mycorrhizal Symbiosis", Academic Press, London, 1997, etc.). For example, in low phosphorus containing soils, a plant may form beneficial symbiosis colonization with a species capable of providing phosphorus. However, in soils of high phosphorus content, such colonization could be inhibited by the plant. Thus, a polynucleotide or polypeptide of the invention could increase the plants ability to live in phosphorus depleted soils by enabling the plant to assimilate phosphorus through a mechanism previously not endogenous to the plant, for example.

Pheromones

In another embodiment, a polynucleotide or polypeptide and/or agonist or antagonist of the present invention may increase the plants ability to synthesize and/or release a pheromone. Such a pheromone may attract predatory organisms to the plant that may feed on plant pests or infectious agents. For example, recent studies of the aphid *Acyrthosi-*

*phon pisum* have shown that feeding by the aphid alters the composition of volatiles released by the plant and that these compounds act as synomones for the aphids foraging parasitoid, *Aphidius ervi*. Additional studies have shown that other pheromones released by the plant in response to aphid foraging, namely(E)-beta-farnesene, may also attract other aphid predators, such as the lacewing *Chrysoperla carnea* and the seven-spot ladybird, *Coccinella septempunctata*.

A polynucleotide or polypeptide and/or agonist or antagonist of the present invention may modulate the biosynthesis and/or release of pheromones, volatiles having pheromone-like effects, volatiles having kairomone effects, volatiles having synomones effects, and/or may releases (E)-beta-farnesene specifically.

Alternatively, a polynucleotide or polypeptide and/or agonist or antagonist of the present invention may modulate the release of pheromones, indirectly, through the induction of the following, non-limiting, compounds, compounds from the octadecanoid signalling pathway, structurally non-related amino acid conjugates such as the bacterial phytotoxin coronatine, the synthetic indanoyl-isoleucine, or amino acid conjugates of linolenic, and/or volatile terpenoids, such as members of the sesqui- and diterpenoids. Preferably, any of the pheromones, and/or volatiles released from the plant, or induced, by a polynucleotide or polypeptide and/or agonist or antagonist of the invention have behavioral effects on predators and/or pests of plants. Other examples of known pheromones or volatiles released by a plant having behavioral modulating effects on plant pest predators and/or plant pests are known in the art (see, Boland W., et al., Novartis Found Symp, 223:110–26 (1999); Wadhams L J., Novartis Found Symp, 223:60–7 (1999); Tumlinson J H, et al., Novartis Found Symp, 223:95–105 (1999)).

In yet another embodiment, a polynucleotide or polypeptide and/or agonists or antagonists of the present invention may modulate the biosynthesis of furanones. Furonones are naturally occuring compounds found in a variety of plants that have been shown to have pheromone-like effects, anti-bacterial effects, anti-viral effects, etc., on a variety of organisms. For example, 5-MethylShydroxy-3(2H)-furanone is a male pheromone in the cockroach *Eurycolis florionda* (Walker) and the 2,5-dimethyl derivative deters fungal growth on strawberries and is an important component of the attractive aroma of the fruit. The red seaweed *Delisea pulchra* (Greville) Montagne produces a range of brominated furanones which prevent colonisation of the plant by bacteria by interfering with the acylated homoserine lactone (AHL) signalling system used by the bacteria for quorum sensing. In addition, furonones have been shown to have mutagenic properties in bacteria and viruses, and thus could serve as anti-bacterials and anti-virals (Colin, Slaughter J, Biol Rev Camb Philos Soc, 74(3):259–76 (1999).

Chemotaxis

A polynucleotide or polypeptide and/or agonist or antagonist of the present invention may have chemotaxis activity. A chemotaxic molecule attracts or mobilizes cells to a particular site in the plant or animal body, such as inflammation, infection, or site of hyperproliferation. The mobilized cells can then fight off and/or heal the particular trauma or abnormality.

A polynucleotide or polypeptide and/or agonist or antagonist of the present invention may increase chemotaxic activity of particular cells. These chemotactic molecules can then be used to detect, prevent, and/or alleviate inflammation, infection, hyperproliferative diseases, disorders, and/or conditions, or any plant disorder by increasing the number of cells targeted to a particular location in the plants body. For example, chemotaxic molecules can be used to treat, prevent, and/or diagnose wounds and other trauma to tissues by attracting cells to the injured location.

It is also contemplated that a polynucleotide or polypeptide and/or agonist or antagonist of the present invention may inhibit chemotactic activity. These molecules could also be used to detect, prevent, and/or alleviate diseases, disorders, and/or conditions. Thus, a polynucleotide or polypeptide and/or agonist or antagonist of the present invention could be used as an inhibitor of chemotaxis.

In an alternative embodiment, a polynucleotide or polypeptide and/or agonist or antagonist of the present invention may modulate the ability of a plant to sense the presence of plant neighbors (i.e., chemoperception). Such chemoperceptive modulation may come in the form of sensing the presence of plant hormones (e.g., jasmonate, etc.), heat exchange differential, and/or allelochemical detection (see, for example, Boller, Ann Rev. Plant Physiol. Plant Mol. Biol., 46:189–214, (1995)).

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells that express the polypeptide, either as a secreted protein or on the cell membrane. Preferred cells include cells from plants, yeast, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule. Moreover, the identification of such molecules may be obtained through the application of the yeast 2 or 3 hybrid system (see for example, Wallach D, et al., Curr Opin Immunol., 10(2):131–6, (1998); Young K H., Biol Reprod., 58(2):302–11, (1998); and Fernandes, P B., Curr Opin Chem Biol., 2(5):597–603 (1998); which are hereby incorporated by reference in their entirety herein, including the methods disclosed and the references cited therein). Further, the identification of such molecules may be obtained through the application of additional screening technologies which include, but are not limited to, the following issued U.S. Pat. Nos. 5,284,746; 5,576,210; 5,691,188; 5,846,819; and International Publication No. WO 95/34646; which are hereby incorporated by reference in their entirety herein, including the methods disclosed and references cited therein.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniques 24(2):308–13 (1998) (each of these patents and publications are hereby incorporated by reference). The techniques of DNA shuffling are known in the art and more particularly described elsewhere herein.

All of the assays referenced above, and elsewhere herein, can be used as diagnostic or prognostic markers. The molecules discovered using these assays may be used to detect, prevent, and/or confer resistance to a disease or to bring about a particular result in an organism (e.g., vessel growth, etc.) by activating or inhibiting the polypeptide/molecule. Moreover, the assays can discover agents which may inhibit or enhance the production of the polypeptides of the invention from suitably manipulated cells or tissues.

Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (b) determining if a biological activity of the polypeptide has been altered.

Antisense and Ribozyme (Antagonists)

In preferred embodiments, the invention encompasses antagonists which correspond to the polynucleotide sequences shown in SEQ ID NO:X, the complimentary strand thereof, and/or to the polynucleotide sequences contained within the deposited clone. Antisense technology results in modulation (i.e., complete or partial inhibition), of the expression of a particular protein through direct inhibition of the proteins mRNA. Antisense nucleic acids may be in the form of DNA, RNA, PNA, triple helix, quad helix, a chimeric mixture of any of these aforementioned types (e.g., DNA:RNA, PNA:RNA, PNA:DNA, etc.), and may be single or double stranded. Antisense nucleic acids modulate gene expression by binding to the RNA of the gene of interest, effectively inhibiting translation. Such intereactions may rely follow typical Watson-Crick base pair recognition, or the case of a triple or quad helix, may rely upon Hoogsteen basepair recognition.

The antisense nucleic acids may be transiently generated within the organism (e.g., sequence contained within an inducible or constitutively expressed vector introduced into the cells of an organism), stably generated within the organism (e.g., sequence contained within an inducible or constitutively expressed vector introduced into the cells of an organism using transgenic methods, including viral integration, etc.) or may be exogenously administered. For a nucleic acid to serve an antisense role, it is only necessary that it has sequence homology to the sense RNA product of the gene of interest. A number of methods of administering antisense nucleic acids, their compositions, and designs are known in the art and encompassed by the invention (see for example, Agrawal S, et al., Mol Med Today. 2000 February; 6(2):72–81; Yacyshyn B R, et al, Can J Gastroenterol. 1999 November;13(9):745–51; Mrsny R J., J Drug Target 1999; 7(1):1–10; Toulme J J, et al, Nucleic Acids Symp Ser. 1997;(36):39–41.), Okano, Neurochem., 56:560 (1991); Oligodeoxynucleotides as Antisense Inhibitors of Gene Expression, CRC Press, Boca Raton, Fla. (1988); and Cooper S R, et al., Pharmacol Ther. 1999 May–June; 82(2–3):427–35). Likewise, a number of methods have been developed regarding the application of triple helix antisense technology to modulating gene expression (see, for example, Gowers D M, et al, Nucleic Acids Res. Apr. 1, 1999;27(7):1569–77; and Chan PP, et al., J Mol Med. 1997 April,75(4):267–82).

Antisense technology has wide-ranging applications in plants. For example, antisense RNA has been shown to effectively downregulate a variety of plant genes as described by Shimada, et al., Theor. Appl. Genet., 86:665–672, (1993); Kull, et al., J. Genet. Breed., 49:67–76, (1995)., Slabas and Elborough, WO 97/07222; Knutzon et al., Proc. Natl. Acad. Sci. USA, 89:2624–2628, (1992), and Baulcombe D C., Plant Mol. Biol. 1996 October, 32(1–2): 79–88).

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Antisense oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372:333–335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The antisense oligonucleotide may be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. USA 86:6553–6556; Lemaitre et al., 1987, Proc. Natl. Acad. Sci.84:648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549).

The oligonucleotide can also be a peptido-nucleic acid ("PNA") based on a linked N-(2-aminoethyl)glycine backbone to which normal DNA bases have been attached (Egholm et al., 1993, Nature 365:566–67). This PNA obeys specific Watson-Crick base pairing, but with greater free energy of binding and correspondingly higher melting temperatures. Suitable oligomers may be constructed entirely from PNAs or from mixed PNA and DNA and/or RNA oligomers. In fact, PNA:DNA chimeras have increased solubility characteristics, as compared to DNA:DNA or DNA:RNA chimeras of the same sequence. Most notably, PNAs have the unique ability to displace one strand of a DNA double-helix thus making them highly suitable in antisense applications (Uhlmann E., Biol. Chem. 1998 August–September; 379(8–9):1045–52).

In a preferred embodiment, the oligonucleotide comprises at least one modified phosphate backbone selected from the group consisting of a phosphorothioate, a phosphorodithioate, a phosphormidothioate, a phosphoramidate, a phosphordiamidate, a methylphosphonate, an alkyl phosphotriester, and a formacetal or analog thereof.

In another embodiment, the anti-sense oligonucleotide of the invention may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine.

In another embodiment, the anti-sense oligonucleotide comprises at least one modified sugar moiety selected from the group including, but not limited to, arabinose, 2-fluoroarabinose, xylulose, and hexose.

In yet another embodiment, the anti-sense oligonucleotide may be conjugated to another molecule, e.g., a peptide, hybridization triggered cross-linking agent, transport agent, hybridization-triggered cleavage agent, etc.

The anti-sense oligonucleotides of the invention may be synthesized by standard methods known in the art, e.g., by use of an automated DNA synthesizer (such as are commercially available from Biosearch, Applied Biosystems, etc.). As examples, phosphorothioate oligos may be synthesized by the method of Stein et al. (1988, Nucl. Acids Res. 16:3209), methylphosphonate oligos can be prepared by use of controlled pore glass polymer supports (Sarin et al., 1988, Proc. Natl. Acad. Sci. USA 85:7448–7451), etc.

In a specific embodiment, the oligonucleotide comprises catalytic RNA, or a ribozyme (see, e.g., PCT International Publication WO 90/11364, published Oct. 4, 1990; Sarver et al., 1990, Science 247:1222–1225; Hasselhoff, et al., Nature 342:76–79 (1988)). Ribozymes have been used to down-regulate gene expression, and more recently in the down-regulation of plant proteins (seem e.g., PCT International Publication WO 97/10328). In another embodiment, the oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Other Activities

In another embodiment, the polypeptides, polynucleotides encoding these polypeptides, variants, and/or fragments thereof, may be used to inhibit gene expression using co-suppression methodology. The mechanism of co-suppression is not known, though its application to inhibiting plant gene expression has been documented and described (e.g., Seymour, et al., Plant Mol. Biol., 23:1–9, (1993), Brusslan, et al., Plant Cell, 5:667–677, (1993),; Vaucheret, et al., Mol. Gen. Genet, 248:311–317, (1995); and Jorgensen, et al., Plant Mol. Biol., 31:957–973, (1996)). Co-suppression involves creating a consititutively expressed vector construct comprising, for example, a CaMV 35S promoter, the 5' coding region of a first gene (R) for which inhibited expression is desired, in-frame and upstream from, the entire coding region of a second gene (S) for which inhibited expression is desired, and a terminator. Upon positive transformation of plants with this vector (i.e., transgenic plants), no detectable mRNA expression will be detected for either R nor S (see Seymour, supra).

The polypeptide or polynucleotides and/or agonist or antagonists of the present invention may also increase or decrease the differentiation or proliferation of protoplast cells, emyloblast cells, etc.

The polypeptide or polynucleotides and/or agonist or antagonists of the present invention may be useful in modulating programmed cell death in plants, plant cells, and eukaryotic cells and organisms, in general. Such modulation would either be through direct or indirect interaction between a polypeptide or polynucleotides and/or agonist or antagonists of the present invention with the gene or protein critical in modulating programmed cell death in the organism. Specific targets of interaction for program cell death, particularly in a plant, are provided in International Publication Number WO 00/04173 (e.g., poly-ADP-ribose polymerase (PARP) genes, specifically PARP genes of the ZAP class, etc.).

The polypeptide or polynucleotides and/or agonist or antagonists of the present invention may also be used to modulate plant characteristics, such as stem height, pigmentation, stress tolerance, etc. Similarly, polypeptides or polynucleotides and/or agonist or antagonists of the present invention may be used to modulate plant metabolism affecting catabolism, anabolism, processing, utilization, and storage of energy.

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the "5' NT of Clone" and ending with the nucleotide at about the position of the "3' NT of Clone" as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the "5' NT of Start Codon of Clone ORF" and ending with the nucleotide at about the position of the "3' NT of Clone ORF" as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the "5' NT of the First AA of the Signal Peptide" and ending with the nucleotide at about the position of the "3' NT of Clone ORF" as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the "5' NT of Clone ORE" and ending with the nucleotide at about the position of the "3' NT of Clone ORF" as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a cDNA clone identified by a cDNA Clone Identifier in Table 1, which DNA molecule is contained in the material deposited with the American Type Culture Collection and given the ATCC Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a cDNA clone identified by a cDNA Clone Identifier in Table 1, which DNA molecule is contained in the deposit given the ATCC Deposit Number shown in Table 1.

Also preferred is an isolated nucleic acid molecule, wherein said sequence of at least 50 contiguous nucleotides is included in the nucleotide sequence of the complete open reading frame sequence encoded by said cDNA clone.

Also preferred is an isolated nucleic acid molecule comprising a nucleotide sequence which is at least 95% identical to sequence of at least 150 contiguous nucleotides in the nucleotide sequence encoded by said cDNA clone.

A further preferred embodiment is an isolated nucleic acid molecule comprising a nucleotide sequence which is at least 95% identical to sequence of at least 500 contiguous nucleotides in the nucleotide sequence encoded by said cDNA clone.

A further preferred embodiment is an isolated nucleic acid molecule comprising a nucleotide sequence which is at least 95% identical to the complete nucleotide sequence encoded by said cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a cDNA clone identified by a cDNA Clone Identifier in Table 1 and contained in the deposit with the ATCC Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence is determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a cDNA clone identified by a cDNA Clone Identifier in Table 1 and contained in the deposit with the ATCC Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of a nucleotide sequence of SEQ ID NO:X wherein X is any integer as defined in Table 1; and a nucleotide sequence encoded by a cDNA clone identified by a cDNA Clone Identifier in Table 1 and contained in the deposit with the ATCC Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a cDNA clone identified by a cDNA Clone Identifier in Table 1 and contained in the deposit with the ATCC Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the "Total AA of the Open Reading Frame (ORF)" as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a protein encoded by a cDNA clone identified by a cDNA Clone Identifier in Table 1 and contained in the deposit with the ATCC Deposit Number shown for said cDNA clone in Table 1.

Also preferred is a polypeptide wherein said sequence of contiguous amino acids is included in the amino acid sequence of a portion of the protein encoded by a cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 30 contiguous amino acids in the amino acid sequence of the portion of the protein encoded by a cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 100 contiguous amino acids in the amino acid sequence of the protein encoded by a cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to the amino acid sequence of the protein encoded by a cDNA clone identified by a cDNA Clone Identifier in Table 1 and contained in the deposit with the ATCC Deposit Number shown for said cDNA clone in Table 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a cDNA clone identified by a cDNA Clone Identifier in Table 1 and contained in the deposit with the ATCC Deposit Number shown for said cDNA clone in Table 1.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a cDNA clone identified by a cDNA Clone Identifier in Table 1 and contained in the deposit with the ATCC Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a cDNA clone identified by a cDNA Clone Identifier in Table 1 and contained in the deposit with the ATCC Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a cDNA clone identified by a cDNA Clone Identifier in Table 1 and contained in the deposit with the ATCC Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing a pathological condition associated with an organism with abnormal structure or expression of a gene encoding a protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a cDNA clone identified by a cDNA Clone Identifier in Table 1 and contained in the deposit with the ATCC Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of an amino acid sequence of SEQ ID NO:Y wherein Y is any integer as defined in Table 1; and a complete amino acid sequence of a protein encoded by a cDNA clone identified by a cDNA Clone Identifier in Table 1 and contained in the deposit with the ATCC Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a protein encoded by a cDNA clone identified by a cDNA Clone Identifier in Table 1 and contained in the deposit with the ATCC Deposit Number shown for said cDNA clone in Table 1.

Further preferred is a method of making a recombinant vector comprising inserting any of the above isolated nucleic acid molecule(s) into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a protein comprising an amino acid sequence selected from the group consisting of: an amino acid sequence of SEQ ID NO:Y comprising the range depicted in "Total AA of ORF" of SEQ ID NO:Y wherein Y is an integer set forth in Table 1; and an amino acid sequence of a protein encoded by a cDNA clone identified by a cDNA Clone Identifier in Table 1 and contained in the deposit with the ATCC Deposit Number shown for said cDNA clone in Table 1. The isolated polypeptide produced by this method is also preferred.

Also preferred is a method of treatment of an individual in need of an increased level of protein activity, which method comprises administering to such an individual a pharmaceutical composition comprising an amount of an isolated polypeptide, polynucleotide, or antibody of the claimed invention effective to increase the level of said protein activity in said individual.

The above-recited applications have uses in a wide variety of hosts. Such hosts include, but are not limited to, barley, oats, rye, sorghum, pea, sunflower, tobacco, cotton, petunia, tomato, broccoli, lettuce, apple, plum, orange, and lemon, and more preferably rice, maize, conola, wheat, sugerbeet, sugercane, and soybean, in addition to other hosts referenced elsewhere herein.

Having generally described the invention, the same will be more readily understood by reference to the following examples, which are provided by way of illustration and are not intended as limiting.

EXAMPLES

DESCRIPTION OF THE PREFERRED EMBODIMENTS

Example 1

Culturing *Physcomitrella patens*

Plants of the species *Physcomitrella patens* (Hedw.) B.S.G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am J Bot 55, 438–446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores mature.

Culturing was carried out in a climatic chamber at an air temperature of 25° C. and light intensity of 55 umol s$^{-1}$m$^{-2}$ (white light; Philips TL 65W/25 fluorescent tube) and a light/dark change of 16/8 hours. The moss was either modified in liquid culture using Knop medium according to Reski and Abel (1985, Planta 165, 354–358) or cultured on Knop solid medium using 1% oxoid agar (Unipath, Basingstoke, England).

The protonemas used for RNA and DNA isolation were cultured in aerated liquid cultures. The protonemas were comminuted every 9 days and transferred to fresh culture medium.

Example 2

Construction of the cDNA Library from *Physcomitrella patens*

For cDNA library construction first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12 degree C. (2 h), 16 degree C. (1 h) and 22 degree C. (1 h). The reaction was stopped by incubation at 65 degree C. (10 min) and subsequently transferred to ice. Double stranded DNA molecules were blunted by T4 DNA-polymerase (Roche, Mannheim) at 37 degree C. (30 min). Nucleotides were removed by phenol/chloroform extraction and Sephadex G50 spin columns. EcoRI adapters (Pharmacia, Freiburg, Germany) were ligated to the cDNA ends by T4DNA-ligase (Roche, 12 degree C., overnight) and phosphorylated by incubation with polynucleotide kinase (Roche, 37 degree C., 30 min). This mixture was subjected to separation on a low melting agarose gel. DNA molecules larger than 300 basepairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 3

Sequencing and Function Annotation of *Physcomitrella patens* ESTs cDNA libraries as described in Example 4 were used for DNA sequencing according to standard methods, in particular by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands. Plasmid DNA was prepared from overnight grown *Escherichia coli* cultures grown in Luria-Broth (LB) medium containing ampicillin (see Sambrook et al. (1989) (Cold Spring Harbor Laboratory Press: ISBN 0-87969-309-6)) on a Qiagene DNA preparation robot (Qiagen, Hilden) according to the manufacturers protocols. Sequencing primers with the following nucleotide sequences were used:

```
Qiagen1:  5'-CAGGAAACAGCTATGACC-3'    (SEQ ID NO:6)
Qiagen2:  5'-CTAAAGGGAACAAAAGCTG-3'   (SEQ ID NO:7)
Qiagen3:  5'-TGTAAAACGACGGCCAGT-3'    (SEQ ID NO:8)
```

Sequences were processed and annotated using the software package EST-MAX commercially provided by BioMax (Munich, Germany). The program incorporates practically all bioinformatics methods important for functional and structural characterization of protein sequences. For reference see http.//pedant.mips.biochem.mpg.de.

The most important algorithms incorporated in EST-MAX are:

FASTA: Very sensitive protein sequence database searches with estimates of statistical significance; Pearson W. R. (1990) Rapid and sensitive sequence comparison with FASTP and FASTA. Methods Enzymol. 183:63–98.

BLAST: Very sensitive protein sequence database searches with estimates of statistical significance. Altschul S. F., Gish W., Miller W., Myers E. W., and Lipman D. J. Basic local alignment search tool. Journal of Molecular Biology 215:403–10.

PREDATOR: High-accuracy secondary structure prediction from single and multiple sequences. Frishman, D. and Argos, P. (1997) 75% accuracy in protein secondary structure prediction. Proteins, 27:329–335.

CLUSTALW: Multiple sequence alignment. Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673–4680.

TMAP: Transmembrane region prediction from multiply aligned sequences. Persson, B. and Argos, P. (1994) Prediction of transmembrane segments in proteins utilizing multiple sequence alignments. J. Mol. Biol. 237: 182–192.

ALOM2: Transmembrane region prediction from single sequences. Klein, P., Kanehisa, M., and DeLisi, C. Prediction of protein function from sequence properties: A discriminant analysis of a database. Biochim. Biophys. Acta 787:221–226 (1984). Version 2 by Dr. K Nakai.

PROSEARCH: Detection of PROSITE protein sequence patterns. Kolakowski L. F. Jr., Leunissen J. A. M., Smith J. E. (1992) ProSearch: fast searching of protein sequences with regular expression patterns related to protein structure and function. Biotechniques 13, 919–921.

BLIMPS: Similarity searches against a database of ungapped blocks. J. C. Wallace and Henikoff S., (1992)

PATMAT: A searching and extraction program for sequence, pattern and block queries and databases, CABIOS 8:249–254. Written by Bill Alford.

Example 4

Binary Vector Construction

The pNC53 vector was digested with HindIII (Roche) and blunt-end filled with Klenow enzyme and 0.1 mM dNTPs (Roche) according to manufacture's instructions. This fragment was extracted from agarose gel with a QIAquick Gel Extraction Kit (Qiagen) according to manufacture's instructions. The purified fragment was then digested with EcoRI (Roche) according to manufacture's instructions. This fragment was extracted from agarose gel with a QIAquick Gel Extraction Kit (Qiagen) according to manufacture's instructions. The resulting 1.4 kilobase fragment, the gentamycin casstte, included the nos promoter, aacCI gene and the g7 terminator.

The vector pBlueScript was digested with EcoRI and SmaI (Roche) according to manufacture's instructions. The resulting fragment was extracted from agarose gel with a QIAquick Gel Extraction Kit (Qiagen) according to manufacture's instructions. The digested pBlueScript vector and the gentamycin cassette fragments were ligated with T4 DNA Ligase (Roche) according to manufacture's instructions, joining the two respective EcoRI sites and joining the blunt-ended HindIII site with the SmaI site. The recombinant vector (pGMBS) was transformed into Top10 cells (Invitrogen) using standard conditions. Transformed cells were selected for on LB agar containing 50 μg/ml Kanamycin, grown overnight at 37° C. and used to inoculate 3 ml of liquid LB containing 50 μg/ml Kanamycin and grown overnight at 37° C. Plasmid DNA was extracted using the QIAprep Spin Miniprep Kit (Qiagen) following manufacture's instructions. Analyses of subsequent clones and restriction mapping was performed according to standard molecular biology techniques (Sambrook et al. 1989).

Both the pGMBS vector and p1bxSuperGUS vector were digested with XbaI and KpnI (Roche) according to manufacture's instructions, excising the gentamycin casstte from pGMBS and producing the backbone from the p1bxSuperGUS vector. The resulting fragments were extracted from agarose gel with a QIAquick Gel Extraction Kit (Qiagen) according to manufacture's instructions. These two fragments were ligated with T4 DNA ligase (Roche) according to manufactures's instructions. The resulting recombinant vector (pGMSG) was transformed into Top10 cells (Invitrogen) using standard conditions. Transformed cells were selected for on LB agar containing 50 μg/ml Kanamycin, grown overnight at 37° C. and used to inoculate 3 ml of liquid LB containing 50 μg/ml Kanamycin and grown overnight at 37° C. Plasmid DNA was extracted using the QIAprep Spin Miniprep Kit (Qiagen) following manufacture's instructions. Analyses of subsequent clones and restriction mapping was performed according to standard molecular biology techniques (Sambrook et al. 1989).

Example 5

Total RNA Isolation from *Physcomitrella patens*

The total RNA was obtained from wild-type 14 day old *Physcomitrella patens* following the Van Slogteren method (Van Slogteren, C. M. S., Hoge, J. H. C., Hooykaas, P. J. J., and Schilperoort, R. A. 1983. Clonal analysis of heterogenous crown gall tumor tissues induced by wild-types and shooter mutant strains of *Agrobacterium tumefaciens*-expression of T-DNA genes. Plant Mol. Biol. 2: 321–333, 1983) with slight modifications. The plant tissue (200 mg) was frozen with liquid nitrogen and ground to a fine powder with a mortar and pestle. The powder was placed in a microfuge tube and the RNA was extracted with 500 ul of extraction buffer (phenyl:0.1M LiCl, 100 mM Tris-HCl [pH 8.0], 10 mM EDTA, 1% SDS (w/v) [1:1] preheated to 90° C. The mixture was heated further for 1 mm at 90° C. and then vortexed for 5 mins. Proteins were extracted by adding 250 ul of chloroform:isoamyl alcohol (24:1) and the mixture was vortexed for 5 mins and centrifuged for 15 mins at 13,000 rpm in an Eppendorf centrifuge 5414 at 4° C. The aqueous layer was removed and the protein extraction was repeated twice more. One vol of 4 mM LiCl was added and the RNA was allowed to precipitate overnight at 4° C. To collect the RNA, the mixture was centrifuged for 15 min at 4° C. at 13,000 rpm in an Eppendorf centrifuge 5414. The pellet was resuspended in 250 ul sterile, deionized water. To precipitate the RNA, 0.1 vols of 3M sodium acetate pH 5.2) and 2 vols 100% ethanol were added. An aliquote was taken and centrifuged for 20 mins at 4° C. at 13,000 rpm in an Eppendorf centrifuge 5414. The pellet was washed with 70% ethanol to remove salts from the pellet and dried using a speed vac. The pellet was resuspended in 25 ul DEPC H2O and analyzed for integrity via electrophoresis. The RNA was stored at −70° degree C.

Example 6

Construction of cDNA Library of *Phycomitrella patens*

To isolate the full-length clones encoding $Na^+/H^+$ Antiporter from *Physcomitrella patens* a cDNA library was created with SMART RACE cDNA Amplification kit (Clontech Laboratories) following manufacture's instructions. Total RNA created as described in Example 5 was used as the template.

Example 7

Obtaining the Full Length Clone of the Vacuole-type $Na^+/H^+$ Antiporter from *Physcomitrella patens*

The *Physcomitrella patens* full-length and partial clones (EST#156 and EST#610) for PpNHX1 (SEQ ID NO: 1) and PpNBX2 (SEQ ID NO: 3) were identified in the *Physcomitrella patens* EST sequencing program using the program EST-MAX through BLAST analysis. These particular clone were chosen for further analyses since they encoded for $Na^+/H^+$ antiporter. For PpNHX1A full-length sequence corresponding to EST #156 was obtained by performing polymerase chain reaction (PCR) with a gene-specific EST as the template DNA. The synthetic oligonucleotide primers (MWG-Biotech) for the reaction were: 156F: 5'-CTGC-CCGGGTACCGGAAGGTTGAAGATGGCGAC-3' (SEQ ID NO:9) and 156R: 5'-GACGAGCTCTAGACACTAACT-TGATTCAACTGTG-3' (SEQ ID NO:10). The primers designed contained a SmaI and a KpnI site in the 5' region and a SacI and a XbaI site in the 3' region for cloning purposes. The conditions for the reaction were standard conditions with PWO DNA polymerase. (Roche). PCR was performed according to standard conditions and to manufacture's protocols (Sambrook et al. 1989, Biometra T3 Thermocycler). The parameters for the reaction were: five minutes at 94° C. followed by five cycles of one minute at 94° C., one minute at 50° C. and 1.5 minutes at 72° C. This was followed by twentyfive cycles of one minute at 94° C., one minute at 65° C. and 1.5 minutes at 72° C. These parameters generated a fragment 1.7 kilobases long.

The fragment was extracted from agarose gel with a QIAquick Gel Extraction Kit (Qiagen) and ligated into the TOPO pCR 2.1 vector (Invitrogen) following manufacture's instructions. Recombinant vectors were transformed into Top10 cells (Invitrogen) using standard conditions (Sambrook et al. 1989). Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside) grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacture's instructions. Analyses of subsqunt clones and restriction mapping was performed according to standard molecular biology techniques (Sambrook et al. 1989).

For PpNHX2

To isolate full-length clone encoding for PpNHX2 from *Physcomitrella patens*, cDNA libraries was used as a template for RACE.

5' and 3' RACE Pr tocol

The EST sequence (EST#610) identified from the database search as described in Example 3 was used to design oligos (CGTTTGCGCATGCCCC TGGTCGCTT SEQ ID NO: 15; CAGGACGAAGGAAACACCGACACCT SEQ ID NO: 16) for RACE. The extended sequences for the gene were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions.

The sequences obtained from the RACE reactions corresponded to full-length coding regions of PpNFX2 and was used to design oligos for full-length cloning of the respective genes (see below full-length amplification).

Full-length Amplification

Full-length clones corresponding PpNBX2 (SEQ ID NO: 4) was obtained by performing polymerase chain reaction (PCR) with gene-specific primers (610F: CTGCCCGGG-TACCATTGGCACCAGCAAGATGGCGGACGCT SEQ ID NO: 17 610R: GCGTCTAGAC CCGGGTCATA TACACGCGGT GGTCAGGAG SEQ ID NO: 18).

The fragment of the fill-length clone was isolated and sub-cloned into the TOPO pCR 2.1 vector (Invitrogen) by following the same procedure for PpNHX1 except for following several steps. For cloning purposes the primers designed contained a SmaI and a KpnI site in the 5' region and a SmaI and a xbaI site in the 3' region. The parameters for the PCR reaction were the same as that for PpNHX1 except for the extension time for 3 minute at 72° C. This extension time allowed to amplify a fragment 2.6 kb.

Example 8

Subcloning the Na$^+$/H$^+$ Antiporter from *Physcomitrella patens* into pGMSG.

For PpNHX1

The fragment containing the Na$^+$/H$^+$ antiporter was excised from the recombinant TOPO pCR vector by digestion with SacI and SmaI (Roche) according to manufacture's instructions. The subsequent fragment was excised from agarose gel with a QIAquick Gel Extraction Kit (Qiagen) according to manufacture's instructions. The target binary vector was also cleaved with SacI and SmaI (Roche) and dephosphorylated with shrimp alkaline phosphatase (Roche) according to manufacture's instructions. The resulting fragment was extracted from agarose gel with a QIAquick Gel Extraction Kit (Qiagen). The binary vector and Na$^+$/H$^+$ antiporter fragments were ligated together with Rapid DNA Ligation Kit (Roche), joining the respective SacI sites and SmaI sites.

Recombinant vectors were transformed into Top10 cells (vitrogen) using standard conditions (Sambrook et al. 1989). Transformed cells were selected for on LB agar containing 50 µg/ml Kanamycin (Roche). Plasmid DNA was extracted using the QIAprep Spin Miniprep Kit (Qiagen) following manufacture's instructions. Analyses of subsequent clones and restriction mapping was performed according to standard molecular biology techniques (Sambrook et al. 1989). The recombinant vector was transformed into *Agrobacterium tumefaciens* according to standard conditions (Hoefgen and Wilmitzer, 1990 Biochemical and genetic analysis of different patatin isoforms expressed in various organs of potato (solanum tuberosum); Plant Science 66,221–230). The resultant vector is named as pBPSNVT001.

For PpNBX2

The full-length fragment of the Na$^+$/H$^+$ antiporter was subcloned into the binary vector by following the same procedure for PpNHX1 except for the following steps. For the excision of the fragment from the TOPO pCR vector KpnI and SmaI (Roche) were used. The resultant fragment was blunt ended and ligated into the binary vector that was digested by SmaI (Roche) and dephosphorylated with shrimp alkaline phosphatase (Roche) according to manufacture's instructions. The resultant vector is named as pBPSNVT003.

Example 9

Transformation of *Agrobacterium tumefaciens*

The recombinant vectors were transformed into *Agrobacterium tumefaciens* C58C1 and PMP90 according to standard conditions (Hoefgen and Willmitzer, 1990).

Example 10

Subcloning the Na$^+$/H$^+$ antip rter from *Physcomitrella patens* into pYES.

The fragments containing the Na$^+$/H$^+$ antiporter (PpNHX1 and PpNHX2) was excised respectively from the recombinant TOPO pCR vector by digestion with KpnI and XbaI (Roche) according to manufacture's instructions. The subsequent fragment was excised from agarose gel with a QIAquick Gel Extraction Kit (Qiagen) according to manufacture's instructions. The target binary vector was also cleaved with KpnI and XbaI (Roche) and dephosphorylated with shrimp alkaline phosphatase (Roche) according to manufacture's instructions. The vector and Na$^+$/H$^+$ antiporter fragments were ligated together with Rapid DNA Ligation Kit (Roche) and transformed into Top10 Cells (Invitrogen) according to standard protocols (Sambrook et al. 1989). Transformed cells were selected for on LB agar containing 50 µg/ml Kanamycin. Plasmid DNA was extracted using the QIAprep Spin Miniprep Kit (Qiagen) following manufacture's instructions. Analyses of subsequent clones and restriction mapping was performed according to standard molecular biology techniques (Sambrook et al. 1989).

Example 11

In vivo Complementation of the NHX1 Saccharomyces cerevisiae Mutant

The recombinant expression pYES2 vector (Invitrogen) containing the Na$^+$/H$^+$ antiporters, PpNHX1 and PpNHX2, respectively in the sense orientation under the *Saccharomyces cerevisiae* GAL1 promoter was transformed into the yeast mutant BY4741 (MATa his3::D1 leu2::D0 lys2D0 ura3::D0) following manufacture's instructions. The transformed cells were selected for on Complete Supplement Mixture (CSM) minus Uracil 0.8% agar (Bio 101, Inc.) grown at 30° C. for two days. The transformed colonies were selected to plate on 1) CSM plus Uracil 0.8% agar plates, 2) CSM minus Uracil 0.8% agar plates, 3) CSM minus Uracil 0.8% agar plates supplemented with 2% galactose for induction of the expression of the antiporter and 4) CSM minus Uracil 0.8% agar plates supplemented with 2% galactose for induction of the expression of the antiporter and 0.5M NaCl. The plates were incubated at 30° C. for two days.

Example 12

Transformation of *Arabidopsis thaliana*

*Arabidopsis thaliana* ecotype C24 were grown and transformed according to standard conditions (Bechtold 1993 (Bechtold, N., Ellis, J., Pelletier, G. 1993. In planta *Agrobacterium* mediated gene transfer by infiltration of *Arabidopsis thaliana* plants C.R Acad.Sci.Paris. 316:1194–1199); Bent et al. 1994 (Bent, A., Kunkel, B. N., Dahlbeck, D., Brown, K. L., Schmidt, R., Giraudat, J., Leung, J., and Staskawicz, B. J. 1994; PPCS2 of *Arabidopsis thaliana*: A leucin-rich repeat class of plant disease resistant genes; Science 265:1856–1860).

Example 13

Screening of Transformed *Arabidopsis* Plants

*Arabidopsis* T1 and T2 seeds were sterilized according to standard protocols (Xiong et al., Plant Molecular Biology 17, 150–170 (1999)). Seeds were plated on ½ MS 0.6% agar supplemented with 1–3% sucrose and 50–150 μg/l gentamycin. Seeds on plates were vernalized for two days at 4° C. The seeds were germinated in a climatic chamber at an air temperature of 22° C. and light intensity of 55 umol s$^{-1}$m$^{-2}$ (white light; Philips TL 65W/25 fluorescent tube) and a light/dark change of 16/8 hours. Transformed Arabidopsis seedlings were selected after 7–14 and transferred to ½ MS 0.6% agar plates supplemented with 1% sucrose and allowed to recover for 1–5 days. The transgenic plants are screened for their improved salt tolerance according to the screening method described in example 17 demonstrating that transgene expression confers salt tolerance.

Example 14

Detection of the Na$^+$/H$^+$ Antiporter Transgene in the *Arabidopsis* Transgenic Lines To check for the presence of the PpNHX1 and PpNBX2 transgene in Arabidopsis T1 and T2 transgenic lines, PCR was performed on genomic DNA which contaminates the RNA samples taken as described in Example 5 below. 2.5 μl of RNA sample was used in a 50 μl PCR reaction using Taq DNA polymerase (Roche Molecular Biochemicals) according to the manufacturer's instructions. The gene specific primers (for PpNHX1:156F: 5'-CTGCCCGGGTACCG-GAAGGTTGAAGATGGCGAC-30' SEQ ID NO: 19 and 156R. 5'-GACGAGCTCTAGACACTAACTTGATTCAAC TGTG-3. SEQ ID NO: 20; for PpNHX2: 610F: CTGC-CCGGGTACCATTGGCACCAGCAAGATGGCGGACGC T SEQ ID NO: 21 610R: GCGTCTAGAC CCGGGTCATA TACACGCGGT GGTCAGGAG SEQ ID NO: 22) were used for the PCR. Binary vector plasmid with PpNHX1 and PpNHX2 gene cloned in was used as positive control, and the wild type C24 genomic DNA was used as negative control in the PCR reactions. 10 μl PCR reaction was analyzed on 0.8% agarose—ethidium bromide gel.

The transgene was successfully amplified from the T1 and T2 transgenic lines, but not from the wild-type plants. This result indicated that the T1 and T2 transgenic plants contain at least one copy of the PpNHX1 and PpNHX2 transgene. There was no indication of existence of the corresponding gene or homolog of the PpPNHX1 and PpNHX2 that could be amplified in this method in the wild-type plants.

Example 15

Detection of the Na$^+$/H$^+$ Antiproter Transgene mRNA in Transgenic *Arabidopsis* Lines Transgene expression was detected using RT-PCR Total RNA was isolated from T1 and T2 plants using a procedure adapted from (Verwoerd et al. 1989. NAR 17:2362). Leaf samples (50–100 mg) were collected and ground to a fine powder in liquid nitrogen. Ground tissue was resuspended in 500 μl of a 80° C., 1:1 mixture, of phenol to extraction buffer (100 mM LiCl, 100 mM Tris pH 8, 10 mM EDTA, 1% SDS), followed by brief vortexing to mix. After the addition of 250 μl of chloroform each sample was vortexed briefly. Samples were then centrifuged for 5 minutes at 12,000×g. The upper aqueous phase was removed to a fresh eppendorf tube. RNA was precipitated by adding ¹/₁₀$^{th}$ volume 3M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air dried. RNA sample pellets were resuspended in 10 μl DEPC treated water. To remove contaminating DNA from the samples, each was treated with RNase-free DNase (Roche) according to the manufacturer's recommendations. cDNA was synthesized from total RNA using the Superscript First-Strand Synthesis System for RT-PCR (Gibco-BRL) following manufacturer's recommendations. PCR amplification of a gene-specific fragment from the synthesized cDNA was performed using Taq DNA polymerase (Roche) and gene-specific primers (for PpNHX1:156F: 5'-CTGCCCGGGTACCGGAAGGT-TGAAGATGGCGAC-3' SEQ ID NO: 19 and 156R: 5'-GA CGAGCTCTAGACACTAACTTGATTCAACTGTG-3. SEQ ID NO: 20; for PpNHX2: 5'-CGTTTGCGCATGC-CCCTGGTCGCTT-3' SEQ ID NO: 21, 610R: GCGTCTA-GAC CCGGGTCATA TACACGCGGT GGTCAGGAG SEQ ID NO. 22) in the following reaction: 1×PCR buffer, 1.5 mM MgCl$_2$, 0.2 μM each primer, 0.2 μM dNTPs, 1 unit polymerase, 5 μl cDNA from synthesis reaction. Amplification was performed under the following conditions: Denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad).

Expression of the transgenes was detected in the T1 and T2 transgenic lines. These results indicated that the transgenes are expressed in the transgenic lines and strongly suggested that their gene product improved plant stress tolerance in the transgenic lines. In agreement with the previous statement, no expression of identical or very similar endogenous genes could be detected by this method. These results are in agreement with the data from Example 14.

Example 16

Transformation of Soybean

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air dried to a moisture content less than 20% (fresh weight) in a sealed Petri dish until further use. *Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at RT, and resuspended in MS (Murashige and Skoog, 1962) medium supplemented with 100 μM acetosyringone. Bacteria cultures are incubated in this pre-induction medium for 2 hours at RT before use. The axis of soybean zygotic seed embryos at approximately 15% moisture content are imbibed for 2 hours at RT with the pre-induced *Agrobacterium* suspension culture. The embryos are removed from the imbibition culture and are transferred to Petri dishes containing solid MS medium supplemented with 2% sucrose and incubated for 2 days, in the dark at RT. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the agrobacteria. The liquid medium is used to moisten the sterile filter paper. The embryos are incubated during 4 weeks at 25° C., under 150 $\mu molm^{-2}sec^{-1}$ and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 150 $\mu mol\ m^{-2}sec^{-1}$ light intensity and 12 hours photoperiod for about 80 days.

Example 17

Transformation of Canola

The method described in example 14 of plant transformation is also applicable to Brassica and other crops. Seeds of canola are surface sterilized with 70% ethanol for 4 minutes at room temperature with continuous shaking, followed by 20% (v/v) Clorox supplemented with 0.05% (v/v) Tween for 20 minutes, at RT with continuous shaking. Then, the seeds are rinsed 4 times with distilled water and placed on moistened sterile filter paper in a Petri dish at room temperature for 18 hours. Then the seed coats are removed and the seeds are air dried overnight in a half-open sterile Petri dish. During this period the seeds loses approx. 85% of its water content The seeds are then stored at room temperature in a sealed Petri dish until further use. DNA constructs and embryo imbibition are as described in example 14. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

Example 18

Transformation of Corn

Transformation of maize (*Zea Mays* L.) is performed with the method described by Ishida et al. 1996. Nature Biotch 14745–50), Immature embryos are cocultivated with *Agrobacterium tumefaciens* that carry "super binary" vectors, and transgenic plants are recovered through organogenesis. This procedure provides a transformation efficiency between 2.5% and 20%.

The imbibition of dry embryos with a culture of *Agrobacterium* is also applicable to maize embryo axes. The experimental protocol is the same as described in example 16 but using maize seeds as the source of embryos.

Example 19

Salt Tolerance Screening

Salt Test on MS Plate

Seedlings were transferred to filter paper soaked in ½ MS and placed on ½ MS 0.6% agar supplemented with 2 ug/ml benomyl the night before the stress screening. For the stress screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 mM NaCl, in a petri dish. After 10 hours, the seedlings were moved to petri dishes containing ½ MS 0.6% agar supplemented with 2 ug/ml benomyl. The seedlings were scored after 5 days.

Soil Test for Salt Tolerence

Seeds of plants to be tested are sterilized (100% bleach, 0.1% TritonX for five minutes two times and rinsed five times with ddH2O). Seeds are plated on nonselection media (½ MS, 0.6% phytagar, 0.5 g/L MES, 1% sucrose, 2 ug/ml benamyl). Seeds are allowed to germinate for approximately ten days. At the 4–5 leaf stage, transgenic plants were potted into 5.5 cm diameter pots filled with loosely packed soil (Metromix 360, Scotts) wetted with 1 g/L 20-20-20 fertilizer (Peters Professional, Scotts).

The plants are allowed to grow (22° C., continuous light) for approx. seven days, watering as needed. When the plants are just about to bolt, the water is removed from the tray and the assay is started. To begin the assay, three liters of 100 mM NaCl and ⅛ MS was added to the tray under the pots. To the tray containing the control plants, three liters of ⅛ MS was added. After 10 days, the NaCl treated and the control plants were given water. Ten days later, the plants were photographed.

The T1 PpNHX1 and PpNHX2 transgenic lines were more tolerant than the wild-type after salt stress treatment. On the other hand, the growth of wild-type plants was severely inhibited under the same condition. This result clearly indicates that the transgenic lines over-expressing the PpNHX1 and PpNHX2 gene acquired salt stress tolerance. The results should be better when a homozygous strong expresser will be found.

Example 20

Drought Tolerance Screening

T1 and T2 seedlings were transferred to dry, sterile filter paper in a petri dish and allowed to desiccate for two hours at 80% RH (relative humidity) in a Sanyo Growth Cabinet MLR-350H, micromols$^{-1m2}$ (white light; Philips TL 65W/25 fluorescent tube). The RH was then decreased to 60% and the seedlings were desiccated further for eight hours. Seedlings were then removed and placed on ½ MS 0.6% agar plates supplemented with 2 ug/ml benomyl and scored after five days.

The transgenic plants are screened for their improved drought tolerance demonstrating that transgene expression confers drought tolerance.

Example 21

Freezing Tolerance Screening

Seedlings were moved to petri dishes containing ½ MS 0.6% agar supplemented with 2% sucrose and 2 ug/ml benomyl. After four days, the seedlings were incubated at +4° C. for 1 hour and then covered with shaved ice. The seedlings were then placed in an Environmental Specialist ES2000 Environmental Chamber and incubated for 3.5 hours beginning at −1.0° C. decreasing −1° C. hour. The seedlings were then incubated at −5.0° C. for 24 hours and then allowed to thaw at +5° C. for 12 hours. The water was poured off and the seedlings were scored after 5 days.

The transgenic plants are screened for their improved cold tolerance demonstrating that transgene expression confers cold tolerance.

Example 22

Engineering Salt-tolerant *Arabidopsis* Plants by Overexpression of Na$^+$/H$^+$ Antiporters The construct pBPSNVT001 and pBPSNVT003 were used to transform Arabidopsis as described below.

Transgenic plants overexpressing the Na$^+$/H$^+$ antiporters were obtained and screened as described in the examples 12 and 13, respectively. The transgenic plants are screened for their improved salt tolerance according to the screening method described in example 19 demonstrating that transgene expression confers salt tolerance.

Example 23

Engineering Salt-tyolerant Rapeseed Plants by Overexpression of Na$^+$/H$^+$ Antiporters The construct pBPSNVT001 and pBPSNVT003 were used to transform rapeseed as described below. Transgenic plants overexpressing the Na$^+$/H$^+$ antiporters were obtained and screened as described in the example 17. The transgenic plants are screened for their improved salt tolerance according to the screening method described in example 19 demonstrating that transgene expression confers salt tolerance.

Example 24

Engineering Salt-tolerant Soybean Plants by Overexpression of Na$^+$/H$^+$ Antiporters The construct pBPSNVT001 and pBPSNVT003 were used to transform soybean as described below.

Transgenic plants overexpressing the Na$^+$/H$^+$ antiporters were obtained and screened as described in the example 16. The transgenic plants are screened for their improved salt tolerance according to the screening method described in example 19 demonstrating that transgene expression confers salt tolerance.

Example 25

Engineering Salt-tolerant Corn Plants by Overexpression of Na$^+$/H$^+$ Antiporters Transgenic plants overexpressing the Na$^+$/H$^+$ antiporters were obtained and screened as described in the example 18. The transgenic plants are screened for their improved salt tolerance according to the screening method described in example 19 demonstrating that transgene expression confers salt tolerance.

Example 26

Engineering Stress-tolerant Wheat Plants Plants by Over-Expressing the Na$^+$/H$^+$ Antiporters The construct pBPSNVT001 and pBPSNVT003 were used to transform wheat as described below.

Transformation of wheat is performed with the method described by Ishida et al. 1996. Nature Biotch 14745–50), Immature embryos are cocultivated with *Agrobacterium tumefaciens* that carry "super binary" vectors, and transgenic plants are recovered through organogenesis. This procedure provides a transformation efficiency between 2.5% and 20%.

The transgenic plants are screened for their improved salt tolerance according to the screening method described in Example 19 demonstrating that transgene expression confers stress tolerance.

Example 27

Isolation of a Specific Clone from the Deposited Sample

The deposited material in the sample assigned the ATCC Deposit Number cited in Table 1 for any given cDNA clone also may contain one or more additional plasmids, each comprising a cDNA clone different from that given clone.

Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 1–10 plasmid DNAs, each containing a different cDNA clone and/or partial cDNA clone; but such a deposit sample may include plasmids for more or less than 2 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30–40 nucleotides is synthesized using an Applied Biosystems DNA synthesizer according to the sequence reported. The oligonucleotide is labeled, for instance, with 32P-(-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit, (1989), Cold Spring Harbor Laboratory Press, pages 1.93 to 1.104), or other techniques known to those of skill in the art Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5–5 mM $MgCl_2$, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding and/or coding portions of a gene which may not be present in the deposited clone. These methods include but are not limited to, filter probing, clone enrichment using specific probes, and protocols similar or identical to 5' and 3' "RACE" protocols that are well known in the art. For instance, a method similar to 5' RACE is available for generating the missing 5' end of a desired full-length transcript. (Fromont-Racine et al., Nucleic Acids Res. 21(7): 1683–1684 (1993)).

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full-length gene.

This above method starts with total RNA isolated from the desired source, although poly-A+ RNA can be used. The RNA preparation can then be treated with phosphatase if necessary to eliminate 5' phosphate groups on degraded or damaged RNA that may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene. Moreover, it may be advantageous to optimize the RACE prototol to increase the probability of isolating additional 5' or 3' coding or non-coding sequences. Various methods of optimizing a RACE protocol are known in the art, though a detailed description summarizing these methods can be found in B. C. Schaefer, Anal. Biochem., 227:255–273, (1995).

Example 28

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with p32 using the rediprimetm DNA labeling system (Amersham Life Scinece), according to manufacturer's instructions. After labeling, the probe is purified using CHROMA SPIN0-100 column (Clontech Laboratories, Inc.) according to manufacturer's protocol number PT1200-1. The purified labeled probe is then used to examine various tissues for mRNA expression.

Tissue Northern blots containing the bound mRNA of various tissues are examined with the labeled probe using ExpressHybtm hybridization solution (Clonetech according to manufacturers protocol number PT1190-1. Northern blots can be produced using various protocols well known in the art (e.g., Sambrook et al). Following hybridization and washing, the blots are mounted and exposed to film at −70C. overnight and the films developed according to standard procedures.

Example 29

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Plant DNA is used as template in addition to a somatic cell hybrid panel containing individual chromosomes or chromosome fragments (Bios, Inc). The reactions are analyzed on either 8% polyacrylamide gels or 3.5% agarose gels. Chromosome mapping is determined by the presence of an approximately 100 bp PCR fragment in the particular somatic cell hybrid.

Example 30

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, that expresses the lacI repressor and also confers kanamycin resistance (Kan$^r$). Transformants are identified by their ability to grow on LB plates and ampicillin/kanamycin resistant colonies are selected Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.600) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 34 hours at 4 degree C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4 degree C. or frozen at −80 degree C.

Example 31

Purification of a Polypeptide from an Inclusion Body

The following alternative method can be used to purify a polypeptide expressed in E coli when it is present in the form of inclusion bodies. Unless otherwise specified, all of the following steps are conducted at 4–10 degree C.

Upon completion of the production phase of the E. coli fermentation, the cell culture is cooled to 4–10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide art then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A280 monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 32

Cloning and Expression of a Polypeptide in a Baculovirus Expression System

In this example, the plasmid shuttle vector pAc373 is used to insert a polynucleotide into a baculovirus to express a polypeptide. A typical baculovirus expression vector contains the strong polyhedrin promoter of the Autographa californica nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation For easy selection of recombinant virus, the plasmid contains the beta-galactosidase gene from E. coli under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described in Example 1. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. E. coli HB101 or other suitable E. coli hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized bacuolvirus DNA ("BaculoGoldtm baculovirus DNA", Pharmingen, San Diego, Calif.), using the lipofection method described by Felgner et al., Proc. Natl. Acad. Sci. USA 84:7413–7417 (1987). One ug of BaculoGoldtm virus DNA and 5 ug of the plasmid are mixed in a sterile well of a microtiter plate containing 50 ul of serum-free Grace's medium (Life Technologoes Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 33

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTR5) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in Example 1. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HBO101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transformation. Five µg of an expression plasmid is cotransformed with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM. Expression of the desired gene product is analyzed, for instance, by SDS-PAGE and Western blot or by reversed phase HPLC analysis.

In addition to the method provided above, other methods of expressing polypeptides, preferably polypeptides of the present invention are known in the art. For example, U.S. Pat. No. 6,066,781 (which is hereby incorporated by reference herein in its entirety) describes a chimeric gene consisting of the encoding polynucleotides for the N-terminal moiety corresponding to a portion of the rice alpha-amylase signal sequence peptide (MESSLCLLLLVVLCSLTCNS-GQA SEQ ID NO:33 operatively linked, to the encoding polynucleotide sequence of the protein of interest—in this case, a polypeptide of the present invention. This signal sequence peptide may be operatively substituted for the native signal sequence of a polypeptide of the present invention as a heterologous signal sequence. Such a method of producing mature forms of the inventive polypeptides is encompassed by the present invention and may be used either alone or in conjunction with other methods known in the art and/or disclosed herein.

Moreover, enhanced protein production of recombinant proteins in higher plants has recently been obtained by N-terminal fusion of a ubiquitin or a cucumber mosaic virus coat protein peptide (see International Publication No. WO 00/36129). Such methods may be applied to increase the expression of a polypeptide of the present invention in a suitable plant host.

Example 34

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example described herein; see also EP A 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein.

Alternatively, if the naturally occurring signal sequence is not used, the vector can be modified to include a heterologous signal sequence. (See, e.g., WO 96/34891 and/or U.S. Pat. No. 6,066,781, supra.)

Human IgG Fc region:

(SEQ ID NO:11)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGAGTGCGACGGCCGCGACTCTAGAGGAT

Example 35

Production of an Antibody from a Polypeptide

The antibodies of the present invention can be prepared by a variety of methods. (See, Current Protocols, Chapter 2.) As one example of such methods, cells expressing a polypeptide of the present invention are administered to an animal to induce the production of sera containing polyclonal antibodies. In a preferred method, a preparation of the protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Moreover, in a more preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

Example 36

Antibody Mediated Down-Regulation of Plant Proteins

The process of genetically modifying a plant to modulate specific characteristics, to introduce novel traits, or to inhibit endogenous traits represents a significant area of research in the agricultural field. Recently, a new method of modulating endogenous gene expression using antibodies has been elucited (see, International Publication Number WO 00/05391, which is hereby incorporated in its entirety herein). In this example, the researchers were able to achieve 40–70% inhibition of an endogenous plant protein through the use of a single-chain antibody construct directed towards the plant protein.

The method is directed towards the production of monoclonal antibodies, specifically, single chain antibodies, specific to endogenous transit peptides in a plant in an effort to decrease steady state levels of such transit peptides within the plant. The method is comprised of the following steps: I) generating monoclonal antibodies to a specific plant, II) cloning the gene for said monoclonal antibody, III) creating an expression vector comprising a fusion of the heavy-chain and light chain gene sequences of said monoclonal antibody gene downstream of the p67 leader peptide, and under the control of a consititutive plant promotor, IV) optimizing the codons of said heavy-chain and light chain fusion vector for efficient expression of the gene encoded thereof in a plant, and V), transforming a plant with said heavy-chain and light chain fusion expression vector.

The skilled artisan would appreciate the methods described therein (WO 00/05391), and would have the ability to apply such methods to inhibiting the steady-state expression levels of any of the polypeptides of the present invention, including variants, and fragments, thereof. The skilled artisan would appreciate that any leader peptide (i.e., signal sequence) from a plant protein could be used in creating the heavy-chain and light chain fusion vector. The skilled artisan would also appreciate that different plant species may have different codon usage requirements, and thus, the decision to optimize the codons of the heavy-chain and light chain fusion vector would be affected according to the codons required for that particular plant species.

The method could not only be applied to transit peptides, but also to secreted proteins, membrane proteins, receptors, and ligands. The method could also be applied in combination with other antibody production methods in plants. For example, antibodies directed towards polypeptides of the present invention may inhibit specific traits in a plant which could increase the plants defense mechanisms to pathogens. Thus, where such an antibody was expressed, another antibody could be expressed in combination with the first, to inhibiting the pathogenicity of a plant pathogen by directing the expression of antibodies directed towards pathogenic proteins (e.g., those proteins critical to the initiating events of infection, such as the BUF1 gene from *M.grisea*, stage two juvenile salivary gland proteins which include, svp30, scp31a, scp31b, scp32, scp32, sep39, and scp49 from *G.rostochiensis* (WO 96/22372), etc.). Such a combination would also be of value where the second "anti-pathogenic" antibody is an antibody directed towards a pathogen and fused to a toxic protein wherein such a toxin could be chitinase, glucanase, lysozyme, BT, or colicin F, for example (see WO 96/09398), etc.).

As described elsewhere herein, the method could also be used as a means of inhibiting allergic reactions to plant antigens in humans, mammals, animals, etc., by directing the production of a single chain antibody construct specific towards said plant antigen in the plant (via transgenic methodology). In the latter example, the plant would not be limited to edible plants, as inhibiting the production of such a plant antigen would provide benefit to a human by removing the antigen from the humans environment, for example, irrespective of whether the plant was ingested.

Of particular interest to this example, is the fact that secretion of functional antibody through the plasma membrane of plant cells has been reported for protoplasts isolated from transgenic plants and for callus cells adapted to suspension culture (Hein et al., Biotechnol. Prog. 7:455–561, 1991). However, the levels of secreted antibody detected in both culture systems were extremely low. In other studies, cultured tobacco cells were transformed with a gene encoding a synthetic antibody derivative expressed as a single chain consisting of both the heavy- and light-chain variable domains of the intact immunoglobulin joined together by a flexible peptide linker (Pluckthun, Immunol. Rev. 130:151–188, 1991; and Bird et al., Science 242:423–426, 1988). This synthetic single-chain antibody retained the full antigen-binding potential of the intact immunoglobulin but accumulated in the extracellular apoplastic space of the transformed cells (Firek et al., Plant Molecular Biology 23:861–870, 1993), indicating that the antibody was being transported through the plasma membrane but not through the cell wall to the external environment. Moreover, recent studies have shown that increased antibody production in a plant, and heterologous protein expression, in general, could be increased by including in the plant culture medium a protein stabilizing agent (e.g., polyvinylpyrrolidone), see U.S. Pat. No. 6,020,169, which is hereby incorporated by reference in its entirety herein.

Example 37

Transformation of Dicotyledons

The polynucleotides of the present invention, including the polynucleotides encoding the polypeptides of the present invention, in addition to the polynucleotides encoding antibodies directed against the polypeptides of the present invention may be used to transform monocotyledons in an effort to confer specific traits into the plant. Such polynucleotides may be either the full-length polynucleotide, fragments, the complementary strand, or variants thereof, and may be either by themselves or operably fused to heterologous polynucleotides as described in more detail elsewhere herein.

Transformation techniques for dicotyledons are well known in the art and include Agrobacterium-based techniques and techniques which do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowsli et al., EMBO J. 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. The many crop species which are routinely transformable by *Agrobacterium* include tobacco, tomato, sunflower, cotton, oilseed rape, potato, soybean, alfalfa and poplar (EP 0 317 511 (cotton), EP 0 249 432 (tomato, to Calgene), WO 87/07299 (Brassica, to Calgene), U.S. Pat. No. 4,795,855 (poplar)). *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen & Willmitzer, Nucl. Acids Res. 16: 9877(1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid.T-DNA borders.

Other methods for the transformation of dicotyledons are known in the art. Thus, this example should be not construed as limiting the scope of the invention to only those examples illustrated above or elsewhere herein.

Example 38

Transformation of Monocotyledons

The polynucleotides of the present invention, including the polynucleotides encoding the polypeptides of the present invention, in addition to the polynucleotides encoding antibodies directed against the polypeptides of the present invention may be used to transform monocotyledons in an effort to confer specific traits into the plant Such polynucleotides may be either the full-length polynucleotide, fragments, the complementary strand, or variants thereof, and may be either by themselves or operably fused to heterologous polynucleotides as described in more detail elsewhere herein.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435 (to Ciba-Geigy), EP 0 392 225 (to Ciba-Geigy) and WO 93/07278 (to Ciba-Geigy) describe techniques for the preparation of callus and protoplasts from an elite inbred line of maize, transformation of protoplasts using PEG or electroporation, and the regeneration of maize plants from transformed protoplasts. Gordon-Kamm et al., Plant Cell 2: 603–618 (1990)) and Fromm et al., Biotechnology 8: 833–839 (1990)) have published techniques for transformation of A188-derived maize line using particle bombardment Furthermore, application WO 93/07278 (to Ciba-Geigy) and Koziel et al., Biotechnology 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al., Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 9: 957–962 (1991)).

Patent Application EP 0 332 581 (to Ciba-Geigy) describes techniques for the generation, transformation and regeneration of Pooideae protoplasts. These techniques allow the transformation of Dactylis and wheat Furthermore, wheat transformation was been described by Vasil et al., Biotechnology 10: 667–674 (1992)) using particle bombardment into cells of type C long-term regenerable callus, and also by Vasil et al., Biotechnology 11: 1553–1558 (1993)) and Weeks et al., Plant Physiol. 102: 1077–1084 (1993) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashige & Skoog, Physiologia Plantarum 15: 473–497 (1962)) and 3 mg/l 2,4-D for induction of somatic embryos which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene caring plasmid (such as pCIB3064 or pSG35) is precipitated onto micrometer size gold particles using standard procedures. Each plate of embryos is shot with the DuPont Biolistics, helium device using a burst pressure of .about. 1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contained half-strength MS, 2% sucrose, and the same concentration of selection agent.

An additional method of transforming monocots is found in International Publication No. WO 00/12734, and describes the application of the Ac-Ds trasposon system to the insertion of transgenes into plants.

Other methods for the transformation of monocotyledons are known in the art. Thus, this example should be not construed as limiting the scope of the invention to only those examples illustrated above or elsewhere herein Example 39

Method of Enhancing the Biological Activity/Functional Characteristics of Invention Through Molecular Evolution Although many of the most biologically active proteins known are highly effective for their specified function in an organism, they often possess characteristics that make them undesirable for transgenic, therapeutic, agricultural, and/or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic plant or animal production, the bioprocess production and purification of the protein, and use of the protein as a chemical modulator (e.g., herbicide, insectide, etc.), among others. Therefore, there is a need to identify novel variants of isolated proteins possessing characteristics which enhance their application as a therapeutic for treating diseases of both plant and animal origin, in addition to the proteins applicability to common industrial and agricultural applications.

Thus, one aspect of the present invention relates to the ability to enhance specific characteristics of invention through directed molecular evolution. Such an enhancement may, in a non-limiting example, benefit the inventions utility as an essential component in a kit the inventions physical attributes such as its solubility, structure, or codon optimization, the inventions specific biological activity, including any associated enzymatic activity, the proteins enzyme kinetics, the proteins Ki, Kcat, Km, Vmax, Kd, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased genes. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

Directed evolution is comprised of several steps. The first step is to establish a library of variants for the gene or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Gene, 46:145–152, (1986), and Hill, DE, et al, Methods Enzymol., 55:559–568, (1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments—further diversifying the potential hybridation sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2–4 ug of the DNA substrate(s) would be digested with 0.0015 units of Dnase I (Sigma) per ul in 100 ul of 50 mM Tris-HCL, pH 7.4/1 mM MgCl2 for 10–20 min. at room temperature. The resulting fragments of 10–50 bp could then be purified by running them through a 2% low-melting point agarose gel by electrophoresis onto DE81 ion-exchange paper (Whatman) or could be purified using Microcon concentrators (Amicon) of the appropriate molecular weight cuttoff, or could use oligonucleotide purification columns (Qiagen), in addition to other methods known in the art. If using DE81 ion-exchange paper, the 10–50 bp fragments could be eluted from said paper using 1M NaCL, followed by ethanol precipitation.

The resulting purified fragments would then be subjected to a PCR assembly reaction by re-suspension in a PCR mixture containing: 2 mM of each DNTP, 2.2 mM $MgCl_2$, 50 mM KCl, 10 mM Tris·HCL, pH 9.0, and 0.1% Triton X-100, at a final fragment concentration of 10–30 ng/ul. No primers are added at this point. Taq DNA polymerase (Promega) would be used at 2.5 units per 100 ul of reaction mixture. A PCR program of 94 C for 60 s; 94 C. for 30 s, 50–55 C for 30 s, and 72 C for 30 s using 30–45 cycles, followed by 72 C for 5 min using an MJ Research (Cambridge, Mass.) PTC-150 thermocycler. After the assembly reaction is completed, a 1:40 dilution of the resulting primerless product would then be introduced into a PCR mixture (using the same buffer mixture used for the assembly reaction) containing 0.8 um of each primer and subjecting this mixture to 15 cycles of PCR (using 94 C for 30 s, 50 C for 30 s, and 72 C for 30 s). The referred primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailered to the desired level of mutagenesis using the methods described by Zhao, et al. Mucl Acid Res., 25(6):1307–1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336–347, (1997), F. R, Cross, et al., Mol. Cell. Biol., 18:2923–2931, (1998), and A. Crameri., et al., Nat. Biotech., 15:436–438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host For example, a particular varient of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native strucuture which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel varient that provided the desired characteristics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homolog sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436–438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species; each of the above are hereby incorporated in their entirety herein for all purposes.

Example 40

Functional Determination of Proteins Using Microarray

Preparation of DNA Microarrays

Clones in YTK12 yeast cells are grown on CMD W plates at 30° C. PCR in 96 wells plates is used to amplify the inserts as follow: per clone, a 100 ul reaction mix consisting of 80 ul sterile water, 10 ul 10× RedTaq Buffer (Sigma), 2 ul 10 mM dNIP Mix (Boehringer Manheim), 2 ul of a forward primer corresponding to a polynucleotide of the present invention, 100 ng/ul, 2 ul T7 Primer 100 ng/ul, 4 ul RedTaq DNA Polymerase (Sigma) and an aliquot of the yeast colony are mixed and subjected to 95° C. for 2 minutes (once) then 94° C. for 30 seconds, followed by 50° C. for 30 seconds, and 72° C. for 30 seconds (35 to 40 cycles) and finally 72° C. step for 7 minutes. The PCR products are purified using gel filtration cartridges (Edge BioSytems) twice to eliminate completely excess primers. All PCR products are evaluated by agarose gel electrophoresis. Using a robot (TECAN), the PCR products are transferred to 384 well plates and samples are then dried under vacuum and resuspended in 20 ul of 50% DMSO.

The DNA samples are arrayed onto amino silinated coated glass microscopic slides using a microarray GEN III spotter from Molecular Dynamics/Amersham Pharmacia Biotech. After the samples are air dried, UV crosslinking of the samples to the slide can be done by exposing the slides to 50 mJ pulse of light of wavelength 254 nm.

RNA Isolation and Preparation of Labeled mRNA by In Vitro Transcription of cDNA.

Total RNA is isolated from various tissue (leaf, root, flower, stem, meristems, cell cultures, treated or untreated with chemicals or submitted or not to biotic or abiotic stresses) using a RNeasy kit from Qiagen. Total RNA is converted to cDNA as described below. First strand cDNA synthesis can be performed as follows: 3–5 ug of total RNA is mixed with 1 ul of T7-oligo(dT)$_{24}$ primer 5'-GGCCAGT-GAATTGTAATACGCTCACTATAGGGAG-GCGGTTTTTTTTTTTTTTTTTTT TTTTTT-3' (SEQ ID NO:12) and the final volume is brought to 12 ul with DEPC-H$_2$O. After heating the tube at 70° C. for 5 minutes, 4 ul of 5×first Strand Buffer (Life technology), 1 ul of 0.1 M DTT and 1 ul of 10 mM dNTP are added. After 2 minutes incubation at 37° C., 3 ul of reverse transcriptase (SSII RT, 200-unit/ul, Life Technology) is added and incubation at 37° C. for 1 hour followed.

The second strand synthesis is performed as follows: to the first stand reaction mixture 89 ul of DEPC-H$_2$O, 3 ul of 10 mM dNTP, 1 ul of 10 U/ul *E. coli* DNA ligase, 4 ul of 10 U/ul *E. coli* DNA polymerase, and 2 ul of 2 U/ul *E. coli* RNase H are added and incubated at 16° C. for 2 hour. Then 2 ul of 5 U/ul T4 DNA polymerase are added and incubated at 16° C. for 5 min. The reaction is stopped by one phenol/chloroform extraction and the supernatant precipitated in the presence of 2.5 volume of 100% ethanol and 1/10 volume of 5M NH$_4$Ac. After mixing the sample, it is centrifuged immediately at 12 000 g for 5 minutes at room temperature. The pellet is washed twice with 80% ethanol and air dried before being dissolved in 2 ul of RNase free water. In vitro transcription with Cy dye labeling is performed as follow: per reaction, 1 ul T7 10 × reaction buffer (Ambion), 3 ul of 25 mM ATP, CTP, GTP mix, 1 ul of 20 mM UTP (Ambion), 1 ul of cDNA, 3 ul of 5 mM of Cy3 or Cy5 (Amersham), 0.5 ul of the internal control PCR product (i.e. human CCR5), 1 ul of enzyme mix (Ambion, MEGAscript™) and 1 ul of T7 RNA polymerase (USB, 100 units/ul) are combined and incubated 37° C. for 4–6 hours in a water bath in the dark. The template cDNA is then removed by incubating at 37° C. for 15 minutes with 1 ul of RNase-free DNaseI. The RNA probe is then purified using the RNeasy mini protocol for RNA probe purification (Qiagen). Each probe is store protected from light at −70° C.

Microarray Hybridization and Data Analysis.

The two mRNA pools to be compared are mixed and applied to a microarray slide in 36 ul of a hybridization mixture containing 50% formamide, 5×SSC, 0.1% SDS. Hybridization can take place under a glass coverslip in a humidified plastic tube with a lid, in a 42° C. oven for 14–18 hours. The slides are then washed twice for 5 minutes at 42° C. in 0.5×SSC, 0.1% SDS, once for 10 minutes at 42° C. in 0.25×SSC, 0.1% SDS, once in 0.25×SSC, 0.1% SDS at 55° C. for 30 minutes, before being dried under a gentle stream of N$_2$.

Scanning of the slides is performed with a Generation III Array Scanner (Molecular Dynamic) at a PMT of 665V for Cy3 labeled probes and a PTM of 685V for Cy5 labeled probes. Capture of the data and critical analysis (background removal, normalization, and mean values . . . ) is done using the software ArrayVision™ (Imaging Research, Inc.). The Cy5/Cy3 fluorescence ratio and the $\log_{10}$-transformed ratio are calculated from the normalized values. The software SpotFire™ (Spotfire, Inc.) and GeneSpring™ (Silicon Genetics, Inc.) are used for data visualization and clustering analysis.

Example 41

Method of Transforming Plants Using Vacuum Infiltration

Transformation of plants may serve as a vital tool in assessing the biological function of a particular polynucleotide or polypeptide. For example, a plant may be transformed with a vector capable of downregulating a particular gene via anti-sense regulation (i.e., the vector may express a transcript of the gene of interest in the antisense direction), or the vector may simply be capable of overexpressing a particular polypeptide, for example. By observing the resulting phenotypes of the transformant, one may derive protein function using techniques known in the art and described elsewhere herein. Other uses for transformation methods are described elsewhere herein.

The following method of transforming plant material may be applicable to any plant species, though is particularly suited for use in Arabidopsis.

Grow Arabidopsis at 20° C., 8 hr light, 18° C. 16 dark until needed for transformation. Fertilize once a week from below. Thin plants to ~1 per square inch. Use immediately upon bolting. Short days allow stronger vegetative plant growth and increase seed yield.

Transfer plants to 20° C., 16 hr light, 18° C. 8 hr dark. The plants should bolt quickly, and they are ready to infiltrate when the primary inflorescences are 10–15 cm tall and the secondary inflorecences are appearing at the rosette.

In the meantime, transform your constructs into *Agrobacterium tumefaciens* strain ERA105 (Koncz and Schell, 1986) (see Direct *Agrobacterium* Transformation:Freeze-Thaw Method below). When the plants are ready to transform use 1 ml of an overnight culture to innoculate a 500 ml culture of YEB medium (2 L flask) containing the appropriate antibiotic for your construct and 50 ug/mL rifampicin (C58 Agro_and or 25 mg/mL gentamycin (pMP90). Grow cultures 2 days at 28° C., ~275 rmp. YEB media is described below.

When $OD_{600}$ is greater than 2.0, centrifuge the culture 30 min, 3500 rpm and resuspend it in 0.5–1.0 ml of infiltration medium described below.

Place resuspended culture in a container with a large bell jar, and invert pots containing plants to be infiltrated into the infiltration medium so that the entire plant is covered (including the rosette, but not too much soil). Remove any large air bubbles under the plants. Draw a vacuum (~700 Hg). Close the suction, and allow the plants to sit under vacuum for 5 min. Quickly release the vacuum pressure. Briefly drain the pots.

Grow infiltrated plants as before in 20° C., 16 hr light, 18° C. 8 hr dark. Stake plants as the bolts grow. When the plants are finished flowering, harvest the $T_0$ seeds.

Sterilize seeds and screen for transformants on the selective medium described below. Transfer dark green (resistant) plants to secondary selection plate a week after germination, then to soil after 6–10 days. Keep new transplants covered for several days.

| Plant media: | | |
|---|---|---|
| For 1 L | Vacuum Infiltration Medium | Selection Medium |
| MS Salts | 2.2 g | 4.3 g |
| B5 Vitamins, 1000X | 1.0 mL | 1.0 mL |
| Sucrose | 50 g | 10 g |
| MES, 200 mg/mL | 2.5 mL | 2.5 mL |
| pH 5.7 with KOH | | |
| Benzylamonipurine (BAP, 1 mg/mL) | 44 µL | — |
| Silweet L-77 | 200 µL | — |
| Phytagar | — | 8 g |
| Bacterial Media | YEP | |
| Yeast extract | 1.0 g | |
| Beef Extract | 5.0 g | |
| Peptone | 5.0 g | |
| Sucrose | 5.0 g | |
| $MgSO_4$ | 0.5 g | |

The skilled artisan would appreciate that the above transformation method could be modified to apply to other species of plants. Such modification may include the addition of new steps, the deletion of any of the steps described, and/or subsititution of reagents.

Direct *Agrobacterium* Transformation:Freeze-Thaw Method.

Grow an *Agrobacterium* strain containing the appropriate helper Ti plasmid in 5 mL of YEP medium (YEP medium is described elsewhere herein) overnight at 28° C. Add 2 ml of the overnight culture to 50 ml YEP medium in a 259 mL flask and shake vigorously (250 rpm) at 28° C. until the culture grows to an $OD_{600}$ of 0.5 to 1.0. Chill the culture on ice. Centrifuge the cell suspension at 3000 g for 5 min at 4° C.

Discard the supernatant solution. Resuspend the cells in 1 mL of 20 mM $CaCl_2$ solution (ice-cold). Dispense 0.1 mL aliquots into prechilled Eppendorf tubes. Add about 1 ug of plasmid DNA to the cells.

Freeze the cells in liquid nitrogen Thaw the cells by incubating the test tube in a 37° C. water bath for 5 min. Add 1 mL of YEP medium to the tube and incubate at 28° C. for 2–4 hr with gentle rocking. This period allows the bacteria to express the antibiotic resistance genes. Centrifuge the tubes for 30 s in an Eppendorf centrifuge. Discard the supernatant solution. Resuspend the cells in 0.1 mL YEP medium Spread the cells onto a YEP agar plate containing 3–5 ug/mL tetracycline and 10–25 ug/mL kanamycin. Incubate the plate at 28° C. Transformed colonies should appear in 2–3 days.

The skilled artisan would appreciate that the above transformation method could be modified to apply to other species of plants. Such modification may include the addition of new steps, the deletion of any of the steps described, and/or subsititution of reagents.

Example 42

Functional Determination of Proteins Using Metabolite Profiling

The present invention encompasses the application of metabolite profiling to the identification of gene function for the polypeptides of the present invention. In one example, transgenic plants could be produced which are either incapable of expressing a protein of the present invention, or that have decreased expression levels of a protein of the present invention. Such transgenic plants could be produced by creating knockout constructs to inactivate or delete the endogenous gene, for example, using methods known in the art and described elsewhere herein. Alternatively, the transgenic plants could be produced by inserting into the plant a construct that expresses antagonists of a protein of the present invention (e.g., antisense oligonucleotides, antisense genes, antibodies, etc.). Other examples of methods of producing transgenic plants, including specific strategies, are known in the art, some of which are described elsewhere herein.

Once a protein of the present invention is inactivated, or its expression inhibited, the resulting metabolite profile of the plant can be ascertained, and the function of the protein assigned. Some of the anticipated metabolic profiles of inhibiting or inactivating the expression of a protein of the present invention in a plant may resemble known nutritional deficiencies, pathogenic diseases, biotic stresses, or abiotic stresses, for example, many of which are disclosed elsewhere herein. In addition, the metabolic profile of a transgenic plant of the present invention may be useful in identifying the specific pathways the polypeptide of the present invention is a member of, in addition, to identifying the potential downstream and/or upstream effectors or affectors, respectively. In addition, it may be possible to identify the mode of action of a polypeptide of the present invention.

A number of methods are known in the art for identifying the metabolic profile of a plant. A non-limiting example is provided by Sauter, H., et al., in "Metabolic Profiling of Plants: A New Diagnostic Technique", Synthesis and Chemistry of Agrochemicals II, Baker, D. R, Fenyes, J. G., and Moberg, W. K, eds, ACS Symposium Series, 433, Chapter 24, pp. 288–299, (1991). Briefly, transgenic plants of the invention, or plants in which the expression of a polypeptide of the present invention is inhibited or inactivated, are grown in growth chambers. The shoots are harvested and immediately deep frozen until further treatment. The frozen plant samples are weighed and a threefold amount (W:W) of ethanol is added. The mixture is then macerated in a mixer and the resulting suspension is left for 2 hours for extraction. The next steps are filtration, evaporation, and silylation with N-Methyl-N-(trimethylsilyl)triflouroacetamide (MSTFA). Internal standard alkanes are also added, thus allowing for the calculation of retention coefficients, as well as, quantification. The crude mixture is then subjected to gas chromatography on a methyl silicon gum fused silica capillary column (30 m DB-1. Injection temperature 230° C. Oven temperature 100°–320° C., 4° C. min; 15 min 320° C.). Retention coefficients are then calculated relative to internal standards (n-C10H22=1000, n-C28H58=2800).

The above protocol can be applied to numerous test plants, in addition, to controls. The data from the resulting profiles are then grouped together (i.e., one group for the test plants, another group for the controls) to arrive at an average profile for each group. In the latter step, the corresponding peaks (i.e., those peaks with equal retention coefficients) are grouped together and the peak heights are subjected to statistical analysis.

The differences in metabolic profiles between the test and control plants are determined by calculating the "difference profile" between the two groups. The difference profile is calculated by dividing the peal heights. This difference profile provides a semiquantitative estimate of the change in magnitude of one metabolic with respect to the other.

Once the above is completed, the peaks are then associated with particular metabolites (i.e., the metabolite identify of each peak is determined). By comparing the metabolite profile of proteins known to modulate specific pathways in a plant, to those of the present invention, clues for and/or identification of the function of a polypeptide of the present invention may be determined. Other methods are known in the art, and any one or more steps, may be equally substituted with such methods.

Example 43

Functional Determination of Proteins Using Morphological Phenotyping

The present invention encompasses the application of morphological phenotyping to the identification of gene function for the polypeptides of the present invention. In one example, transgenic plants could be produced which are either incapable of expressing a protein of the present invention, or that have decreased expression levels of a protein of the present invention. Such transgenic plants could be produced by creating knockout constructs to inactivate or delete the endogenous gene, for example, using methods known in the art and described elsewhere herein. Alternatively, the transgenic plants could be produced by inserting into the plant a construct that expresses antagonists of a protein of the present invention (e.g., antisense oligonucleotides, antisense genes, antibodies, etc.). Other examples of methods of producing transgenic plants, including specific strategies, are known in the art, some of which are described elsewhere herein.

Once a protein of the present invention is inactivated, or its expression inhibited, the resulting morphological phenotype of the plant can be ascertained, and the function of the protein assigned. Some of the anticipated phenotypes of inhibiting or inactivating the expression of a protein of the present invention in a plant may resemble known nutritional deficiencies, pathogenic diseases, biotic stresses, or abiotic stresses, for example, many of which are disclosed elsewhere herein.

Example 44

Functional Determination of Proteins Using TransGenomic Technology (TGT)

The present invention encompasses the application of TransGenomic Technology (TGT) to the identification of gene function for the polypeptides of the present invention (Cambia Biosystems, Bellevue, Wash.). TGT combines both genomics and functional genomics, enabling the association of gene sequences (e.g., the polynucleotide sequences of the present invention) with specific phenotypes or traits. The technology is based upon the random integration of reporter gene [e.g. beta-Glucuronidase (GUS), BoGUS, GFP] transposons throughout a plant's genome (specifically rice and Arabidopsis).

The transposon may comprise an enhancer trap vector containing a transcriptional activator and a reporter gene capable of responding to the transactivator. Since the integration is random, it is expected that the transposon may integrate near a gene regulatory element—effectively turning on the transactivator gene, the activity of said gene promoting activation of the reporter gene. Thus, by repeating the process above, a large population of cell lines with unique expression patterns can be generated. These "pattern lines" are genetically characterized in an effort to select lines with desired expression patterns. The pattern lines can be used for reverse genetics studies to identify lines with mutations in genes of interest and may also be used as a genetic background to obtain gain-of-function (GOF) and loss-of-function (LOF) mutations. Moreover, novel expression (or lack of expression) patterns may uncover novel phenotypes and traits. In addition, the pattern lines showing desirable expression patterns could serve as a genetic foundation to direct the expression of genes in target tissues or at desired developmental stages.

The TGT technology described above can be used to identify the function of the polynucleotides and/or polypeptides of the present invention. For example, the polynucleotide sequences of the present invention can be used to generate PCR primers suitable for the screening and identification of cell lines positively tagged with the TGT technology upstream of a polynucleotide of the present invention. Once identified, the function of the polynucleotide sequence may be ascertained by linking the genes of the present invention tagged with the TGT technology with specific phenotypes or traits observed in a particular cell line, or pattern line. Another possible application of TGT to the polynucleotides of the present invention would be in targeting gene expression of selected polynucleotides of the present invention. For example, polynucleotide sequences of the present invention flanked by an upstream regulatory sequence may be introduced into pattern lines showing desired expression patterns using techniques known in the art of molecular biology and described elsewhere herein.

A number of variations of the above technology are known in the art and would be appreciated by the skilled artisan. For example, the skilled artisan would appreciate that other transposons, reporter genes, and activating sequences, etc., could be substituted or used in conjunction with the TGT technology. Specific methods of applying TGT technology can be found, for example, in Wilson K J, et al., Microbiol, 141:1691–1705, (1995), and in U.S. Pat. Nos. 5,879,906, 5,599,670, and 5,432,081; which are hereby incorporated by reference in their entirety herein.

What is claimed is:

1. An isolated nucleic acid, wherein the nucleic acid comprises a polynucleotide selected from the group consisting of:
   a) a polynucleotide having a sequence as set forth in SEQ ID NO:1; and
   b) a polynucleotide encoding a polypeptide having a sequence as set forth in SEQ ID NO:2.

2. The nucleic acid of claim 1, wherein the nucleic acid comprises a polynucleotide encoding the polypeptide having the sequence as set forth in SEQ ID NO:2.

3. The nucleic acid of claim 1, wherein the nucleic acid comprises a polynucleotide having the sequence as set forth in SEQ ID NO: 1.

4. A vector comprising the nucleic acid of claim 1.

5. The nucleic acid of claim 1, wherein the nucleic acid encodes a polypeptide that functions to increase an environmental stress response in a plant, and wherein the environmental stress is selected from the group consisting of high salinity, drought and low temperature.

6. The nucleic acid of claim 1, wherein overexpression of the nucleic acid in a plant increases the plant's tolerance to an environmental stress, and wherein the environmental stress is selected from the group consisting of high salinity, drought and low temperature.

7. The nucleic acid of claim 6, wherein the environmental stress is salt.

8. The nucleic acid of claim 1, wherein the nucleic acid encodes a polypeptide that functions in a sodium transport system.

9. A transgenic plant cell comprising a transgene, wherein the transgene comprises a polynucleotide selected from the group consisting of:
   a) a polynucleotide having a sequence as set forth in SEQ ID NO:1; and
   b) a polynucleotide encoding a polypeptide having a sequence as set forth in SEQ ID NO:2.

10. A transgenic plant comprising transgene, wherein the transgene comprises a polynucleotide selected from the group consisting of:
   c) a polynucleotide having a sequence as set forth in SEQ ID NO:1; and
   d) a polynucleotide encoding a polypeptide having a sequence as set forth in SEQ ID NO:2.

11. The plant of claim 10, wherein the plant is a monocot.

12. The plant of claim 10, wherein the plant is a dicot.

13. The plant of claim 10, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass and a forage crop plant.

14. A plant seed comprising a transgene, wherein the transgene comprises a polynucleotide selected from the group consisting of:
   a) a polynucleotide having a sequence as set forth in SEQ ID NO:1; and
   b) a polynucleotide encoding a polypeptide having a sequence as set forth in SEQ ID NO:2.

15. The seed of claim 14, wherein the seed is true breeding for an increased tolerance to environmental stress as compared to a wild type variety of the seed, and wherein the environmental stress is selected from the group consisting of high salinity, drought and low temperature.

16. A method of increasing a plant's tolerance to an environmental stress, the method comprising the step of, increasing the expression of nucleic acid transformed into the plant, wherein the nucleic acid is selected from the group consisting of: a) a polynucleotide having a sequence as set forth in SEQ ID NO: 1; and b) a polynucleotide encoding a polypeptide having a sequence as set forth in SEQ ID NO: 2, and wherein the environmental stress is selected from the group consisting of high salinity, drought and low temperature.

17. The method of claim 16, wherein the nucleic acid comprises a polynucleotide encoding the polypeptide having the sequence as set forth in SEQ ID NO:2.

18. The method of claim 16, wherein the nucleic acid comprises a polynucleotide having the sequence as set forth in SEQ ID NO:1.

19. The method of claim 16, wherein the nucleic acid encodes a polypeptide that functions in sodium transport system.

20. The method of claim 16, wherein the plant is transformed with a promoter that is operably linked to the nucleic acid.

21. The method of claim 20, wherein the promoter is tissue specific.

22. The method of claim 20, wherein the promoter is developmentally regulated.

23. A method of producing a transgenic plant containing a nucleic acid wherein the plant has an increased tolerance to an environmental stress as compared to a wild type variety of the plant, the method comprising the steps of transforming a plant cell with an expression vector comprising the nucleic acid; and generating from the plant cell the transgenic plant, wherein the nucleic acid is selected from the group consisting of: a) a polynucleotide having a sequence as set forth in SEQ ID NO: 1; and b) a polynucleotide encoding a polypeptide having a sequence as set forth in SEQ ID NO: 2, and wherein the environmental stress is selected from the group consisting of high salinity, drought and low temperature.

24. The method of claim 23, wherein the plant is a monocot.

25. The method of claim 23, wherein the plant is a dicot.

26. The method of claim 23, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass and a forage crop plant.

27. The method of claim 23, wherein the nucleic acid comprises a polynucleotide encoding the polypeptide having the sequence as set forth in SEQ ID NO:2.

28. The method of claim 26, wherein the nucleic acid comprises a polynucleotide having the sequence as set forth in SEQ ID NO:1.

29. The method of claim 26, wherein the nucleic acid encodes a polypeptide that functions in a sodium transport system.

30. The method of claim 26, wherein the plant is transformed with a promoter that is operably linked to the nucleic acid.

31. The method of claim 30, wherein the promoter is tissue specific.

32. The method of claim 30, wherein the promoter is developmentally regulated.

* * * * *

SEQUENCE LISTING

```
<160> NUMBER OF SEQ ID NOS: 32

<210> SEQ ID NO 1
<211> LENGTH: 1677
<212> TYPE: DNA
<213> ORGANISM: Physcomitrella patens

<400> SEQUENCE: 1
atggcgacca atgatgtcgt gagcgtttcg cattctatgc tactaaaagc tacagatctc      60
aaagatgacc gaatcgatgt aatttcaatc tgtctctttg tatttttact ctgtgcgtgc     120
attgtgctgg ggcaccttct ggaggaaaat cggtggatga atgagtctat tactgctctt     180
cttctgggac tctttactgg atctatagtg ttgatttcaa gcaaaggtca aggttctcat     240
attctggagt ttgatgaaga gcttttcttc atataccttc ttccacctat aatcttcaat     300
gctgggttcc aggttaagaa gaaggaattc tttcggaatt tcataacaat catgtttttt     360
ggagttatag gagtctttat ttctttcgga attatctcaa caggaagttg gtatttcttc     420
tccaagttcg gacttaagaa cctgcctatt cgagatatcc tagctattgg agtcatcttt     480
tctgctaccg attccgtctg cacgttgcag gtgctgaacc aagatgaaac ccctctactt     540
tacagtttgg tcttttgggga aggagtcgta aatgatgcta cttctgtggt tctgtctcga     600
gctgttcaaa catacaactt tgacaatttt acatccttag aaggcttaca aattggaggc     660
agtttcttgt acttattctt ctcgagttgc atcctgggaa tcgcgtcggg cttaataagc     720
gcatatatca tcaagacaat gtactttggc aggcattcca cggatcgtga aatagcaatc     780
atgacattga tggcgtattt atcttacgtc tttgcagagc ttttctactt gagtggaatt     840
ctctcagtgt tcttttgcgg cattgtaatg tctcattaca cttggcataa cgtcacggag     900
aattctcgaa tcacaagcaa gcattccttt gcaacgatgt cattcattgc agagacgttc     960
atatttctat atgttggaat ggatgctctg gatttcgaaa aatggaagat gatgcaatcc    1020
agtttcacgg aatctgcggg ctatttggta gcttgttgtt tctggtcctg ttagggaggg    1080
ccgcatttgt gttcccactc tctgctttgt ccaactacag cacaaagtct ccagacgcga    1140
agattaattt acgccaaatg gttattatct ggtgggctgg actaatgcga ggtgctgtcg    1200
rbtcaatagc actggcgttc aaccagggtg gtgatgcaaa ggctcaaacc aagccacgct    1260
```

```
aatggtcatt actatcatca ttgtcctctt cagcactatt gtgttcggca ctgcaaccaa    1320
gcctcttatt agctggctac ttccacctca tttcagatca aattacagtg attcagccag    1380
tctctcccca aaagcgtctc ttgatgctga ctttcatata ccactcctta tggatacaga    1440
gcgtgaagaa ttagaagcaa atgatcgatc tacgataaat caaatcctaa atggtcttcc    1500
ttgtcctcag tcaataggca tgctgctgac tgcaccaaga tcaaccatcc accatgtatg    1560
gagaaaattt gatgattctt acatgcggcc cacgtttggt gggagaggat atgttaggtt    1620
ggtgtcacgg cgtgatatgg aatacaagaa gatgaaatcc ttgaagatca cagttga      1677
```

<210> SEQ ID NO 2
<211> LENGTH: 556
<212> TYPE: PRT
<213> ORGANISM: Physcomitrella patens

<400> SEQUENCE: 2

```
Met Ala Thr Asn Asp Val Val Ser Val Ser His Ser Met Leu Leu Lys
  1               5                  10                  15

Ala Thr Asp Leu Lys Asp Asp Arg Ile Asp Val Ile Ser Ile Cys Leu
             20                  25                  30

Phe Val Phe Leu Leu Cys Ala Cys Ile Val Leu Gly His Leu Leu Glu
         35                  40                  45

Glu Asn Arg Trp Met Asn Glu Ser Ile Thr Ala Leu Leu Leu Gly Leu
     50                  55                  60

Phe Thr Gly Ser Ile Val Leu Ile Ser Ser Lys Gly Gln Gly Ser His
 65                  70                  75                  80

Ile Leu Glu Phe Asp Glu Glu Leu Phe Phe Ile Tyr Leu Leu Pro Pro
                 85                  90                  95

Ile Ile Phe Asn Ala Gly Phe Gln Val Lys Lys Lys Glu Phe Phe Arg
            100                 105                 110

Asn Phe Ile Thr Ile Met Phe Phe Gly Val Ile Gly Val Phe Ile Ser
        115                 120                 125

Phe Gly Ile Ile Ser Thr Gly Ser Trp Tyr Phe Phe Ser Lys Phe Gly
    130                 135                 140

Leu Lys Asn Leu Pro Ile Arg Asp Ile Leu Ala Ile Gly Val Ile Phe
145                 150                 155                 160

Ser Ala Thr Asp Ser Val Cys Thr Leu Gln Val Leu Asn Gln Asp Glu
                165                 170                 175

Thr Pro Leu Leu Tyr Ser Leu Val Phe Gly Glu Gly Val Val Asn Asp
            180                 185                 190

Ala Thr Ser Val Val Leu Ser Arg Ala Val Gln Thr Tyr Asn Phe Asp
        195                 200                 205

Asn Phe Thr Ser Leu Glu Gly Leu Gln Ile Gly Gly Ser Phe Leu Tyr
    210                 215                 220

Leu Phe Phe Ser Ser Cys Ile Leu Gly Ile Ala Ser Gly Leu Ile Ser
225                 230                 235                 240

Ala Tyr Ile Ile Lys Thr Met Tyr Phe Gly Arg His Ser Thr Asp Arg
                245                 250                 255

Glu Ile Ala Ile Met Thr Leu Met Ala Tyr Leu Ser Tyr Val Phe Ala
            260                 265                 270

Glu Leu Phe Tyr Leu Ser Gly Ile Leu Ser Val Phe Phe Cys Gly Ile
        275                 280                 285

Val Met Ser His Tyr Thr Trp His Asn Val Thr Glu Asn Ser Arg Ile
    290                 295                 300
```

```
Thr Ser Lys His Ser Phe Ala Thr Met Ser Phe Ile Ala Glu Thr Phe
305                 310                 315                 320

Ile Phe Leu Tyr Val Gly Met Asp Ala Leu Asp Phe Glu Lys Trp Lys
                325                 330                 335

Met Met Gln Ser Phe Thr Glu Ser Ala Gly Leu Phe Gly Ser Leu Leu
            340                 345                 350

Phe Leu Val Leu Leu Gly Arg Ala Ala Phe Val Phe Pro Leu Ser Ala
        355                 360                 365

Leu Ser Asn Tyr Ser Thr Lys Ser Pro Asp Ala Lys Ile Asn Leu Arg
370                 375                 380

Gln Met Val Ile Ile Trp Trp Ala Gly Leu Met Arg Gly Ala Val Ser
385                 390                 395                 400

Ile Ala Leu Ala Phe Asn Gln Gly Gly Asp Ala Lys Asp Ser Asn Gln
                405                 410                 415

Ala Thr Leu Met Val Ile Thr Ile Ile Val Leu Phe Ser Thr Ile
            420                 425                 430

Val Phe Gly Thr Ala Thr Lys Pro Leu Ile Ser Trp Leu Leu Pro Pro
        435                 440                 445

His Phe Arg Ser Asn Tyr Ser Asp Ser Ala Ser Leu Ser Pro Lys Ala
    450                 455                 460

Ser Leu Asp Ala Asp Phe His Ile Pro Leu Leu Met Asp Thr Glu Arg
465                 470                 475                 480

Glu Glu Leu Glu Ala Asn Asp Arg Ser Thr Ile Asn Gln Ile Leu Asn
                485                 490                 495

Gly Leu Pro Cys Pro Gln Ser Ile Gly Met Leu Leu Thr Ala Pro Arg
            500                 505                 510

Ser Thr Ile His His Val Trp Lys Phe Asp Asp Ser Tyr Met Arg Pro
        515                 520                 525

Thr Phe Gly Gly Arg Gly Tyr Val Arg Leu Val Ser Arg Arg Asp Met
    530                 535                 540

Asp Ile Gln Glu Asp Glu Ile Leu Glu Asp His Ser
545                 550                 555

<210> SEQ ID NO 3
<211> LENGTH: 785
<212> TYPE: DNA
<213> ORGANISM: Physcomitrella patens
<220> FEATURE:
<221> NAME/KEY: modified_base
<222> LOCATION: (694)
<223> OTHER INFORMATION: a, t, c, g, other or unknown
<220> FEATURE:
<221> NAME/KEY: modified_base
<222> LOCATION: (782)
<223> OTHER INFORMATION: a, t, c, g, other or unknown

<400> SEQUENCE: 3
cggcacgaga acctttgcag ctgctaaggc atgcaggtg gatgcccgca aagctttaac      60
tctcggcatc ctgatgaata ccaaaggatt ggtggagctt attgttctga acatcggttt   120
agatcgtgga gttctgaatt cggagacttt tgcaatcatg gtgctgatgg ctctcttcac   180
aacgttcatg acaacacctc tggtaatggc tatatataaa ccagccacga atcccactcc   240
ttacactcgt aggactttgg aaatggagga ctcgaaggat gacttgcgaa tattgtcatg   300
cgtgcacgga atgaagaacg tggctgccat gatcaatctt acagaagcga ccagggcat    360 gcgcaaacgt actctgcgcc tgtatatttt gcatttgatg gaactatccg aacgtacttc   420
```

-continued

```
tgccattatg attgtccagc gggcacgtcg gaatgggcgc cctttttca atcagagcaa      480
acattcggac aacaaagatc aaattgttgc ggccttcgag acatatgaac aactaagcaa      540
ggtgactgtg aggcctatga ctgcaatttc cgggttcgac gacatgcacg aagacatatg      600
tgcgactgct gctgacaagc ggactgcctt gatcatgctt cctttccaca aatcacccaa      660
actggacggg cacttcgatt ctactccagg tttncgaaca gttaatcaca aggtcctcaa      720
gcatgcaccg tgctctgttg ctattctaat cgatcgtgga gtcggtggat caacccaagt      780
gnctt                                                                  785
```

<210> SEQ ID NO 4
<211> LENGTH: 2624
<212> TYPE: DNA
<213> ORGANISM: Physcomitrella patens

<400> SEQUENCE: 4

```
tggcaccagc aagatggcgg acgctgtggc gtgcaaaact atgtcggcta catccaatgg       60
agtgtggcag ggagatgtgc ccgttcattt tgctcttcct ctgctcatcg ttcaaattgt      120
cctcgttttg gcaatcactc gggcgttagc ttttgtcctg aagcctttga acagccccg      180
cgtcgtcgcc gagattatag gcggaatatt gcttggtcca tctgcttttg gacgcaataa      240
ggactacctg catacgattt ttccacatga aagtgttatc attctggagg tctttgcaga      300
catgggactt ttattctttt tgttcatggt ggggttagag ctcgatatga cccagattcg      360
gaaaaccgga aagcaagcta tgtccattgc tgcagctgga atcactctgc ctttcgttgc      420
aggtgtcggt gtttccttcg tcctgcatct tacaattgca ccagagggag cttttggtcc      480
gtttctcgtg ttcatgggag ttgctatgtc catcactgct ttccctgttc tggcacgtat      540
tttggcggag aggaagcttt tgactaccga agtagggcaa ttggcgatgt cagcagctgc      600
agttaatgac gtggttgctt gggttctttt agcgttggcg gtcgctttgt cgggctccgg      660
aaggagccca gcaattgttg catgggttct gttgtgtgga atcgcatttt gtctggccat      720
cttccttgtg gttcaaccat gcatgcaatg ggttgctcat cgatcgcccg acaatgagcc      780
tgtcaaagaa tacattgtag cattgacttt actttgtgtt ctcgttgctg gattctgtac      840
tgatgcgata ggagttcatt ccattttttgg cgcgtttctg tttggacttg ttatacctaa      900
agagggtcct ttcgcagcgg ctttggttga gaaattagaa gattttgtat ctatcctctt      960
gctgcctctc tactttgcat cgagtggact gaagaccaac attggagcta ttcacagcgc     1020
gcaatctttt ggccttttgg tcttggttat cagcgttgct tgtctgggta aaattctcgg     1080
aacctttgca gctgctaagg catgcagggt ggatgcccgc aaagctttaa ctctcggcat     1140
cctgatgaat accaaaggat tggtggagct tattgttctg aacatcggtt tagatcgtgg     1200
agttctgaat tcggagactt ttgcaatcat ggtgctgatg gtctctcttca caacgttcat     1260
gacaacacct ctggtaatgg ctatatataa accagccagg aatcccactc cttacactcg     1320
taggactttg gaaatggagg actcgaagga tgacttgcga atattgtcat gcgtgcacgg     1380
aatgaagaac gtggctgcca tgatcaatct tacagaagcg accaggggca tgcgcaaacg     1440
tactctgcgc ctgtatattt tgcatttgat ggaactatcc gaacgtactt ctgccattat     1500
gattgtccag cgggcacgtc ggaatgggcg ccctttttc aatcagagca acattcgga      1560
caacaaagat caaattgttg cggccttcga gacatatgaa caactaagca aggtgactgt     1620
gaggcctatg actgcaattt ccgggttcga cgacatgcac gaagacatat gtgcgactgc     1680
tgctgacaag cggactgcct tgatcatgct tcctttccac aaatcaccca gactggacgg     1740
```

```
gcacttcgat tctactccag gtttccgaac agttaatcag aaggtcctca agcatgcacc    1800
gtgctctgtt gctattctaa tcgatcgtgg agtcggtgga tcagcccaag tgccttccag    1860
caacgttgat cacaatgttg tcgtgtactt ctttggtggt cctgacgaca gggaagctct    1920
ggcatatggt ttccgtatgg ctgagcatcc gggagttaag cttcatgtta tccgtttcct    1980
ttctcacagc gtcgtcatgg acgacggcca tggaggatta gcttccgtcg atcagaggt    2040 atctgagatt ggcaagacgg aggtgagcga tactcgtttc cagttcgcga tgcatggtct    2100
ggaccaaaac aggcaaaggg agttggatga agaagccttg gccatgtgc gtaggaggca    2160 agcttctgaa gatggaagag tcacatacgt agaaatgcag gtatctgagc ctcttgaaga    2220
ggtggtgaga ttgagtagct ctcgtgaaca cgatattatt ttggttggcc gatcgagaag    2280
gccaacgcca ttttagagc gattccgtcg taagcacgca gaatatgcag agcttggccc    2340
tattggagat gctctgatgg ccccacaggt acgagcatct gtcttagtat ttcagcagca    2400
cgatcatgtg cttgccgatc cacttcctaa tacctctgaa acggaggccg tcaaagagtt    2460
gcagaccttc ccatcatcca aggaattggt ggatcgtaaa ggtgatgtac agaagatcga    2520
cttgtcttct cctgaccacc gcgtgtatat gacccgggtc tagagcggcc gccaccgcgg    2580
tggagctcca gcttttgttc cctttagtga gggttaattg cgcg                     2624
```

<210> SEQ ID NO 5
<211> LENGTH: 849
<212> TYPE: PRT
<213> ORGANISM: Physcomitrella patens

<400> SEQUENCE: 5

```
Met Ala Asp Ala Val Ala Cys Lys Thr Met Ser Ala Thr Ser Asn Gly
 1               5                  10                  15

Val Trp Gln Gly Asp Val Pro Val His Phe Ala Leu Pro Leu Leu Ile
             20                  25                  30

Val Gln Ile Val Leu Val Leu Ala Ile Thr Arg Ala Leu Ala Phe Val
         35                  40                  45

Leu Lys Pro Leu Lys Gln Pro Arg Val Val Ala Glu Ile Ile Gly Gly
     50                  55                  60

Ile Leu Leu Gly Pro Ser Ala Phe Gly Arg Asn Lys Asp Tyr Leu His
 65                  70                  75                  80

Thr Ile Phe Pro His Glu Ser Val Ile Leu Glu Val Phe Ala Asp
                 85                  90                  95

Met Gly Leu Leu Phe Phe Leu Phe Met Val Gly Leu Glu Leu Asp Met
            100                 105                 110

Thr Gln Ile Arg Lys Thr Gly Lys Gln Ala Met Ser Ile Ala Ala Ala
        115                 120                 125

Gly Ile Thr Leu Pro Phe Val Ala Gly Val Gly Val Ser Phe Val Leu
    130                 135                 140

His Leu Thr Ile Ala Pro Glu Gly Ala Phe Gly Pro Phe Leu Val Phe
145                 150                 155                 160

Met Gly Val Ala Met Ser Ile Thr Ala Phe Pro Val Leu Ala Arg Ile
                165                 170                 175

Leu Ala Glu Arg Lys Leu Leu Thr Thr Glu Val Gly Gln Leu Ala Met
            180                 185                 190

Ser Ala Ala Ala Val Asn Asp Val Val Ala Trp Val Leu Leu Ala Leu
        195                 200                 205

Ala Val Ala Leu Ser Gly Ser Gly Arg Ser Pro Ala Ile Val Ala Trp
```

```
                    210                 215                 220
Val Leu Leu Cys Gly Ile Ala Phe Cys Leu Ala Ile Phe Leu Val Val
225                 230                 235                 240

Gln Pro Cys Met Gln Trp Val Ala His Arg Ser Pro Asp Asn Glu Pro
                245                 250                 255

Val Lys Glu Tyr Ile Val Ala Leu Thr Leu Leu Cys Val Leu Val Ala
            260                 265                 270

Gly Phe Cys Thr Asp Ala Ile Gly Val His Ser Ile Phe Gly Ala Phe
        275                 280                 285

Leu Phe Gly Leu Val Ile Pro Lys Gly Pro Phe Ala Ala Ala Leu
    290                 295                 300

Val Glu Lys Leu Glu Asp Phe Val Ser Ile Leu Leu Pro Leu Tyr
305                 310                 315                 320

Phe Ala Ser Ser Gly Leu Lys Thr Asn Ile Gly Ala Ile His Ser Ala
                325                 330                 335

Gln Ser Phe Gly Leu Leu Val Leu Val Ile Ser Val Ala Cys Leu Gly
                340                 345                 350

Lys Ile Leu Gly Thr Phe Ala Ala Ala Lys Ala Cys Arg Val Asp Ala
            355                 360                 365

Arg Lys Ala Leu Thr Leu Gly Ile Leu Met Asn Thr Lys Gly Leu Val
        370                 375                 380

Glu Leu Ile Val Leu Asn Ile Gly Leu Asp Arg Gly Val Leu Asn Ser
385                 390                 395                 400

Glu Thr Phe Ala Ile Met Val Leu Met Ala Leu Phe Thr Thr Phe Met
                405                 410                 415

Thr Thr Pro Leu Val Met Ala Ile Tyr Lys Pro Ala Arg Asn Pro Thr
                420                 425                 430

Pro Tyr Thr Arg Arg Thr Leu Glu Met Glu Asp Ser Lys Asp Asp Leu
        435                 440                 445

Arg Ile Leu Ser Cys Val His Gly Met Lys Asn Val Ala Ala Met Ile
    450                 455                 460

Asn Leu Thr Glu Ala Thr Arg Gly Met Arg Lys Arg Thr Leu Arg Leu
465                 470                 475                 480

Tyr Ile Leu His Leu Met Glu Leu Ser Glu Arg Thr Ser Ala Ile Met
                485                 490                 495

Ile Val Gln Arg Ala Arg Arg Asn Gly Arg Pro Phe Phe Asn Gln Ser
            500                 505                 510

Lys His Ser Asp Asn Lys Asp Gln Ile Val Ala Phe Glu Thr Tyr
        515                 520                 525

Glu Gln Leu Ser Lys Val Thr Val Arg Pro Met Thr Ala Ile Ser Gly
    530                 535                 540

Phe Asp Asp Met His Glu Asp Ile Cys Ala Thr Ala Ala Asp Lys Arg
545                 550                 555                 560

Thr Ala Leu Ile Met Leu Pro Phe His Lys Ser Pro Arg Leu Asp Gly
                565                 570                 575

His Phe Asp Ser Thr Pro Gly Phe Arg Thr Val Asn Gln Lys Val Leu
            580                 585                 590

Lys His Ala Pro Cys Ser Val Ala Ile Leu Ile Asp Arg Gly Val Gly
        595                 600                 605

Gly Ser Ala Gln Val Pro Ser Ser Asn Val Asp His Asn Val Val Val
    610                 615                 620

Tyr Phe Phe Gly Gly Pro Asp Asp Arg Glu Ala Leu Ala Tyr Gly Phe
625                 630                 635                 640
```

-continued

```
Arg Met Ala Glu His Pro Gly Val Lys Leu His Val Ile Arg Phe Leu
                645                 650                 655
Ser His Ser Val Val Met Asp Asp Gly His Gly Gly Leu Ala Ser Val
            660                 665                 670
Gly Ser Glu Val Ser Glu Ile Gly Lys Thr Glu Val Ser Asp Thr Arg
        675                 680                 685
Phe Gln Phe Ala Met His Gly Leu Asp Gln Asn Arg Gln Arg Glu Leu
    690                 695                 700
Asp Glu Glu Ala Leu Gly His Val Arg Arg Gln Ala Ser Glu Asp
705                 710                 715                 720
Gly Arg Val Thr Tyr Val Glu Met Gln Val Ser Glu Pro Leu Glu Glu
                725                 730                 735
Val Val Arg Leu Ser Ser Ser Arg Glu His Asp Ile Ile Leu Val Gly
            740                 745                 750
Arg Ser Arg Arg Pro Thr Pro Phe Leu Glu Arg Phe Arg Arg Lys His
        755                 760                 765
Ala Glu Tyr Ala Glu Leu Gly Pro Ile Gly Asp Ala Leu Met Ala Pro
    770                 775                 780
Gln Val Arg Ala Ser Val Leu Val Phe Gln Gln His Asp His Val Leu
785                 790                 795                 800
Ala Asp Pro Leu Pro Asn Thr Ser Glu Thr Gly Ala Val Lys Glu Leu
                805                 810                 815
Gln Thr Phe Pro Ser Ser Lys Glu Leu Val Asp Arg Lys Gly Asp Val
            820                 825                 830
Gln Lys Ile Asp Leu Ser Ser Pro Asp His Arg Val Tyr Met Thr Arg
        835                 840                 845
Val

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
caggaaacag ctatgacc                                                18

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 7
ctaaagggaa caaaagctg                                               19

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 8
tgtaaaacga cggccagt                                                18
```

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 9
ctgcccgggt accggaaggt tgaagatggc gac                                33

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 10
gacgagctct agacactaac ttgattcaac tgtg                               34

<210> SEQ ID NO 11
<211> LENGTH: 733
<212> TYPE: DNA
<213> ORGANISM: Homo sapiens

<400> SEQUENCE: 11
gggatccgga gcccaaatct tctgacaaaa ctcacacatg cccaccgtgc ccagcacctg    60
aattcgaggg tgcaccgtca gtcttcctct tccccccaaa acccaaggac accctcatga   120
tctcccggac tcctgaggtc acatgcgtgg tggtggacgt aagccacgaa gaccctgagg   180
tcaagttcaa ctggtacgtg gacggcgtgg aggtgcataa tgccaagaca aagccgcggg   240
aggagcagta caacagcacg taccgtgtgg tcagcgtcct caccgtcctg caccaggact   300
ggctgaatgg caaggagtac aagtgcaagg tctccaacaa agccctccca accccatcg   360 agaaaaccat ctccaaagcc aaagggcagc ccgagaacc acaggtgtac accctgcccc   420
catcccggga tgagctgacc aagaaccagg tcagcctgac ctgcctggtc aaaggcttct   480
atccaagcga catcgccgtg gagtgggaga gcaatgggca gccggagaac aactacaaga   540
ccacgcctcc cgtgctggac tccgacggct ccttcttcct ctacagcaag ctcaccgtgg   600
acaagagcag gtggcagcag gggaacgtct tctcatgctc cgtgatgcat gaggctctgc   660
acaaccacta cacgcagaag agcctctccc tgtctccggg taaatgagtg cgacggccgc   720
gactctagag gat                                                     733

<210> SEQ ID NO 12
<211> LENGTH: 62
<212> TYPE: DNA
<213> ORGANISM: Artificial Sequence
<220> FEATURE:
<223> OTHER INFORMATION: Description of Artificial Sequence: Primer

<400> SEQUENCE: 12
ggccagtgaa ttgtaatacg ctcactatag ggaggcggtt tttttttttt tttttttttt    60
tt                                                                  62

<210> SEQ ID NO 13
<211> LENGTH: 40
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 13

Ile Leu Glu Phe Asp Glu Glu Leu Phe Phe Ile Tyr Leu Leu Pro Pro
1               5                   10                  15

Ile Ile Phe Asn Ala Gly Phe Gln Val Lys Lys Lys Glu Phe Phe Arg
                20                  25                  30

Asn Phe Ile Thr Ile Met Phe Phe
            35                  40

<210> SEQ ID NO 14
<211> LENGTH: 26
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 14

Gln Asp Glu Thr Pro Leu Leu Tyr Ser Leu Val Phe Gly Glu Gly Val
1               5                   10                  15

Val Asn Asp Ala Thr Ser Val Val Leu Ser
                20                  25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 15
cgtttgcgca tgcccctggt cgctt                                    25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 16
caggacgaag gaaacaccga cacct                                    25

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 17
ctgcccgggt accattggca ccagcaagat ggcggacgct                    40

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 18
gcgtctagac ccgggtcata tacacgcggt ggtcaggag                     39

<210> SEQ ID NO 19

```
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 19
ctgcccgggt accggaaggt tgaagatggc gac                                    33

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      FLAG tag

<400> SEQUENCE: 20

Asp Tyr Lys Asp Asp Asp Asp Lys
  1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: 6-His tag

<400> SEQUENCE: 21

His His His His His His
  1               5

<210> SEQ ID NO 22
<211> LENGTH: 25
<212> TYPE: PRT
<213> ORGANISM: Oryza sp.

<400> SEQUENCE: 22

Met Lys Asn Thr Ser Ser Leu Cys Leu Leu Leu Val Val Leu Cys
  1               5                  10                  15

Ser Leu Thr Cys Asn Ser Gly Gln Ala
              20                  25

<210> SEQ ID NO 23
<211> LENGTH: 535
<212> TYPE: PRT
<213> ORGANISM: Oryza sativa

<400> SEQUENCE: 23

Met Gly Met Glu Val Ala Ala Ala Arg Leu Gly Ala Leu Tyr Thr Thr
  1               5                  10                  15

Ser Asp Tyr Ala Ser Val Val Ser Ile Asn Leu Phe Val Ala Leu Leu
              20                  25                  30

Cys Ala Cys Ile Val Leu Gly His Leu Leu Glu Glu Asn Arg Trp Val
          35                  40                  45

Asn Glu Ser Ile Thr Ala Leu Ile Ile Gly Leu Cys Thr Gly Val Val
      50                  55                  60

Ile Leu Leu Met Thr Lys Gly Lys Ser Ser His Leu Phe Val Phe Ser
 65                  70                  75                  80

Glu Asp Leu Phe Phe Ile Tyr Leu Leu Pro Pro Ile Ile Phe Asn Ala
                  85                  90                  95

Gly Phe Gln Val Lys Lys Lys Gln Phe Phe Arg Asn Phe Met Thr Ile
              100                 105                 110
```

-continued

```
Thr Leu Phe Gly Ala Val Gly Thr Met Ile Ser Phe Phe Thr Ile Ser
            115                 120                 125
Ile Ala Ala Ile Ala Ile Phe Ser Arg Met Asn Ile Gly Thr Leu Asp
        130                 135                 140
Val Gly Asp Phe Leu Ala Ile Gly Ala Ile Phe Ser Ala Thr Asp Ser
145                 150                 155                 160
Val Cys Thr Leu Gln Val Leu Asn Gln Asp Glu Thr Pro Phe Leu Tyr
                165                 170                 175
Ser Leu Val Phe Gly Glu Gly Val Val Asn Asp Ala Thr Ser Ile Val
            180                 185                 190
Leu Phe Asn Ala Leu Gln Asn Phe Asp Leu Val His Ile Asp Ala Ala
        195                 200                 205
Val Val Leu Lys Phe Leu Gly Asn Phe Phe Tyr Leu Phe Leu Ser Ser
    210                 215                 220
Thr Phe Leu Gly Val Phe Ala Gly Leu Leu Ser Ala Tyr Ile Ile Lys
225                 230                 235                 240
Lys Leu Tyr Ile Gly Arg His Ser Thr Asp Arg Glu Val Ala Leu Met
                245                 250                 255
Met Leu Met Ala Tyr Leu Ser Tyr Met Leu Ala Glu Leu Leu Asp Leu
            260                 265                 270
Ser Gly Ile Leu Thr Val Phe Phe Cys Gly Ile Val Met Ser His Tyr
        275                 280                 285
Thr Trp His Asn Val Thr Glu Ser Ser Arg Val Thr Thr Lys His Ala
    290                 295                 300
Phe Ala Thr Leu Ser Phe Ile Ala Glu Thr Phe Leu Phe Leu Tyr Val
305                 310                 315                 320
Gly Met Asp Ala Leu Asp Ile Glu Lys Trp Glu Phe Ala Ser Asp Arg
                325                 330                 335
Pro Gly Lys Ser Ile Gly Ile Ser Ser Ile Leu Leu Gly Leu Val Leu
            340                 345                 350
Ile Gly Arg Ala Ala Phe Val Phe Pro Leu Ser Phe Leu Ser Asn Leu
        355                 360                 365
Thr Lys Lys Ala Pro Asn Glu Lys Ile Thr Trp Arg Gln Gln Val Val
    370                 375                 380
Ile Trp Trp Ala Gly Leu Met Arg Gly Ala Val Ser Ile Ala Leu Ala
385                 390                 395                 400
Tyr Asn Lys Phe Thr Arg Ser Gly His Thr Gln Leu His Gly Asn Ala
                405                 410                 415
Ile Met Ile Thr Ser Thr Ile Thr Val Val Leu Phe Ser Thr Met Val
            420                 425                 430
Phe Gly Met Met Thr Lys Pro Leu Ile Arg Leu Leu Leu Pro Ala Ser
        435                 440                 445
Gly His Pro Val Thr Ser Glu Pro Ser Ser Pro Lys Ser Leu His Ser
    450                 455                 460
Pro Leu Leu Thr Ser Met Gln Gly Ser Asp Leu Glu Ser Thr Thr Asn
465                 470                 475                 480
Ile Val Arg Pro Ser Ser Leu Arg Met Leu Leu Thr Lys Pro Thr His
                485                 490                 495
Thr Val His Tyr Tyr Trp Arg Lys Phe Asp Asp Ala Leu Met Arg Pro
            500                 505                 510
Met Phe Gly Gly Arg Gly Phe Val Pro Phe Ser Pro Gly Ser Pro Thr
        515                 520                 525
```

```
Glu Gln Ser His Gly Gly Arg
        530                 535

<210> SEQ ID NO 24
<211> LENGTH: 537
<212> TYPE: PRT
<213> ORGANISM: Arabidopsis sp.

<400> SEQUENCE: 24

Met Leu Asp Ser Leu Val Ser Lys Leu Pro Ser Leu Ser Thr Ser Asp
 1               5                  10                  15

His Ala Ser Val Val Ala Leu Asn Leu Phe Val Ala Leu Leu Cys Ala
            20                  25                  30

Cys Ile Val Leu Gly His Leu Leu Glu Glu Asn Arg Trp Met Asn Glu
        35                  40                  45

Ser Ile Thr Ala Leu Leu Ile Gly Leu Gly Thr Gly Val Thr Ile Leu
    50                  55                  60

Leu Ile Ser Lys Gly Lys Ser Ser His Leu Leu Val Phe Ser Glu Asp
65                  70                  75                  80

Leu Phe Phe Ile Tyr Leu Leu Pro Pro Ile Ile Phe Asn Ala Gly Phe
                85                  90                  95

Gln Val Lys Lys Lys Gln Phe Phe Arg Asn Phe Val Thr Ile Met Leu
            100                 105                 110

Phe Gly Ala Val Gly Thr Ile Ile Ser Cys Thr Ile Ile Ser Leu Gly
        115                 120                 125

Val Thr Gln Phe Phe Lys Lys Leu Asp Ile Gly Thr Phe Asp Leu Gly
    130                 135                 140

Asp Tyr Leu Ala Ile Gly Ala Ile Phe Ala Ala Thr Asp Ser Val Cys
145                 150                 155                 160

Thr Leu Gln Val Leu Asn Gln Asp Glu Thr Pro Leu Leu Tyr Ser Leu
                165                 170                 175

Val Phe Gly Glu Gly Val Val Asn Asp Ala Thr Ser Val Val Val Phe
            180                 185                 190

Asn Ala Ile Gln Ser Phe Asp Leu Thr His Leu Asn His Glu Ala Ala
        195                 200                 205

Phe His Leu Leu Gly Asn Phe Leu Tyr Leu Phe Leu Leu Ser Thr Leu
    210                 215                 220

Leu Gly Ala Ala Thr Gly Leu Ile Ser Ala Tyr Val Ile Lys Lys Leu
225                 230                 235                 240

Tyr Phe Gly Arg His Ser Thr Asp Arg Glu Val Ala Leu Met Met Leu
                245                 250                 255

Met Ala Tyr Leu Ser Tyr Met Leu Ala Glu Leu Phe Asp Leu Ser Gly
            260                 265                 270

Ile Leu Thr Val Phe Phe Cys Gly Ile Val Met Ser His Tyr Thr Trp
        275                 280                 285

His Asn Val Thr Glu Ser Ser Arg Ile Thr Thr Lys His Thr Phe Ala
    290                 295                 300

Thr Leu Ser Phe Leu Ala Glu Thr Phe Ile Phe Leu Tyr Val Gly Met
305                 310                 315                 320

Asp Ala Leu Asp Ile Asp Lys Trp Arg Ser Val Ser Asp Thr Pro Gly
                325                 330                 335

Thr Ser Ile Ala Val Ser Ser Ile Leu Met Gly Leu Val Met Val Gly
            340                 345                 350

Arg Ala Ala Phe Val Phe Pro Leu Ser Phe Leu Ser Asn Leu Ala Lys
        355                 360                 365
```

```
Lys Asn Gln Ser Glu Lys Ile Asn Phe Asn Met Gln Val Val Ile Trp
    370                 375                 380

Trp Ser Gly Leu Met Arg Gly Ala Val Ser Met Ala Leu Ala Tyr Asn
385                 390                 395                 400

Lys Phe Thr Arg Ala Gly His Thr Asp Val Arg Gly Asn Ala Ile Met
            405                 410                 415

Ile Thr Ser Thr Ile Thr Val Cys Leu Phe Ser Thr Val Phe Gly
            420                 425                 430

Met Leu Thr Lys Pro Leu Ile Ser Tyr Leu Leu Pro His Gln Asn Ala
        435                 440                 445

Thr Thr Ser Met Leu Ser Asp Asp Asn Thr Pro Lys Ser Ile His Ile
    450                 455                 460

Pro Leu Leu Asp Gln Asp Ser Phe Ile Glu Pro Ser Gly Asn His Asn
465                 470                 475                 480

Val Pro Arg Pro Asp Ser Ile Arg Gly Phe Leu Thr Arg Pro Thr Arg
                485                 490                 495

Thr Val His Tyr Tyr Trp Arg Gln Phe Asp Asp Ser Phe Met Arg Pro
            500                 505                 510

Val Phe Gly Gly Arg Phe Val Pro Phe Val Pro Gly Ser Pro Thr Glu
        515                 520                 525

Arg Asn Pro Pro Asp Leu Ser Lys Ala
    530                 535

<210> SEQ ID NO 25
<211> LENGTH: 649
<212> TYPE: PRT
<213> ORGANISM: Drosophila melanogaster

<400> SEQUENCE: 25

Met Arg Val Trp Val Ala Tyr Ser Ala Ala Leu Leu Leu Leu Val
1               5                   10                  15

His Ala Gly Pro Glu Ser Ile Ser Gly Gln Glu Val Pro Gln Ser Lys
            20                  25                  30

Thr Ser Ser Asn Thr Thr Thr Thr Asp Asn Ser Ser Ile His Thr
        35                  40                  45

Val Ser Asp Val Phe Val Asn Ser Pro Leu Gly Asn Val Thr Pro Ser
    50                  55                  60

Ile Ser Ala Ser Gly Asn Ala Ser Thr Thr Lys Arg Gly Asn Ala Ser
65                  70                  75                  80

Thr Leu Val Thr Asp Pro Pro Leu Ile Asp Ser His Ala Val Glu Gln
                85                  90                  95

Glu His Asn Ser Ser Leu Ser Leu Phe Val Ile Cys Val Ile Met
            100                 105                 110

Leu Gly Ile Leu Leu Ile His Ser Met Leu Gln Thr Gly Phe Gln Tyr
        115                 120                 125

Leu Pro Glu Ser Ile Val Val Phe Leu Gly Ala Phe Ile Gly Leu
    130                 135                 140

Ser Leu Asn Val Met Ser Gly Gln Asn Gly Ser Trp Lys Arg Glu Glu
145                 150                 155                 160

Val Phe Ser Pro Met Gly Phe Leu Val Leu Pro Pro Ile Ile
                165                 170                 175

Phe Glu Ser Gly Tyr Asn Leu His Lys Gly Asn Phe Gln Asn Ile
            180                 185                 190

Gly Ser Ile Leu Val Phe Ala Ile Phe Gly Thr Thr Ile Ser Ala Leu
```

```
            195                 200                 205
Val Ile Gly Ala Gly Ile Tyr Leu Leu Gly Leu Gly Glu Val Ala Phe
210                 215                 220

Arg Leu Ser Phe Ser Glu Ser Phe Ala Phe Gly Ser Leu Ile Ser Ala
225                 230                 235                 240

Val Asp Pro Val Ala Thr Val Ala Ile Phe His Ala Leu Asp Val Asp
                    245                 250                 255

Pro Ile Leu Asn Met Leu Val Phe Gly Glu Ser Ile Leu Asn Asp Ala
                260                 265                 270

Ile Ser Ile Val Leu Thr Ala Ser Ile Thr Gln Ser Ala Asn Val Asn
            275                 280                 285

Ala Glu Ala Ser Thr Gly Glu Ala Met Phe Ser Ala Leu Lys Thr Phe
        290                 295                 300

Cys Ala Met Phe Phe Ala Ser Ala Gly Ile Gly Val Ile Phe Ala Leu
305                 310                 315                 320

Ile Ser Ala Leu Leu Leu Lys His Ile Asp Leu Arg Lys His Pro Ser
                325                 330                 335

Leu Glu Phe Ala Met Met Leu Met Phe Thr Tyr Ala Pro Tyr Val Leu
                340                 345                 350

Ala Glu Gly Ile His Leu Ser Gly Ile Met Ala Ile Leu Phe Cys Gly
            355                 360                 365

Ile Val Met Ser His Tyr Thr His Phe Asn Leu Ser Thr Val Thr Gln
        370                 375                 380

Ile Thr Met Gln Gln Thr Met Arg Thr Leu Ala Phe Ile Ala Glu Thr
385                 390                 395                 400

Cys Val Phe Ala Tyr Leu Gly Leu Ala Ile Phe Ser Phe Lys His Gln
                    405                 410                 415

Val Glu Leu Ser Phe Val Ile Trp Ala Ile Val Leu Cys Leu Ile Gly
                420                 425                 430

Arg Ala Cys Asn Ile Phe Pro Leu Ala Phe Leu Val Asn Lys Phe Arg
            435                 440                 445

Glu His Lys Ile Asn Asn Lys Met Gln Phe Ile Met Trp Phe Ser Gly
        450                 455                 460

Leu Arg Gly Ala Ile Ser Tyr Ala Leu Ser Leu His Leu Asn Leu Asp
465                 470                 475                 480

Ser Gln Glu Lys Arg His Val Ile Ile Thr Thr Leu Ile Ile Val
                    485                 490                 495

Leu Phe Thr Thr Leu Val Leu Gly Gly Ser Thr Met Pro Leu Leu Lys
                500                 505                 510

Tyr Leu Lys Pro Gly Lys Lys Arg Ala Arg Gly Ser Gly Arg Asn
            515                 520                 525

Ala Ala Glu Glu Gly Gly Arg Arg Asn Gly Ser Gly Arg Lys Arg Ser
        530                 535                 540

Lys Ser Ile Ser Leu Ser Lys Thr Arg Glu Trp Gly Gln Ala Ile Asp
545                 550                 555                 560

Ser Glu His Leu Ser Glu Leu Thr Glu Glu Asp Val Thr Phe Thr
                    565                 570                 575

Gln Ala Arg Asp Arg Phe Gly Arg Met Asp Arg Lys Tyr Phe Ile Pro
                580                 585                 590

Phe Phe Thr Arg Arg Phe Asn Ser Gln Glu Leu His Glu Cys Lys Ser
            595                 600                 605

Gln Met Ala Asp Leu Thr Asn Lys Trp Tyr Gln Ala Ile Arg Val Ser
        610                 615                 620
```

```
Pro Leu Asp Ser Asp Glu Ser Asp Glu Glu Ile Gly Leu Ala Ala Ser
625                 630                 635                 640

Thr Ser Gln Ile His Leu Thr Arg Ser
                645
```

<210> SEQ ID NO 26
<211> LENGTH: 694
<212> TYPE: PRT
<213> ORGANISM: Caenorhabditis elegans

<400> SEQUENCE: 26

```
Met Met Leu Ser Val Glu Glu Gln Val Leu Arg Asn Asn Ile Glu Leu
 1               5                  10                  15

Met Phe Thr Phe Asn Ser Leu Lys Ile Leu Ala Asn Gly Val Thr Trp
                20                  25                  30

Gln Leu Trp Glu Ser Thr Leu Asn Gln Gly Thr Ala Thr Ser Gly Ile
            35                  40                  45

Met Arg Phe Ala Leu Lys Thr Ala Leu Ser Ile Cys Ile Phe Leu Leu
    50                  55                  60

Ile Phe Gln Thr Val Asp Ser Asp Ser Ser Asp Ser Ser Ala Ser Ala
65                  70                  75                  80

Ser Val Val Ser Gly Ala Val Lys Ser Glu Asp Thr Val Val Ala Val
                85                  90                  95

Asn Lys Thr Asp Val Leu Gly Glu Ala Ile Asp Ala Asn Ala Thr Ser
            100                 105                 110

Leu Glu Gln His Gly Ala Ala Ile Val Gly Asn Val Ser Glu Glu Lys
        115                 120                 125

Lys Arg Ser Leu Ala Ile Phe Phe Ile Leu Phe Val Ile Met Leu Ala
130                 135                 140

Thr Leu Val Val His Met Leu Ile Val Ser Lys Ile His Trp Met Pro
145                 150                 155                 160

Glu Ser Leu Ala Ile Val Ala Leu Gly Ala Leu Ile Gly Ser Ile Leu
                165                 170                 175

Ser Tyr Ser Arg Arg Asp Trp Ser Glu Ile Glu Ala Leu Ser Pro Asp
            180                 185                 190

Val Phe Phe Leu Val Leu Leu Pro Pro Ile Ile Phe Glu Asn Ala Tyr
        195                 200                 205

Asn Leu Asn Lys Gly Tyr Phe Phe Ser Asn Phe Val Pro Ile Leu Thr
    210                 215                 220

Phe Ala Ile Phe Gly Thr Thr Ile Ser Ala Met Val Ile Gly Ala Gly
225                 230                 235                 240

Leu Tyr Ile Leu Gly Ala Ile Gly Leu Ile Phe Glu Phe Thr Phe Phe
                245                 250                 255

Glu Cys Phe Ala Phe Ala Ala Met Ile Ser Ala Val Asp Pro Val Gly
            260                 265                 270

Thr Leu Ala Ile Phe Gln Ala Val Lys Val Glu Ser Leu Leu Tyr Met
        275                 280                 285

Leu Val Phe Gly Glu Ser Met Leu Asn Asp Ala Val Ser Ile Val Leu
    290                 295                 300

Ala Ala Thr Ala Leu Arg His Ala Lys Pro Ser Phe Asn Ser Leu Pro
305                 310                 315                 320

Ala Ser Glu Ile Ile Thr Ser Ala Phe Val Thr Phe Thr Glu Met Phe
                325                 330                 335

Phe Phe Ser Ala Cys Leu Gly Val Gly Ile Gly Leu Leu Ser Ala Leu
```

```
                340             345             350
Leu Phe Lys His Val Asp Leu Arg Lys Thr Pro Ser Leu Glu Phe Ala
            355                 360                 365
Leu Leu Leu Ile Phe Ser Tyr Ile Pro Tyr Gly Phe Ala Glu Ala Leu
            370                 375                 380
Asp Leu Ser Gly Ile Met Ala Ile Leu Phe Cys Gly Ile Ser Met Ser
385                 390                 395                 400
Gln Phe Thr Arg His Asn Val Ser Pro Ile Ala Gln Ile Thr Phe Arg
                405                 410                 415
His Thr Phe Arg Thr Ile Ser Phe Val Ala Glu Thr Ser Thr Phe Ala
            420                 425                 430
Tyr Ile Gly Met Ala Phe Phe Thr Ile Lys Leu Asn Phe Ala Pro Trp
            435                 440                 445
Leu Ile Phe Trp Ser Val Val Leu Cys Leu Leu Gly Arg Ala Cys Asn
            450                 455                 460
Val Phe Pro Leu Ala Tyr Leu Val Asn Gln Cys Arg Lys Asp Val Gln
465                 470                 475                 480
Ile Ser Met Lys Asn Gln Ile Ile Met Trp Phe Ser Gly Met Arg Tyr
                485                 490                 495
Met Asp Leu Asp Lys Glu Lys Lys Ser Ile Leu Leu Thr Thr Val Leu
            500                 505                 510
Phe Leu Ile Leu Phe Thr Thr Ile Phe Leu Gly Gly Ser Ala Leu Pro
            515                 520                 525
Phe Ile Ser Phe Ile Asn Arg Cys Tyr Pro Asn Glu Arg Gln Arg Lys
            530                 535                 540
Arg Arg Arg Thr Pro Arg Asn Lys Glu Ser Thr Gly Asn Ser Ser Ala
545                 550                 555                 560
Leu Met Met Ser Lys Thr Gln Glu Met Ser Phe Gly Ser Asp Asp
                565                 570                 575
Trp Gly Pro Lys Lys Ser Ala Leu Asp Ala Thr Ser Ser Ala Gly Arg
            580                 585                 590
Ile Met Arg Gln Leu Phe Val Arg Lys Phe Thr Ala Ile Glu Arg Leu
            595                 600                 605
Glu Asn Arg Asp Lys Leu Ala Ala Leu Thr Lys Arg Ala Leu Ala Ser
            610                 615                 620
Asp Gln Met Thr Asp Ser Asp Val Glu Phe Gly Gly Gly Gly
625                 630                 635                 640
Val Gly Gly Gly Arg Met Lys Asp Val Thr Pro Thr Arg Gly
                645                 650                 655
Arg Ser Gly Ser Arg Asn Ser Ser Asp Val Ile Ile Ser Ala Gly Gly
            660                 665                 670
Gly Gly Val Ser Gly Glu His His Leu Leu Ile Ser Ser Gly Ser Asp
            675                 680                 685
Ser Ser Thr Asn Glu Phe
        690

<210> SEQ ID NO 27
<211> LENGTH: 78
<212> TYPE: PRT
<213> ORGANISM: Physcomitrella patens

<400> SEQUENCE: 27

Leu Glu Leu Asp Met Thr Gln Ile Arg Lys Thr Gly Lys Gln Ala Met
1               5                   10                  15
```

```
Ser Ile Ala Ala Ala Gly Ile Thr Leu Pro Phe Val Ala Gly Val Gly
             20                  25                  30

Val Ser Phe Val Leu His Leu Thr Ile Ala Pro Glu Gly Ala Phe Gly
         35                  40                  45

Pro Phe Leu Val Phe Met Gly Val Ala Met Ser Ile Thr Ala Phe Pro
     50                  55                  60

Val Leu Ala Arg Ile Leu Ala Glu Arg Lys Leu Leu Thr Thr
 65                 70                  75

<210> SEQ ID NO 28
<211> LENGTH: 78
<212> TYPE: PRT
<213> ORGANISM: Arabidopsis thaliana

<400> SEQUENCE: 28

Leu Glu Leu Asp Pro Lys Ser Leu Lys Arg Thr Gly Lys Arg Ala Leu
  1               5                  10                  15

Ser Ile Ala Leu Ala Gly Ile Thr Leu Pro Phe Val Leu Gly Ile Gly
             20                  25                  30

Thr Ser Phe Ala Leu Arg Ser Ser Ile Ala Asp Gly Ala Ser Lys Ala
         35                  40                  45

Pro Phe Leu Val Phe Met Gly Val Ala Leu Ser Ile Thr Ala Phe Pro
     50                  55                  60

Val Leu Ala Arg Ile Leu Ala Glu Ile Lys Leu Leu Thr Thr
 65                 70                  75

<210> SEQ ID NO 29
<211> LENGTH: 60
<212> TYPE: PRT
<213> ORGANISM: Oryza sativa

<400> SEQUENCE: 29

Gly Lys Ser Ser His Leu Phe Val Phe Ser Glu Asp Leu Phe Phe Ile
  1               5                  10                  15

Tyr Leu Leu Pro Pro Ile Ile Phe Asn Ala Gly Phe Gln Val Lys Lys
             20                  25                  30

Lys Gln Phe Phe Arg Asn Phe Met Thr Ile Thr Leu Phe Gly Ala Val
         35                  40                  45

Gly Thr Met Ile Ser Phe Phe Thr Ile Ser Ile Ala
     50                  55                  60

<210> SEQ ID NO 30
<211> LENGTH: 60
<212> TYPE: PRT
<213> ORGANISM: Arabidopsis thaliana

<400> SEQUENCE: 30

Gly Lys Asn Ser His Leu Leu Val Phe Ser Glu Asp Leu Phe Phe Ile
  1               5                  10                  15

Tyr Leu Leu Pro Pro Ile Ile Phe Asn Ala Gly Phe Gln Val Lys Lys
             20                  25                  30

Lys Gln Phe Phe Arg Asn Phe Val Thr Ile Met Ala Phe Gly Ala Ile
         35                  40                  45

Gly Thr Val Val Ser Cys Thr Ile Ile Ser Leu Gly
     50                  55                  60
```

```
<210> SEQ ID NO 31
<211> LENGTH: 78
<212> TYPE: PRT
<213> ORGANISM: Arabidopsis thaliana

<400> SEQUENCE: 31

Leu Glu Leu Asp Phe Ala Ala Ile Lys Lys Thr Gly Lys Lys Ser Leu
1               5                   10                  15

Leu Ile Ala Ile Ala Gly Ile Ser Leu Pro Phe Ile Val Gly Val Gly
                20                  25                  30

Thr Ser Phe Val Leu Ser Ala Thr Ile Ser Lys Gly Val Asp Gln Leu
            35                  40                  45

Pro Phe Ile Val Phe Met Gly Val Ala Leu Ser Ile Thr Ala Phe Pro
        50                  55                  60

Val Leu Ala Arg Ile Leu Ala Glu Leu Lys Leu Leu Thr Thr
65                  70                  75

<210> SEQ ID NO 32
<211> LENGTH: 78
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (5)..(7)
<223> OTHER INFORMATION: Variable amino acid
<220> FEATURE:
<221> NAME/KEY: MOD_RES
<222> LOCATION: (14)
<223> OTHER INFORMATION: Variable amino acid
<220> FEATURE:
<221> NAME/KEY: MOD_RES
<222> LOCATION: (17)
<223> OTHER INFORMATION: Variable amino acid
<220> FEATURE:
<221> NAME/KEY: MOD_RES
<222> LOCATION: (29)
<223> OTHER INFORMATION: Variable amino acid
<220> FEATURE:
<221> NAME/KEY: MOD_RES
<222> LOCATION: (33)
<223> OTHER INFORMATION: Variable amino acid
<220> FEATURE:
<221> NAME/KEY: MOD_RES
<222> LOCATION: (38)..(39)
<223> OTHER INFORMATION: Variable amino acid
<220> FEATURE:
<221> NAME/KEY: MOD_RES
<222> LOCATION: (43)
<223> OTHER INFORMATION: Variable amino acid
<220> FEATURE:
<221> NAME/KEY: MOD_RES
<222> LOCATION: (46)
<223> OTHER INFORMATION: Variable amino acid
<220> FEATURE:
<221> NAME/KEY: MOD_RES
<222> LOCATION: (73)
<223> OTHER INFORMATION: Variable amino acid

<400> SEQUENCE: 32

Leu Glu Leu Asp Xaa Xaa Xaa Ile Lys Lys Thr Gly Lys Xaa Ala Leu
1               5                   10                  15

Xaa Ile Ala Ser Ala Gly Ile Thr Leu Pro Phe Val Xaa Gly Leu Gly
                20                  25                  30
```

-continued

```
Xaa Ser Phe Leu Leu Xaa Xaa Thr Ile Ala Xaa Ala Gly Xaa Gln Val
        35                  40                  45

Pro Phe Leu Val Phe Met Gly Val Ala Leu Ser Ile Thr Ala Phe Pro
    50                  55                  60

Val Leu Ala Arg Ile Leu Ala Glu Xaa Lys Leu Leu Thr Thr
65                  70                  75
```